US011918397B2

(12) United States Patent
Harper et al.

(10) Patent No.: US 11,918,397 B2
(45) Date of Patent: Mar. 5, 2024

(54) MULTI-AXIS MEDICAL IMAGING

(71) Applicant: Leo Cancer Care, Inc., Middleton, WI (US)

(72) Inventors: Brent Melvin Harper, New Glarus, WI (US); Thomas Rockwell Mackie, Verona, WI (US); Stephen Kevin Towe, Lewes (GB); Alan Dart Baldwin, San Jose, CA (US); Timothy John Holzmann, Madison, WI (US); Anthony Westwood, Forest Row (GB)

(73) Assignee: Leo Cancer Care, Inc., Middleton, WI (US)

(*) Notice: Subject to any disclaimer, the term of this patent is extended or adjusted under 35 U.S.C. 154(b) by 150 days.

(21) Appl. No.: 17/535,091

(22) Filed: Nov. 24, 2021

(65) Prior Publication Data

US 2022/0183641 A1 Jun. 16, 2022

Related U.S. Application Data

(60) Provisional application No. 63/121,304, filed on Dec. 4, 2020.

(51) Int. Cl.
| *A61B 6/00* | (2006.01) |
| *A61B 6/03* | (2006.01) |
| *A61B 6/04* | (2006.01) |
| *A61B 34/10* | (2016.01) |

(52) U.S. Cl.
CPC ............ *A61B 6/4447* (2013.01); *A61B 6/035* (2013.01); *A61B 6/0407* (2013.01); *A61B 6/447* (2013.01); *A61B 6/4476* (2013.01); *A61B 6/5223* (2013.01); *A61B 6/54* (2013.01); *A61B 6/586* (2013.01); *A61B 34/10* (2016.02); *A61B 2034/105* (2016.02); *A61B 2034/107* (2016.02)

(58) Field of Classification Search
CPC .............................. A61B 6/035; A61B 6/4476
See application file for complete search history.

(56) References Cited

U.S. PATENT DOCUMENTS

| 4,316,091 | A | 2/1982 | Bernardi |
| 5,923,417 | A | 7/1999 | Leis |
| 6,061,644 | A | 5/2000 | Leis |
| 7,974,443 | B2 | 7/2011 | Kipman et al. |
| 8,009,022 | B2 | 8/2011 | Kipman et al. |
| 9,301,726 | B2 | 4/2016 | Mackie et al. |
| 2009/0080598 | A1 | 3/2009 | Tashman et al. |
| 2011/0280380 | A1* | 11/2011 | Maschke ............... A61B 6/4411 378/197 |

(Continued)

FOREIGN PATENT DOCUMENTS

WO    WO 2014/013367    1/2014

OTHER PUBLICATIONS

International Search Report and Written Opinion for PCT/US2021/060780, dated Mar. 29, 2022, 16 pages.

(Continued)

*Primary Examiner* — Dani Fox
(74) *Attorney, Agent, or Firm* — Casimir Jones, S.C.; Thomas A. Isenbarger

(57) ABSTRACT

Provided herein is technology relating to radiology and radiotherapy and particularly, but not exclusively, to apparatuses, methods, and systems for multi-axis medical imaging of patients in vertical and horizontal positions.

93 Claims, 30 Drawing Sheets

(56) References Cited

U.S. PATENT DOCUMENTS

2016/0220204 A1  8/2016  Ay et al.
2019/0307415 A1  10/2019  Antikainen
2020/0268327 A1  8/2020  Feain et al.
2023/0073617 A1  3/2023  Aoki et al.

OTHER PUBLICATIONS

Boisbouvier, S. et al. Upright patient positioning for pelvic radiotherapy treatments. Tech Innov Patient Support Radiat Oncol. Nov. 28, 2022;24:124-130.
Eslick E.M. et al. The Nano-X Linear Accelerator: A Compact and Economical Cancer Radiotherapy System Incorporating Patient Rotation. Technol Cancer Res Treat. Oct. 2015;14(5):565-72.
Jinzaki, M. et al. Development of Upright Computed Tomography With Area Detector for Whole-Body Scans: Phantom Study, Efficacy on Workflow, Effect of Gravity on Human Body, and Potential Clinical Impact. Invest Radiol. Feb. 2020;55(2):73-83.
Schreuder, N. et al. Fixed beamlines can replace gantries for particle therapy. Med Phys. Apr. 2022;49(4):2097-2100.
Yamada, Y. et al. Differences in Lung and Lobe Volumes between Supine and Standing Positions Scanned with Conventional and Newly Developed 320-Detector-Row Upright CT: Intra-Individual Comparison. Respiration. 2020;99(7):598-605.
Northern Digital Inc. (NDI) "Optical Tracking Education Guide" Mar. 2022, P/N 10007484 Rev 001.

\* cited by examiner

MULTI-AXIS MEDICAL IMAGING

This application claims priority to U.S. provisional patent application Ser. No. 63/121,304, filed Dec. 4, 2020, which is incorporated herein by reference in its entirety.

FIELD

Provided herein is technology relating to radiology and radiotherapy and particularly, but not exclusively, to apparatuses, methods, and systems for medical imaging.

BACKGROUND

Medical imaging is used to diagnose, stage, plan treatment, guide treatment, and evaluate response to treatment in patients for numerous types of diseases, injuries, and other maladies. In particular, computerized tomography (CT) is a form of medical imaging that produces a three-dimensional model of an object (e.g., a patient or portion thereof) using multiple two-dimensional X-ray measurements taken from different angles. CT imaging produces tomographic (cross-sectional) images of targeted areas of a patient or portion thereof, thus allowing a user to image the interior of the patient without cutting the patient. In conventional CT, a patient is placed horizontally on a couch or gurney and the patient and couch are moved into the CT scanning apparatus. Alternatively, gurneys may be fixed and the CT scanner moves horizontally. New technologies are needed to allow imaging of patients safely in multiple positions, e.g., vertical and/or essentially vertical positions (e.g., standing, sitting, kneeling, etc.) in addition to horizontal positions and/or essentially horizontal positions (e.g., lying (e.g., prone or supine)) and other patient positions such as tilted forwards or backwards and other orthopedic positions.

SUMMARY

Accordingly, the technology described herein relates to medical imaging, e.g., computerized tomography (CT), magnetic resonance imaging (MRI), positron emission tomography (PET), single-photon emission computerized tomography (SPECT), photon counting computed tomography, portal imaging (e.g., prior to a treatment), or scanned projection radiography ("scout view") (e.g., prior to an imaging scan and/or prior to a treatment). Conventional imaging apparatuses (e.g., gantries and gantry systems) have associated risks including potential injury to the patient and/or damage to the apparatus due to movement of the patient, a patient positioning apparatus, a couch, and/or a gurney into position for imaging (e.g., by a scanner). In addition, patients often have anxiety due to patient claustrophobia while inside the scanning apparatus, which can result in reduced image quality (e.g., due to patient movement) or images that do not accurately describe the biological state of the patient (e.g., due to biological responses to anxiety that alter the biological state of the patient). Further, conventional scanning apparatuses are often limited to obtaining images of patients in horizontal positions (e.g., prone, supine, lateral recumbent, etc.)

Obtaining medical images of a vertical patient are sometimes more medically informative than medical scans of a horizontal patient. For example, imaging lungs (e.g., using CT) in a vertical patient provides more useful information for patient treatment than imaging lungs in a horizontal patient. In particular, a lung is better inflated in a patient in an upright position and lesions in the lung (e.g., cancer or fibrosis) are easier to diagnose because of the greater degree of contrast in the vertical patient. Furthermore, in some embodiments, the radiation dose to the lung in a vertical patient is reduced for the same degree of image perspicuity relative to the radiation dose to the lung in a horizontal patient. Other advantages of scanning a vertical patient include diagnosis and imaging of the spine, knees, hips, feet, and other biological systems (e.g., for orthopedic medicine) when bearing a load due to gravity, which more accurately shows the function of these systems and corresponding medical problems to be identified and treated. In some embodiments, imaging the head and neck, lung, breast, liver, pancreas, stomach, and/or esophagus in a vertical patient provides more informative imaging for diagnosis and treatment than imaging the head and neck, lung, breast, liver, pancreas, stomach, and/or esophagus in a horizontal patient.

In addition, treatment of patients in vertical positions has advantages over treatment of patients in horizontal positions. For instance, in some cases, a patient can be positioned more quickly in a standing or seated position. Further, in some cases, patients in a vertical position can be treated at more body locations and from more treatment angles, which not only expands the types of diseases and areas of the body that can be treated but also reduces the total treatment dose provided for appropriate treatment. Accordingly, in some embodiments, the technology described herein relates to an apparatus for imaging a patient in a vertical position prior to treating the patient in the vertical position.

Furthermore, conventional radiotherapy technologies for treating a patient with radiation move a radiotherapy apparatus (e.g., using a gantry) around a stationary patient. Due to the large size of radiotherapy apparatuses, conventional gantries for moving a radiotherapy apparatus are often large, heavy, and expensive. Some previous solutions to this problem have comprised rotating a horizontal patient and maintaining the radiotherapy apparatus in a stationary position, thus obviating the need for large, heavy, and expensive gantries to move the radiotherapy apparatus. However, while moving (e.g., rotating) the patient and using a stationary radiotherapy apparatus would provide advantages of smaller size, complexity, and cost of the gantry and radiotherapy apparatus, rotating a patient in a horizontal (e.g., recumbent) position is impractical, uncomfortable for the patient, and/or difficult in most situations. Thus, as a further improvement for patient radiotherapy treatment, rotating a patient in a vertical position for radiotherapy with a stationary radiotherapy apparatus would address both the problems associated with moving a radiotherapy apparatus (e.g., using a large, heavy, and expensive gantry) and the problems associated with rotating a horizontal patient (e.g., patient comfort and difficulty). However, treating a patient in a vertical position requires imaging the patient in the vertical position to plan the treatment properly. Accordingly, provided herein are embodiments of technology for treating a patient with radiotherapy, e.g., methods comprising imaging a patient in a vertical position (e.g., using the medical imaging apparatus as described herein) and treating the patient in a vertical position. In some embodiments, methods comprise imaging a patient in a vertical position (e.g., a stationary vertical position) using a moving (e.g., translating and/or rotating) scanner (e.g., using a medical imaging apparatus as described herein) and treating the patient in a vertical position by rotating the patient (e.g., slowly rotating the patient) and exposing the patient with radiation from a stationary radiotherapy apparatus.

In some embodiments, imaging a sitting patient is better than imaging a standing patient, e.g., for patient stability (e.g., to minimize patient motion). In some embodiments, imaging a patient comprises providing a patient in a vertical position that is a position in which the patient is sitting and leaning forward or a position in which the patient is sitting and leaning backward.

In particular, the technology relates to a multi-axis medical imaging apparatus that can produce medical images of a patient in a vertical position. The technology can also produce medical images of a patient in a horizontal position and other positions (e.g., a variety of postures including sitting straight up, sitting or standing tilted forwards or backwards, perched, laying recumbent or prone, or other orthopedic positions). The technology is safer than conventional medical imaging apparatuses due to the mechanical design of the technology. The technology has the advantage of being capable of imaging patients in horizontal positions and in vertical positions, thus obviating the need for separate apparatuses for imaging in the horizontal and vertical positions and reducing overall capital costs for imaging apparatuses.

Further, the technology is easier for a user to manipulate than conventional medical imaging apparatuses due to the mechanical design of the technology. For example, in some embodiments, the apparatus comprises a counterbalanced design that allows a user to manipulate and/or position (e.g., tilt, rotate, and/or translate) the scanner manually (e.g., with a force less than the force provided by an average human pushing and/or pulling with an arm and hand). For example, in some embodiments the apparatus comprises a counterbalanced design that allows a user to manipulate and position the scanner manually using a force that is approximately 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N). In some embodiments, the apparatus comprises a counterbalanced design that allows a user to manipulate and position the scanner manually with minimal assistance by a motor. In some embodiments, the apparatus comprises a counterbalanced design that allows a user to manipulate and position the scanner manually without assistance by a motor (e.g., in the event of a power outage). In some embodiments, the apparatus comprises two counterbalanced components having a ratio of masses that is approximately 3:1, 2.5:1, 2:1, 1:1, 1:2, 1:2.5, or 1:3. Accordingly, the apparatus described herein moves with minimal force and thus does not injure a patient and/or cause damage to objects with which it may collide.

In some embodiments, the force used to move the apparatus and/or parts of the apparatus is wholly or partially supplied by a motor or other non-human source. Some embodiments in which the force used to move the apparatus and/or parts of the apparatus is wholly or partially supplied by a motor or other non-human source comprise counterbalancing and some embodiments in which the force used to move the apparatus and/or parts of the apparatus is wholly or partially supplied by a motor or other non-human source do not comprise counterbalancing (e.g., they are counterweight-free and/or counterbalancing-free). Accordingly, in some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor.

Accordingly, provided herein is technology related to a multi-axis medical imaging apparatus (e.g., for obtaining a medical image of a patient positioned in a vertical position, essentially vertical position, and/or substantially vertical position). In some embodiments, the multi-axis medical imaging apparatus is a CT scanning apparatus, an MRI apparatus, a PET scanning apparatus, a SPECT scanning apparatus, a photon counting computed tomography apparatus, and/or an apparatus for portal imaging or for scanned projection radiography (SPR), e.g., to obtain (e.g., record, acquire, provide) a CT scan (e.g., CT image), an MRI scan (e.g., an MRI image), a PET scan (e.g., a PET image), a SPECT scan (e.g., a SPECT image), a photon counted computed tomography scan (e.g., a photon counted computed tomography image), and/or a portal image or a scanogram.

In some embodiments, the multi-axis medical imaging apparatus comprises a stanchion assembly (e.g., comprising one stanchion or a number of stanchions (e.g., comprising one stanchion or a number of stanchions and a base (e.g., comprising one stanchion or a number of stanchions coupled to a base))); a gantry coupled to the stanchion assembly; and a scanner ring coupled to the gantry. In some embodiments, the scanner ring comprises a medical imaging source (e.g., electromagnetic radiation source, X-ray source, gamma ray source, radio wave source, photon source, proton source, positron source, gamma ray source (e.g., gamma rays from a positron source)) and a medical imaging detector (e.g., electromagnetic radiation detector, X-ray detector, photon detector, gamma ray detector).

In some embodiments, the gantry is rotatably coupled to the stanchion assembly. In some embodiments, the gantry is structured to rotate from 0-200 degrees (e.g., 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees) relative to the stanchion assembly. In some embodiments, the gantry is structured to rotate approximately 90 degrees (e.g., 80.0, 80.1, 80.2, 80.3, 80.4, 80.5, 80.6, 80.7, 80.8, 80.9, 81.0, 81.1, 81.2, 81.3, 81.4, 81.5, 81.6, 81.7, 81.8, 81.9, 82.0, 82.1, 82.2, 82.3, 82.4, 82.5, 82.6, 82.7, 82.8, 82.9, 83.0, 83.1, 83.2, 83.3, 83.4, 83.5, 83.6, 83.7, 83.8, 83.9, 84.0, 84.1, 84.2, 84.3, 84.4, 84.5, 84.6, 84.7, 84.8, 84.9, 85.0, 85.1, 85.2, 85.3, 85.4, 85.5, 85.6, 85.7, 85.8, 85.9, 86.0, 86.1, 86.2, 86.3, 86.4, 86.5, 86.6, 86.7, 86.8, 86.9, 87.0, 87.1, 87.2, 87.3, 87.4, 87.5, 87.6, 87.7, 87.8, 87.9, 88.0, 88.1, 88.2, 88.3, 88.4, 88.5, 88.6, 88.7, 88.8, 88.9, 89.0, 89.1, 89.2, 89.3, 89.4, 89.5, 89.6, 89.7, 89.8, 89.9, 90.0, 90.1, 90.2, 90.3, 90.4, 90.5, 90.6, 90.7, 90.8, 90.9, 91.0, 91.1, 91.2, 91.3, 91.4, 91.5, 91.6, 91.7, 91.8, 91.9, 92.0, 92.1, 92.2, 92.3, 92.4, 92.5, 92.6, 92.7, 92.8, 92.9, 93.0, 93.1, 93.2, 93.3, 93.4, 93.5, 93.6, 93.7, 93.8, 93.9, 94.0, 94.1, 94.2, 94.3, 94.4, 94.5, 94.6, 94.7, 94.8, 94.9, 95.0, 95.1, 95.2, 95.3, 95.4, 95.5, 95.6, 95.7, 95.8, 95.9, 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100.0 degrees) relative to the stanchion assembly.

In some embodiments, the gantry comprises a gantry arm rotatably to a stanchion. In some embodiments, the gantry comprises a first gantry arm rotatably coupled to a first stanchion of the stanchion assembly and the gantry comprises a second gantry arm rotatably coupled to a second stanchion of the stanchion assembly. In some embodiments, the stanchion assembly is translatably coupled to a horizontal planar base (e.g., a base on and/or in a floor). In some embodiments, the stanchion assembly is fixedly coupled to a horizontal planar base (e.g., a base on and/or in a floor). In some embodiments, the scanner ring is translatably coupled to the gantry. In some embodiments, the scanner ring is translatably coupled to a gantry arm. In some embodiments, the scanner ring is translatably coupled to a first gantry arm of the gantry and the scanner ring is translatably coupled to a second gantry arm of the gantry. In some embodiments, the scanner ring is structured to translate along a long axis of the gantry arm. In some embodiments, the scanner ring is structured to translate along a long axis of the first gantry arm and along a long axis of the second gantry arm. In some embodiments, the scanner ring is structured to translate 0.20-2.00 m (e.g., 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, or 2.00 m) relative to the gantry. In some embodiments, the scanner ring has a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms).

In some embodiments, a counterbalanced assembly comprises the gantry and the scanner ring. In some embodiments, a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) rotates a counterbalanced assembly comprising the gantry and the scanner ring relative to the stanchion assembly. In some embodiments, a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) translates the scanner ring relative to the gantry. In some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor. In some embodiments, the apparatus comprises two counterbalanced components having a ratio of masses that is approximately 3:1, 2.5:1, 2:1, 1:1, 1:2, 1:2.5, or 1:3. In some embodiments, the scanner ring has a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms) and is counterbalanced by a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms).

In some embodiments, the stanchion assembly comprises a motor operatively engaged with the gantry. In some embodiments, the motor operatively engaged with the gantry is structured to rotate the gantry with respect to the stanchion assembly. In some embodiments, the motor operatively engaged with the gantry is structured to rotate the gantry from 0-200 degrees (e.g., 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees) relative to the stanchion assembly. In some embodiments, the motor operatively engaged with the gantry is structured to rotate the gantry approximately 90 degrees (e.g., 80.0, 80.1, 80.2, 80.3, 80.4, 80.5, 80.6, 80.7, 80.8, 80.9, 81.0, 81.1, 81.2, 81.3, 81.4, 81.5, 81.6, 81.7, 81.8, 81.9, 82.0, 82.1, 82.2, 82.3, 82.4, 82.5, 82.6, 82.7, 82.8, 82.9, 83.0, 83.1, 83.2, 83.3, 83.4, 83.5, 83.6, 83.7, 83.8, 83.9, 84.0, 84.1, 84.2, 84.3, 84.4, 84.5, 84.6, 84.7, 84.8, 84.9, 85.0, 85.1, 85.2, 85.3, 85.4, 85.5, 85.6, 85.7, 85.8, 85.9, 86.0, 86.1, 86.2, 86.3, 86.4, 86.5, 86.6, 86.7, 86.8, 86.9, 87.0, 87.1, 87.2, 87.3, 87.4, 87.5, 87.6, 87.7, 87.8, 87.9, 88.0, 88.1, 88.2, 88.3, 88.4, 88.5, 88.6, 88.7, 88.8, 88.9, 89.0, 89.1, 89.2, 89.3, 89.4, 89.5, 89.6, 89.7, 89.8, 89.9, 90.0, 90.1, 90.2, 90.3, 90.4, 90.5, 90.6, 90.7, 90.8, 90.9, 91.0, 91.1, 91.2, 91.3, 91.4, 91.5, 91.6, 91.7, 91.8, 91.9, 92.0, 92.1, 92.2, 92.3, 92.4, 92.5, 92.6, 92.7, 92.8, 92.9, 93.0, 93.1, 93.2, 93.3, 93.4, 93.5, 93.6, 93.7, 93.8, 93.9, 94.0, 94.1, 94.2, 94.3, 94.4, 94.5, 94.6, 94.7, 94.8, 94.9, 95.0, 95.1, 95.2, 95.3, 95.4, 95.5, 95.6, 95.7, 95.8, 95.9, 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100.0 degrees) relative to the stanchion assembly. In some embodiments, the gantry comprises a motor operatively engaged with the stanchion assembly. In some embodiments, the motor operatively engaged with the stanchion assembly is structured to rotate the gantry with respect to the stanchion assembly.

In some embodiments, the motor operatively engaged with the stanchion assembly is structured to rotate the gantry from 0-200 degrees (e.g., 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees) relative to the stanchion assembly. In some embodiments, the motor operatively engaged with the stanchion assembly is structured to rotate said gantry approximately 90 degrees (e.g., 80.0, 80.1, 80.2, 80.3, 80.4, 80.5, 80.6, 80.7, 80.8, 80.9, 81.0, 81.1, 81.2, 81.3, 81.4, 81.5, 81.6, 81.7, 81.8, 81.9, 82.0, 82.1, 82.2, 82.3, 82.4, 82.5, 82.6, 82.7, 82.8, 82.9, 83.0, 83.1, 83.2, 83.3, 83.4, 83.5, 83.6, 83.7, 83.8, 83.9, 84.0, 84.1, 84.2, 84.3, 84.4, 84.5, 84.6, 84.7, 84.8, 84.9, 85.0, 85.1, 85.2, 85.3, 85.4, 85.5, 85.6, 85.7, 85.8, 85.9, 86.0, 86.1, 86.2, 86.3, 86.4, 86.5, 86.6, 86.7, 86.8, 86.9, 87.0, 87.1, 87.2, 87.3, 87.4, 87.5, 87.6, 87.7, 87.8, 87.9, 88.0, 88.1, 88.2, 88.3, 88.4, 88.5, 88.6, 88.7, 88.8, 88.9, 89.0, 89.1, 89.2, 89.3, 89.4, 89.5, 89.6, 89.7, 89.8, 89.9, 90.0, 90.1, 90.2, 90.3, 90.4, 90.5, 90.6, 90.7, 90.8, 90.9, 91.0, 91.1, 91.2, 91.3, 91.4, 91.5, 91.6, 91.7, 91.8, 91.9, 92.0, 92.1, 92.2, 92.3, 92.4, 92.5, 92.6, 92.7, 92.8, 92.9, 93.0, 93.1, 93.2, 93.3, 93.4, 93.5, 93.6, 93.7, 93.8, 93.9, 94.0, 94.1, 94.2, 94.3, 94.4, 94.5, 94.6, 94.7, 94.8, 94.9, 95.0, 95.1, 95.2, 95.3, 95.4, 95.5, 95.6, 95.7, 95.8, 95.9, 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100.0 degrees) relative to the stanchion assembly.

In some embodiments, the gantry comprises a motor operatively engaged with the scanner ring. In some embodiments, the motor is coupled to a ball screw, a chain, or a belt. In some embodiments, the motor is structured to translate the scanner ring with respect to the gantry. In some embodiments, the motor is structured to translate the scanner ring 0.20-2.00 m (e.g., 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, or 2.00 m) with respect to the gantry. In some embodiments, the ball screw comprises a threaded shaft having a diameter of 15-100 mm (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm) In some embodiments, the motor is structured to translate the scanner ring 5-100 mm (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm) per revolution of the threaded shaft.

In some embodiments, the gantry comprises a supplemental mass component providing a counterweight for the scanner ring. In some embodiments, the gantry comprises a first gantry arm comprising a first portion of the supplemental mass component and a second gantry arm comprising a second portion of the supplemental mass component. In some embodiments, the multi-axis medical imaging apparatus comprises a motor structured to move the supplemental mass component and the scanner ring, e.g., in a coordinated and counterbalanced manner. In some embodiments, the apparatus comprises two counterbalanced components having a ratio of masses that is approximately 3:1, 2.5:1, 2:1, 1:1, 1:2, 1:2.5, or 1:3. In some embodiments, the scanner ring has a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms) and is counterbalanced by a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms).

In some embodiments, the multi-axis medical imaging apparatus is structured to record a medical image of subject in a vertical, essentially vertical, or substantially vertical position. In some embodiments, the subject is in a seated, seated and leaning backward, seated and leaning forward, standing, standing and leaning backward, standing and leaning forward, perched, kneeling, kneeling and leaning forward, or kneeling and leaning backward position. In some embodiments, the scanner ring is structured to move from a first position over the head of the subject to a second position around the subject. In some embodiments, the scanner ring has an inner diameter of 20 cm or more (e.g., 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 cm).

In some embodiments, the technology provides methods of obtaining a medical image of a subject. For example, in some embodiments, methods comprise providing a multi-axis medical imaging apparatus; positioning a subject; and recording a medical image of the subject. In some embodiments, recording a medical image of the subject comprises generating electromagnetic radiation (e.g., photons, gamma rays, X-rays, radio waves) and detecting electromagnetic radiation (e.g., photons, gamma rays, X-rays, radio waves). In some embodiments, recording a medical image of the subject comprises generating a magnetic field (e.g., for MRI).

In some embodiments, the multi-axis medical imaging apparatus (e.g., used in methods described herein) comprises a stanchion assembly; a gantry coupled to the stanchion assembly; and a scanner ring coupled to the gantry. In some embodiments, positioning a subject comprises positioning the subject in a vertical position. In some embodiments, the vertical position is seated, seated and leaning backward, seated and leaning forward, standing, standing and leaning backward, standing and leaning forward, perched, kneeling, kneeling and leaning forward, or kneeling and leaning backward position. In some embodiments, positioning a subject comprises positioning a subject using a patient positioning system and/or a patient support. In some embodiments, a patient positioning system comprises a patient support. In some embodiments, the patient positioning system and patient support are as described in Int'l Pat. App. Pub. No. WO 2019/056055, in U.S. Pat. App. Pub. No. 2020/0268327, and in and in U.S. Pat. App. Ser. No. 63/237,513, each of which is incorporated herein by reference.

In some embodiments, methods further comprise positioning the scanner ring around the subject. In some embodiments, positioning the scanner ring comprises rotating the gantry relative to the stanchion assembly and/or translating the scanner ring relative to the gantry. In some embodiments, rotating the gantry relative to the stanchion assembly comprises applying a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) to an assembly comprising the gantry and the scanner ring. In some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor. In some embodiments, translating the scanner ring relative to the gantry comprises applying a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) to the scanner ring. In some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor. In some embodiments, rotating the gantry relative to the stanchion assembly comprises rotating the gantry 0-200 degrees (e.g., 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees) relative to the stanchion assembly. In some embodiments, rotating the gantry relative to the stanchion assembly comprises rotating the gantry approximately 90 degrees (e.g., 80.0, 80.1, 80.2, 80.3, 80.4, 80.5, 80.6, 80.7, 80.8, 80.9, 81.0, 81.1, 81.2, 81.3, 81.4, 81.5, 81.6, 81.7, 81.8, 81.9, 82.0, 82.1, 82.2, 82.3, 82.4, 82.5, 82.6, 82.7, 82.8, 82.9, 83.0, 83.1, 83.2, 83.3, 83.4, 83.5, 83.6, 83.7, 83.8, 83.9, 84.0, 84.1, 84.2, 84.3, 84.4, 84.5, 84.6, 84.7, 84.8, 84.9, 85.0, 85.1, 85.2, 85.3, 85.4, 85.5, 85.6, 85.7, 85.8, 85.9, 86.0, 86.1, 86.2, 86.3, 86.4, 86.5, 86.6, 86.7, 86.8, 86.9, 87.0, 87.1, 87.2, 87.3, 87.4, 87.5, 87.6, 87.7, 87.8, 87.9, 88.0, 88.1, 88.2, 88.3, 88.4, 88.5, 88.6, 88.7, 88.8, 88.9, 89.0, 89.1, 89.2, 89.3, 89.4, 89.5, 89.6, 89.7, 89.8, 89.9, 90.0, 90.1, 90.2, 90.3, 90.4, 90.5, 90.6, 90.7, 90.8, 90.9, 91.0, 91.1, 91.2, 91.3, 91.4, 91.5, 91.6, 91.7, 91.8, 91.9, 92.0, 92.1, 92.2, 92.3, 92.4, 92.5, 92.6, 92.7, 92.8, 92.9, 93.0, 93.1, 93.2, 93.3, 93.4, 93.5, 93.6, 93.7, 93.8, 93.9, 94.0, 94.1, 94.2, 94.3, 94.4, 94.5, 94.6, 94.7, 94.8, 94.9, 95.0, 95.1, 95.2, 95.3, 95.4, 95.5, 95.6, 95.7, 95.8, 95.9, 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100.0 degrees) relative to the stanchion assembly. In some embodiments, translating the scanner ring relative to the gantry comprises translating the scanner ring 0.2-2.0 m (e.g., 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, or 2.00 m) relative to the gantry. In some embodiments, the apparatus comprises two counterbalanced components having a ratio of masses that is approximately 3:1, 2.5:1, 2:1, 1:1, 1:2, 1:2.5, or 1:3. In some embodiments, the scanner ring has a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms) and is counterbalanced by a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms).

In some embodiments, methods further comprise verifying the configuration of the patient positioning system or a patient support, e.g., as described in Int'l Pat. App. Pub. No. WO 2019/056055, U.S. Pat. App. Pub. No. 2020/0268327, and in U.S. Pat. App. Ser. No. 63/237,513, each of which is incorporated herein by reference. In some embodiments, methods further comprise verifying the position of the subject on the patient positioning system and/or patient support. In some embodiments, verifying the configuration of the patient positioning system and/or patient support comprises imaging the patient positioning system and/or patient support to provide an image and/or model of the patient positioning system and/or patient support and comparing the image and/or model of the patient positioning system and/or patient support to a stored preset patient positioning system configuration and/or patient support configuration. In some embodiments, verifying the position of the subject comprises imaging the subject to provide an image and/or model of the subject and comparing the image and/or model of the subject to a stored preset subject patient position. In some embodiments, methods further comprise imaging the subject to monitor subject position and/or subject motion. In some embodiments, imaging the subject to monitor subject position and/or subject motion is used to assess the quality of an image recorded of said subject (e.g., a moving subject may indicate a decrease in image quality). In some embodiments, imaging the subject to monitor subject position and/or subject motion is used to assess subject safety (e.g., a moving subject may be contacted by a moving component of the imaging apparatus and/or fall off the patient positioning system and/or the patient support).

In some embodiments, methods further comprise imaging the subject to identify the subject and/or to verify the identity of the subject. In some embodiments, methods further comprise translating the multi-axis medical imaging apparatus in the plane of a base (e.g., the floor) movably coupled to the multi-axis medical imaging apparatus. In some embodiments, methods further comprise rotating the gantry relative to the stanchion assembly and/or translating the scanner ring relative to the gantry to provide an exit for the subject.

The technology provides embodiments of systems for recording a medical image of a subject. In some embodiments, systems comprise a multi-axis medical imaging apparatus. In some embodiments, systems further comprise a vertically positioned subject. In some embodiments, the multi-axis medical imaging apparatus comprises a stanchion assembly (e.g., comprising one stanchion; or a number of stanchions); a gantry (e.g., comprising a gantry arm; or a first gantry arm and a second gantry arm) coupled to the stanchion assembly; and a scanner ring coupled to the gantry. In some embodiments, systems further comprise a patient positioning system and/or patient support. In some embodiments, the patient positioning system and/or patient support is as described in Int'l Pat. App. Pub. No. WO 2019/056055, in U.S. Pat. App. Pub. No. 2020/0268327, and in and in U.S. Pat. App. Ser. No. 63/237,513, each of which is incorporated herein by reference. In some embodiments, systems further comprise a vertically positioned subject and the patient positioning system and/or patient support maintains the subject of the vertically positioned subject. In some embodiments, systems further comprise an imaging subsystem (e.g., comprising a camera or a plurality of cameras). In some embodiments, the scanner ring comprises the camera or cameras. In some embodiments, the imaging subsystem is configured to monitor patient position and/or patient movement. In some embodiments, the imaging subsystem is configured to identify a patient and/or verify patient identity. In some embodiments, the imaging subsystem is configured to configure a patient positioning system and/or patient support and/or to confirm a configuration of a patient positioning system and/or patient support. In some embodiments, the imaging subsystem is configured to assist in controlling movement of the multi-axis medical imaging apparatus or a component thereof. In some embodiments, systems further comprise a light curtain subsystem. In some embodiments, the light curtain subsystem comprises a laser source. In some embodiments, the light curtain subsystem comprises a mirror. In some embodiments, the light curtain subsystem comprises a light detector. In some embodiments, the light curtain subsystem is configured to communicate an alert when a light curtain is penetrated. In some embodiments, the alert stops movement of the multi-axis medical imaging apparatus or a component thereof; and/or produces an audible and/or visible alert signal. In some embodiments, systems further comprise a controller configured to control movement of the multi-axis medical imaging apparatus or a component thereof; and/or to initiate and/or terminate recording a medical image.

In some embodiments, the technology relates to uses of a multi-axis medical imaging apparatus to record a medical image of a vertical subject. In some embodiments, the technology relates to use of a multi-axis medical imaging apparatus as described herein, e.g., to record a medical image of a subject. In some embodiments, the technology relates to use of a system comprising a multi-axis medical imaging apparatus to record a medical image of a vertical subject. In some embodiments, the technology relates to use of a system as described herein, e.g., to record a medical image of a subject.

In some embodiments, the technology relates to a method of treating a patient. For example, in some embodiments, methods comprise recording a diagnostic image of a patient in a vertical position; and treating said patient in said vertical position. In some embodiments, the diagnostic image is a CT image, an MRI image, a PET image, a SPECT image, a photon counted computed tomography image, and/or a portal image or a scanogram. In some embodiments, methods of treating a patient further comprise recording a portal image prior to treating the patient. In some embodiments, methods comprise rotating the patient. In some embodiments, methods comprise providing a multi-axis medical imaging apparatus as described herein (e.g., for use in recording the diagnostic image and, optionally, for use in recording portal images). In some embodiments, methods comprise obtaining a diagnostic image of a patient in a vertical position (e.g., seated, seated and leaning backward, seated and leaning forward, standing, standing and leaning backward, standing and leaning forward, perched, kneeling, kneeling and leaning forward, or kneeling and leaning backward position); and treating a patient in the same vertical position. In some embodiments, methods comprise obtaining a diagnostic image of a patient in a vertical position (e.g., seated, seated and leaning backward, seated and leaning forward, standing, standing and leaning backward, standing and leaning forward, perched, kneeling, kneeling and leaning forward, or kneeling and leaning backward position); obtaining a portal image of said patient (e.g., to align the patient properly for treatment) prior to treatment; and treating a patient in the same vertical position. In some embodiments, treating the patient comprises moving (e.g., rotating) the patient and exposing the patient to treatment at a plurality of angles and/or positions on the patient body. In some embodiments, methods comprise imaging a patient in a vertical position (e.g., using the medical imaging apparatus as described herein) and treating the patient in a vertical position (e.g., with a radiotherapy apparatus). In some embodiments, methods comprise imaging a patient in a vertical position (e.g., a stationary vertical position) using a moving (e.g., translating and/or rotating) scanner (e.g., using a medical imaging apparatus as described herein) and treating the patient in a vertical position by rotating the patient (e.g., slowly rotating the patient) and exposing the patient to radiation from a stationary radiotherapy apparatus.

In particular embodiments, the technology relates to a multi-axis computerized tomography scanner that can produce CT scans of a patient in a vertical position. The technology can also produce CT scans of a patient in a horizontal position and other positions (e.g., a variety of postures including seated, seated and leaning backward, seated and leaning forward, standing, standing and leaning backward, standing and leaning forward, perched, kneeling, kneeling and leaning forward, or kneeling and leaning backward position, laying recumbent or prone, or other orthopedic positions). The technology is safer than conventional CT scanning apparatuses due to the mechanical design of the technology. Further, the technology is easier for a user to manipulate than a conventional CT scanning apparatus due to the mechanical design of the technology. For example, in some embodiments, the apparatus comprises a counterbalanced design that allows a user to manipulate and/or position (e.g., rotate, tilt, and/or translate) the scanner manually (e.g., with a force less than the force provided by an average human pushing and/or pulling with an arm and hand). For example, in some embodiments the apparatus comprises a counterbalanced design that allows a user to manipulate and position the scanner manually using a force that is approximately 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N). In some embodiments, the apparatus comprises a counterbalanced design that allows a user to manipulate and position the scanner manually with minimal assistance by a motor. In some embodiments, the apparatus comprises a counterbalanced design that allows a user to manipulate and position the scanner manually without assistance by a motor (e.g., in the event of a power outage). In some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor. Accordingly, the apparatus described herein moves with minimal force and thus does not injure a patient and/or cause damage to objects with which it may collide. In some embodiments, the apparatus comprises two counterbalanced components having a ratio of masses that is approximately 3:1, 2.5:1, 2:1, 1:1, 1:2, 1:2.5, or 1:3.

In some embodiments related to CT scanning, the technology provides to a multi-axis computerized tomography (CT) scanner (e.g., for obtaining a CT scan of a patient positioned in a vertical position). In some embodiments, the multi-axis CT scanner comprises a stanchion assembly (e.g., comprising a stanchion or a number of stanchions (e.g., comprising a stanchion or a number of stanchions and a base (e.g., comprising a stanchion; or a number of stanchions coupled to a base))); a gantry (e.g., comprising one gantry arm; or a first gantry arm and a second gantry arm) coupled to the stanchion assembly; and a scanner ring coupled to the gantry. In some embodiments, the scanner ring comprises an X-ray generator and an X-ray detector. In some embodiments, the gantry is rotatably coupled to the stanchion assembly. In some embodiments, the gantry is structured to rotate from 0-200 degrees (e.g., 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees) relative to the stanchion assembly. In some embodiments, the gantry is structured to rotate approximately 90 degrees (e.g., 80.0, 80.1, 80.2, 80.3, 80.4, 80.5, 80.6, 80.7, 80.8, 80.9, 81.0, 81.1, 81.2, 81.3, 81.4, 81.5, 81.6, 81.7, 81.8, 81.9, 82.0, 82.1, 82.2, 82.3, 82.4, 82.5, 82.6, 82.7, 82.8, 82.9, 83.0, 83.1, 83.2, 83.3, 83.4, 83.5, 83.6, 83.7, 83.8, 83.9, 84.0, 84.1, 84.2, 84.3, 84.4, 84.5, 84.6, 84.7, 84.8, 84.9, 85.0, 85.1, 85.2, 85.3, 85.4, 85.5, 85.6, 85.7, 85.8, 85.9, 86.0, 86.1, 86.2, 86.3, 86.4, 86.5, 86.6, 86.7, 86.8, 86.9, 87.0, 87.1, 87.2, 87.3, 87.4, 87.5, 87.6, 87.7, 87.8, 87.9, 88.0, 88.1, 88.2, 88.3, 88.4, 88.5, 88.6, 88.7, 88.8, 88.9, 89.0, 89.1, 89.2, 89.3, 89.4, 89.5, 89.6, 89.7, 89.8, 89.9, 90.0, 90.1, 90.2, 90.3, 90.4, 90.5, 90.6, 90.7, 90.8, 90.9, 91.0, 91.1, 91.2, 91.3, 91.4, 91.5, 91.6, 91.7, 91.8, 91.9, 92.0, 92.1, 92.2, 92.3, 92.4, 92.5, 92.6, 92.7, 92.8, 92.9, 93.0, 93.1, 93.2, 93.3, 93.4, 93.5, 93.6, 93.7, 93.8, 93.9, 94.0, 94.1, 94.2, 94.3, 94.4, 94.5, 94.6, 94.7, 94.8, 94.9, 95.0, 95.1, 95.2, 95.3, 95.4, 95.5, 95.6, 95.7, 95.8, 95.9, 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100.0 degrees) relative to the stanchion assembly.

In some embodiments, the gantry comprises a gantry arm rotatably coupled to a stanchion of the stanchion assembly. In some embodiments, the gantry comprises a first gantry arm rotatably coupled to a first stanchion of the stanchion assembly and the gantry comprises a second gantry arm rotatably coupled to a second stanchion of the stanchion assembly. In some embodiments, the stanchion assembly is translatably coupled to a horizontal planar base (e.g., a base on and/or in a floor). In some embodiments, the stanchion assembly is fixedly coupled to a horizontal planar base (e.g., a base on and/or in a floor). In some embodiments, the scanner ring is translatably coupled to the gantry. In some embodiments, the scanner ring is translatably coupled to a gantry arm of the gantry. In some embodiments, the scanner ring is translatably coupled to a first gantry arm of the gantry and the scanner ring is translatably coupled to a second gantry arm of the gantry. In some embodiments, the scanner ring is structured to translate along a long axis of the gantry arm. In some embodiments, the scanner ring is structured to translate along a long axis of the first gantry arm and along a long axis of the second gantry arm. In some embodiments, the scanner ring is structured to translate 0.20-2.00 m (e.g., 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, or 2.00 m) relative to the gantry.

In some embodiments, a counterbalanced assembly comprises the gantry and the scanner ring. In some embodiments, the counterbalanced assembly comprises the gantry, scanner ring, and a supplemental mass that provides a counterweight. In some embodiments, a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) rotates a counterbalanced assembly comprising the gantry and the scanner ring relative to the stanchion assembly. In some embodiments, a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) translates the scanner ring relative to the gantry. In some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor. In some embodiments, the apparatus comprises two counterbalanced components having a ratio of masses that is approximately 3:1, 2.5:1, 2:1, 1:1, 1:2, 1:2.5, or 1:3. In some embodiments, the scanner ring has a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms) and is counterbalanced by a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms).

In some embodiments, the stanchion assembly comprises a motor operatively engaged with the gantry. In some embodiments, the motor operatively engaged with the gantry is structured to rotate the gantry with respect to the stanchion assembly. In some embodiments, the motor operatively engaged with the gantry is structured to rotate the gantry from 0-200 degrees (e.g., 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees) relative to the stanchion assembly. In some embodiments, the motor operatively engaged with the gantry is structured to rotate the gantry approximately 90 degrees (e.g., 80.0, 80.1, 80.2, 80.3, 80.4, 80.5, 80.6, 80.7, 80.8, 80.9, 81.0, 81.1, 81.2, 81.3, 81.4, 81.5, 81.6, 81.7, 81.8, 81.9, 82.0, 82.1, 82.2, 82.3, 82.4, 82.5, 82.6, 82.7, 82.8, 82.9, 83.0, 83.1, 83.2, 83.3, 83.4, 83.5, 83.6, 83.7, 83.8, 83.9, 84.0, 84.1, 84.2, 84.3, 84.4, 84.5, 84.6, 84.7, 84.8, 84.9, 85.0, 85.1, 85.2, 85.3, 85.4, 85.5, 85.6, 85.7, 85.8, 85.9, 86.0, 86.1, 86.2, 86.3, 86.4, 86.5, 86.6, 86.7, 86.8, 86.9, 87.0, 87.1, 87.2, 87.3, 87.4, 87.5, 87.6, 87.7, 87.8, 87.9, 88.0, 88.1, 88.2, 88.3, 88.4, 88.5, 88.6, 88.7, 88.8, 88.9, 89.0, 89.1, 89.2, 89.3, 89.4, 89.5, 89.6, 89.7, 89.8, 89.9, 90.0, 90.1, 90.2, 90.3, 90.4, 90.5, 90.6, 90.7, 90.8, 90.9, 91.0, 91.1, 91.2, 91.3, 91.4, 91.5, 91.6, 91.7, 91.8, 91.9, 92.0, 92.1, 92.2, 92.3, 92.4, 92.5, 92.6, 92.7, 92.8, 92.9, 93.0, 93.1, 93.2, 93.3, 93.4, 93.5, 93.6, 93.7, 93.8, 93.9, 94.0, 94.1, 94.2, 94.3, 94.4, 94.5, 94.6, 94.7, 94.8, 94.9, 95.0, 95.1, 95.2, 95.3, 95.4, 95.5, 95.6, 95.7, 95.8, 95.9, 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100.0 degrees) relative to the stanchion assembly. In some embodiments, the gantry comprises a motor operatively engaged with the stanchion assembly. In some embodiments, the motor operatively engaged with the stanchion assembly is structured to rotate the gantry with respect to the stanchion assembly.

In some embodiments, the motor operatively engaged with the stanchion assembly is structured to rotate the gantry from 0-200 degrees (e.g., 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees) relative to the stanchion assembly. In some embodiments, the motor operatively engaged with the stanchion assembly is structured to rotate said gantry approximately 90 degrees (e.g., 80.0, 80.1, 80.2, 80.3, 80.4, 80.5, 80.6, 80.7, 80.8, 80.9, 81.0, 81.1, 81.2, 81.3, 81.4, 81.5, 81.6, 81.7, 81.8, 81.9, 82.0, 82.1, 82.2, 82.3, 82.4, 82.5, 82.6, 82.7, 82.8, 82.9, 83.0, 83.1, 83.2, 83.3, 83.4, 83.5, 83.6, 83.7, 83.8, 83.9, 84.0, 84.1, 84.2, 84.3, 84.4, 84.5, 84.6, 84.7, 84.8, 84.9, 85.0, 85.1, 85.2, 85.3, 85.4, 85.5, 85.6, 85.7, 85.8, 85.9, 86.0, 86.1, 86.2, 86.3, 86.4, 86.5, 86.6, 86.7, 86.8, 86.9, 87.0, 87.1, 87.2, 87.3, 87.4, 87.5, 87.6, 87.7, 87.8, 87.9, 88.0, 88.1, 88.2, 88.3, 88.4, 88.5, 88.6, 88.7, 88.8, 88.9, 89.0, 89.1, 89.2, 89.3, 89.4, 89.5, 89.6, 89.7, 89.8, 89.9, 90.0, 90.1, 90.2, 90.3, 90.4, 90.5, 90.6, 90.7, 90.8, 90.9, 91.0, 91.1, 91.2, 91.3, 91.4, 91.5, 91.6, 91.7, 91.8, 91.9, 92.0, 92.1, 92.2, 92.3, 92.4, 92.5, 92.6, 92.7, 92.8, 92.9, 93.0, 93.1, 93.2, 93.3, 93.4, 93.5, 93.6, 93.7, 93.8, 93.9, 94.0, 94.1, 94.2, 94.3, 94.4, 94.5, 94.6, 94.7, 94.8, 94.9, 95.0, 95.1, 95.2, 95.3, 95.4, 95.5, 95.6, 95.7, 95.8, 95.9, 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100.0 degrees) relative to the stanchion assembly.

In some embodiments, the gantry comprises a motor operatively engaged with the scanner ring. In some embodiments, the motor is coupled to a ball screw, a chain, or a belt. In some embodiments, the motor is structured to translate the scanner ring with respect to the gantry. In some embodiments, the motor is structured to translate the scanner ring 0.20-2.00 m (e.g., 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, or 2.00 m) with respect to the gantry. In some embodiments, the ball screw comprises a threaded shaft having a diameter of 15-100 mm (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm) In some embodiments, the motor is structured to translate the scanner ring 5-100 mm (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm) per revolution of the threaded shaft.

In some embodiments, the gantry comprises a supplemental mass component providing a counterweight for the scanner ring. In some embodiments, the gantry comprises a gantry arm comprising a supplemental mass component. In some embodiments, the gantry comprises a first gantry arm comprising a first portion of the supplemental mass component and a second gantry arm comprising a second portion of the supplemental mass component. In some embodiments, the multi-axis CT scanner comprises a motor structured to move the supplemental mass component and the scanner ring. In some embodiments, the two supplemental mass components are driven by the same motor. In some embodiments comprising two supplemental mass components driven by the same motor, the technology further comprises mechanical tensioning adjustment for each of the mechanical systems in the first and second gantry arms. In some embodiments, a first supplemental mass component is driven by a first motor and a second supplemental mass component is driven by a second motor. In some embodiments comprising a first supplemental mass component driven by a first motor and a second supplemental mass component driven by a second motor, the technology further comprises systems for calibration and synchronization of the movement of the first and second supplemental masses by the first and second motors. In some embodiments, the first gantry arm and the second gantry arm each comprises an encoder-feedback system to provide accurate positioning of the first and second supplemental masses. In some embodiments, the apparatus comprises two counterbalanced components having a ratio of masses that is approximately 3:1, 2.5:1, 2:1, 1:1, 1:2, 1:2.5, or 1:3. In some embodiments, the scanner ring has a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms) and is counterbalanced by a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms).

In some embodiments, the multi-axis CT scanner is structured to record a CT scan of a subject in a vertical, essentially vertical, or substantially vertical position. In some embodiments, the subject is in a seated, seated and leaning backward, seated and leaning forward, standing, standing and leaning backward, standing and leaning forward, perched, kneeling, kneeling and leaning forward, or kneeling and leaning backward position. In some embodiments, the scanner ring is structured to move from a first position over the head of the subject to a second position around the subject. In some embodiments, the scanner ring has an inner diameter of 20 cm or more (e.g., 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 cm). In some embodiments, the scanner ring measures approximately 33.5 cm (e.g., 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 cm) across, e.g., from the inner circumference (e.g., the inner bore) to the outer circumference.

In some embodiments, the technology provides methods of obtaining a CT scan of a subject. For example, in some embodiments, methods comprise providing a multi-axis computerized tomography (CT) scanner; positioning a subject; and recording a CT scan of the subject. In some embodiments, recording a CT scan of the subject comprises generating X-rays and detecting X-rays. In some embodiments, the multi-axis CT scanner comprises a stanchion assembly; a gantry coupled to the stanchion assembly; and a scanner ring coupled to the gantry. In some embodiments, positioning a subject comprises positioning the subject in a vertical position. In some embodiments, the vertical position is seated, seated and leaning backward, seated and leaning forward, standing, standing and leaning backward, standing and leaning forward, perched, kneeling, kneeling and leaning forward, or kneeling and leaning backward position. In some embodiments, positioning a subject comprises positioning a subject using a patient positioning system and/or patient support. In some embodiments, the patient positioning system and/or patient support is as described in Int'l Pat. App. Pub. No. WO 2019/056055, in U.S. Pat. App. Pub. No.

2020/0268327, and in and in U.S. Pat. App. Ser. No. 63/237,513, each of which is incorporated herein by reference.

In some embodiments, methods further comprise positioning the scanner ring around the subject. In some embodiments, positioning the scanner ring comprises rotating the gantry relative to the stanchion assembly and/or translating the scanner ring relative to the gantry. In some embodiments, rotating the gantry relative to the stanchion assembly comprises applying a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) to an assembly comprising the gantry and the scanner ring. In some embodiments, translating the scanner ring relative to the gantry comprises applying a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) to the scanner ring. In some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor. In some embodiments, rotating the gantry relative to the stanchion assembly comprises rotating the gantry 0-200 degrees (e.g., 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees) relative to the stanchion assembly. In some embodiments, rotating the gantry relative to the stanchion assembly comprises rotating the gantry approximately 90 degrees (e.g., 80.0, 80.1, 80.2, 80.3, 80.4, 80.5, 80.6, 80.7, 80.8, 80.9, 81.0, 81.1, 81.2, 81.3, 81.4, 81.5, 81.6, 81.7, 81.8, 81.9, 82.0, 82.1, 82.2, 82.3, 82.4, 82.5, 82.6, 82.7, 82.8, 82.9, 83.0, 83.1, 83.2, 83.3, 83.4, 83.5, 83.6, 83.7, 83.8, 83.9, 84.0, 84.1, 84.2, 84.3, 84.4, 84.5, 84.6, 84.7, 84.8, 84.9, 85.0, 85.1, 85.2, 85.3, 85.4, 85.5, 85.6, 85.7, 85.8, 85.9, 86.0, 86.1, 86.2, 86.3, 86.4, 86.5, 86.6, 86.7, 86.8, 86.9, 87.0, 87.1, 87.2, 87.3, 87.4, 87.5, 87.6, 87.7, 87.8, 87.9, 88.0, 88.1, 88.2, 88.3, 88.4, 88.5, 88.6, 88.7, 88.8, 88.9, 89.0, 89.1, 89.2, 89.3, 89.4, 89.5, 89.6, 89.7, 89.8, 89.9, 90.0, 90.1, 90.2, 90.3, 90.4, 90.5, 90.6, 90.7, 90.8, 90.9, 91.0, 91.1, 91.2, 91.3, 91.4, 91.5, 91.6, 91.7, 91.8, 91.9, 92.0, 92.1, 92.2, 92.3, 92.4, 92.5, 92.6, 92.7, 92.8, 92.9, 93.0, 93.1, 93.2, 93.3, 93.4, 93.5, 93.6, 93.7, 93.8, 93.9, 94.0, 94.1, 94.2, 94.3, 94.4, 94.5, 94.6, 94.7, 94.8, 94.9, 95.0, 95.1, 95.2, 95.3, 95.4, 95.5, 95.6, 95.7, 95.8, 95.9, 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9, or 100.0 degrees) relative to the stanchion assembly. In some embodiments, translating the scanner ring relative to the gantry comprises translating the scanner ring 0.2-2.0 m (e.g., 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, or 2.00 m) relative to the gantry. In some embodiments, the apparatus comprises two counterbalanced components having a ratio of masses that is approximately 3:1, 2.5:1, 2:1, 1:1, 1:2, 1:2.5, or 1:3. In some embodiments, the scanner ring has a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms) and is counterbalanced by a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms).

In some embodiments, methods further comprise verifying the configuration of the patient positioning system and/or patient support. In some embodiments, methods further comprise verifying the position of the subject on the patient positioning system and/or patient support. In some embodiments, verifying the configuration of the patient positioning system comprises imaging the patient positioning system and/or patient support to provide an image and/or model of the patient positioning system and/or patient support and comparing the image and/or model of the patient positioning system and/or patient support to a stored preset patient positioning system configuration and/or patient support configuration. In some embodiments, verifying the position of the subject comprises imaging the subject to provide an image and/or model of the subject and comparing the image and/or model of the subject to a stored preset subject patient position. In some embodiments, methods further comprise imaging the subject to monitor subject position and/or subject motion. In some embodiments, methods further comprise imaging the subject to identify the subject and/or to verify the identity of the subject. In some embodiments, methods further comprise translating the multi-axis CT scanner in the plane of a base movably coupled to the multi-axis CT scanner. In some embodiments, methods further comprise rotating the gantry relative to the stanchion assembly and/or translating the scanner ring relative to the gantry to provide an exit for the subject.

The technology provides embodiments of systems for recording a computerized tomography (CT) scan of a subject. In some embodiments, systems comprise a multi-axis CT scanner. In some embodiments, systems further comprise a vertically positioned subject. In some embodiments, the multi-axis CT scanner comprises a stanchion assembly; a gantry coupled to the stanchion assembly; and a scanner ring coupled to the gantry. In some embodiments, systems further comprise a patient positioning system and/or patient support. In some embodiments, the patient positioning system and/or patient support is as described in Int'l Pat. App. Pub. No. WO 2019/056055, in U.S. Pat. App. Pub. No. 2020/0268327, and in and in U.S. Pat. App. Ser. No. 63/237,513, each of which is incorporated herein by reference. In some embodiments, systems further comprise a vertically positioned subject and the patient positioning system and/or patient support maintains the subject of the vertically positioned subject. In some embodiments, systems further comprise an imaging subsystem (e.g., comprising a camera or a plurality of cameras). In some embodiments, the scanner ring comprises the camera or cameras. In some embodiments, the imaging subsystem is configured to monitor patient position and/or patient movement. In some embodiments, the imaging subsystem is configured to identify a patient and/or verify patient identity. In some embodiments, the imaging subsystem is configured to configure a patient positioning system and/or patient support and/or to confirm a configuration of a patient positioning system and/or of a patient support. In some embodiments, the imaging subsystem is configured to assist in controlling movement of the multi-axis CT scanner or a component thereof. In some embodiments, systems further comprise a light curtain subsystem. In some embodiments, the light curtain subsystem comprises a laser source. In some embodiments, the light curtain subsystem comprises a mirror. In some embodiments, the light curtain subsystem comprises a light detector. In some embodiments, the light curtain subsystem is configured to communicate an alert when a light curtain is penetrated. In some embodiments, the alert stops movement of the multi-axis CT scanner or a component thereof; and/or produces an audible and/or visible alert signal. In some embodiments, systems further comprise a controller configured to control movement of the multi-axis CT scanner or a component thereof; and/or to initiate and/or terminate a CT scan.

In some embodiments, the technology relates to uses of a multi-axis CT scanner to record a CT scan of a vertical subject. In some embodiments, the technology relates to use of a multi-axis CT scanner as described herein, e.g., to record a CT scan of a subject. In some embodiments, the technology relates to use of a system comprising a multi-axis computerized tomography (CT) scanner to record a CT scan of a vertical subject. In some embodiments, the technology relates to use of a system as described herein, e.g., to record a CT scan of a subject. In some embodiments, the technology relates to uses of a multi-axis CT scanner to record a portal image and/or a scanogram of a subject.

In some embodiments, the technology relates to a method of treating a patient. For example, in some embodiments, methods comprise recording a diagnostic image of a patient in a vertical position (e.g., seated, seated and leaning backward, seated and leaning forward, standing, standing and leaning backward, standing and leaning forward, perched, kneeling, kneeling and leaning forward, or kneeling and leaning backward position); and treating said patient in said vertical position. In some embodiments, the diagnostic image is a computerized tomography (CT) image. In some embodiments, methods of treating a patient further comprise recording a portal image prior to treating the patient. In some embodiments, methods comprise imaging (CT imaging) a patient in a vertical position (e.g., using the CT imaging apparatus as described herein) and treating the patient in a vertical position (e.g., with a radiotherapy apparatus). In some embodiments, methods comprise obtaining a diagnostic image (e.g., CT image) of a patient in a vertical position (e.g., seated, seated and leaning backward, seated and leaning forward, standing, standing and leaning backward, standing and leaning forward, perched, kneeling, kneeling and leaning forward, or kneeling and leaning backward position); obtaining a portal image of said patient (e.g., to align the patient properly for treatment) prior to treatment; and treating a patient in the same vertical position. In some embodiments, treating the patient comprises moving (e.g., rotating) the patient and exposing the patient to treatment at a plurality of angles and/or positions on the patient body. In some embodiments, methods comprise rotating the patient. For example, in some embodiments, methods comprise imaging (e.g., CT imaging) a patient in a vertical position (e.g., a stationary vertical position) using a moving (e.g., translating and/or rotating) scanner (e.g., using a medical imaging apparatus as described herein) and treating the patient in a vertical position by rotating the patient (e.g., slowly rotating the patient) and exposing the patient to radiation from a stationary radiotherapy apparatus. In some embodiments, methods comprise providing a multi-axis CT scanner as described herein (e.g., for use in recording the diagnostic image and, optionally, for use in recording the portal images).

In some embodiments, the technology provides a multi-axis computed tomography scanner that is a rapid multi-axis computed tomography (RMACT) scanner. For example, in some embodiments, the RMACT comprises a first stanchion, a second stanchion, a first gantry arm, a second gantry arm, and a scanner ring; a bottom bridge and a top bridge that connect the first gantry arm to the second gantry arm; and a patient support that is connected to the bottom bridge and the top bridge. In some embodiments, the RMACT scanner is structured to rotate said patient support between a vertical and a horizontal position. In some embodiments, the first stanchion comprises a motor operatively engaged with the first gantry arm and/or the second stanchion comprises a motor operatively engaged with the second gantry arm. In some embodiments, the first gantry arm comprises a motor operatively engaged with the first stanchion and/or the second gantry arm comprises a motor operatively engaged with the second stanchion. In some embodiments, the scanner ring comprises an x-ray source and an x-ray detector. In some embodiments, the scanner ring has an inner diameter of at least 20 cm. In some embodiments, the scanner ring has a mass of approximately 1000 kg. In some embodiments, the RMACT scanner draws approximately 300 mA of current, provides approximately 4 or more×40-cm scans in an hour, and provides a field of view of approximately 63 cm.

In related embodiments, the technology provides a method for obtaining medical images, the method comprising providing a rapid multi-axis computed tomography (RMACT) scanner comprising a first stanchion, a second stanchion, a first gantry arm, a second gantry arm, and a scanner ring; a bottom bridge and a top bridge that connect the first gantry arm to the second gantry arm; and a patient support that is connected to the bottom bridge and the top bridge; imaging a patient in a vertical position to obtain a first image; and imaging said patient in a horizontal position to obtain a second image. In some embodiments, methods comprise comparing the first image and the second image. In some embodiments, methods further comprise maintaining the patient on the patient support between imaging the patient in a vertical position and imaging the patient in a horizontal position. In some embodiments, methods comprise diagnosing the patient using said first image. In some embodiments, methods comprise planning a surgery or treatment using said second image. In some embodiments, methods comprise positioning said patient on said patient support. In some embodiments, methods comprise rotating the first gantry arm and the second gantry arm with respect to the first stanchion and the second stanchion prior to imaging the patient in a horizontal position.

In some embodiments, the technology provides a system comprising a rapid multi-axis computed tomography (RMACT) scanner comprising a first stanchion, a second stanchion, a first gantry arm, a second gantry arm, and a scanner ring; a bottom bridge and a top bridge that connect the first gantry arm to the second gantry arm; and a patient support that is connected to the bottom bridge and the top bridge; and a microprocessor configured to acquire a first image of a patient in a vertical position and to acquire a second image of the patient in a horizontal position. In some embodiments, the microprocessor is configured to rotate the gantry and/or to translate the scanner ring. In some embodiments, systems further comprise an x-ray source and the microprocessor is configured to activate and deactivate the x-ray source. In some embodiments, systems further comprise a software component that compares said first image and said second image.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

As shown in FIG. 4D, providing the gantry in a vertical position allows scanning a patient positioned in a vertical position.

Figure 1A:
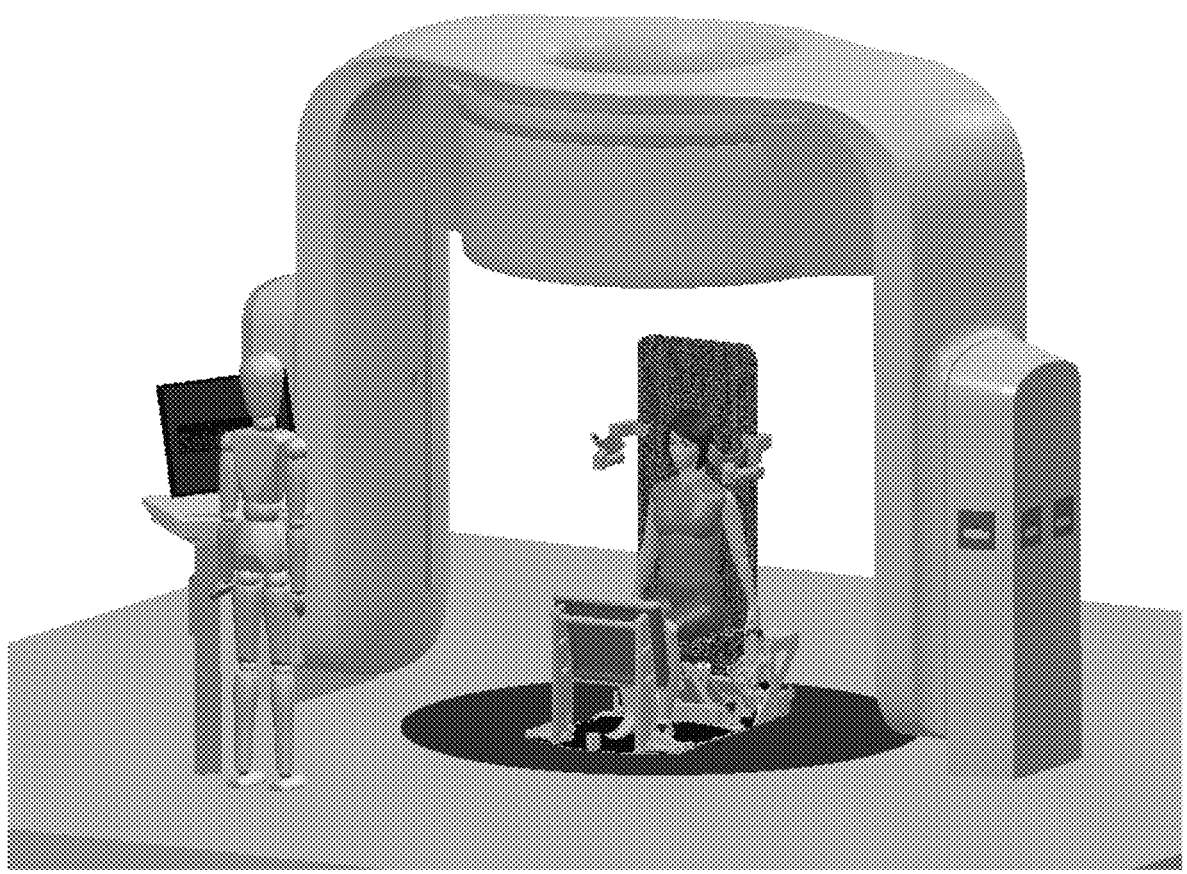
FIG. 1A is a drawing of an embodiment of a multi-axis CT scanner. A patient is shown sitting on a patient positioning system and a user is shown standing near a control unit.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to medical imaging and particularly, but not exclusively, to apparatuses, methods, and systems for radiology (e.g., using computerized tomography) and radiotherapy.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, disclosure of ranges includes disclosure of all values and further divided ranges within the entire range, including endpoints and sub-ranges given for the ranges.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

Although the terms "first", "second", "third", etc. may be used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

As used herein, the word "presence" or "absence" (or, alternatively, "present or "absent") is used in a relative sense to describe the amount or level of a particular entity (e.g., an analyte). For example, when an entity is said to be "present", it means the level or amount of this entity is above a pre-determined threshold; conversely, when an entity is said to be "absent", it means the level or amount of this entity is below a pre-determined threshold. The pre-determined threshold may be the threshold for detectability associated with the particular test used to detect the entity or any other threshold. When an entity is "detected" it is "present"; when an entity is "not detected" it is "absent". Further, a sample in which an analyte is "detected" or in which the analyte is "present" is a sample that is "positive" for the analyte. A sample in which an analyte is "not detected" or in which the analyte is "absent" is a sample that is "negative" for the analyte.

As used herein, an "increase" or a "decrease" refers to a detectable (e.g., measured) positive or negative change, respectively, in the value of a variable relative to a previously measured value of the variable, relative to a pre-established value, and/or relative to a value of a standard control. An increase is a positive change preferably at least 10%, more preferably 50%, still more preferably 2-fold, even more preferably at least 5-fold, and most preferably at least 10-fold relative to the previously measured value of the variable, the pre-established value, and/or the value of a standard control. Similarly, a decrease is a negative change preferably at least 10%, more preferably 50%, still more preferably at least 80%, and most preferably at least 90% of the previously measured value of the variable, the pre-established value, and/or the value of a standard control. Other terms indicating quantitative changes or differences, such as "more" or "less," are used herein in the same fashion as described above.

As used herein, a "system" refers to a plurality of real and/or abstract components operating together for a common purpose. In some embodiments, a "system" is an integrated assemblage of hardware and/or software components. In some embodiments, each component of the system interacts with one or more other components and/or is related to one or more other components. In some embodiments, a system refers to a combination of components and software for controlling, performing, and/or directing methods.

As used herein, the term "computed tomography" is abbreviated "CT" and refers both to tomographic and non-tomographic radiography. For instance, the term "CT" refers to numerous forms of CT, including but not limited to X-ray CT, positron emission tomography (PET), single-photon emission computed tomography (SPECT), and photon counting computed tomography. Generally, computed tomography (CT) comprises use of an X-ray source and a detector that rotates around a patient and subsequent reconstruction of images into different planes. Currents for X-rays used in CT describe the current flow from a cathode to an anode and are typically measured in milliamperes (mA).

As used herein, the term "structured to [verb]" means that the identified element or assembly has a structure that is shaped, sized, disposed, coupled, and/or configured to perform the identified verb. For example, a member that is "structured to move" is movably coupled to another element and includes elements that cause the member to move or the member is otherwise configured to move in response to other elements or assemblies. As such, as used herein, "structured to [verb]" recites structure and not function. Further, as used herein, "structured to [verb]" means that the identified element or assembly is intended to, and is designed to, perform the identified verb.

As used herein, the term "associated" means that the elements are part of the same assembly and/or operate together or act upon/with each other in some manner. For example, an automobile has four tires and four hub caps. While all the elements are coupled as part of the automobile, it is understood that each hubcap is "associated" with a specific tire.

As used herein, the term "coupled" refers to two or more components that are secured, by any suitable means, together. Accordingly, in some embodiments, the statement that two or more parts or components are "coupled" shall mean that the parts are joined or operate together either directly or indirectly, e.g., through one or more intermediate parts or components. As used herein, "directly coupled" means that two elements are directly in contact with each other. As used herein, "fixedly coupled" or "fixed" means that two components are coupled so as to move as one while maintaining a constant orientation relative to each other. Accordingly, when two elements are coupled, all portions of those elements are coupled. A description, however, of a specific portion of a first element being coupled to a second element, e.g., an axle first end being coupled to a first wheel, means that the specific portion of the first element is disposed closer to the second element than the other portions thereof. Further, an object resting on another object held in place only by gravity is not "coupled" to the lower object unless the upper object is otherwise maintained substantially in place. That is, for example, a book on a table is not coupled thereto, but a book glued to a table is coupled thereto.

As used herein, the term "removably coupled" or "temporarily coupled" means that one component is coupled with another component in an essentially temporary manner. That is, the two components are coupled in such a way that the joining or separation of the components is easy and does not damage the components. Accordingly, "removably coupled" components may be readily uncoupled and recoupled without damage to the components.

As used herein, the term "operatively coupled" means that a number of elements or assemblies, each of which is movable between a first position and a second position, or a first configuration and a second configuration, are coupled so that as the first element moves from one position/configuration to the other, the second element moves between positions/configurations as well. It is noted that a first element may be "operatively coupled" to another without the opposite being true.

As used herein, the term "rotatably coupled" refers to two or more components that are coupled in a manner such that at least one of the components is rotatable with respect to the other.

As used herein, the term "translatably coupled" refers to two or more components that are coupled in a manner such that at least one of the components is translatable with respect to the other.

As used herein, the term "temporarily disposed" means that a first element or assembly is resting on a second element or assembly in a manner that allows the first element/assembly to be moved without having to decouple or otherwise manipulate the first element. For example, a book simply resting on a table, e.g., the book is not glued or fastened to the table, is "temporarily disposed" on the table.

As used herein, the term "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are to fit "snugly" together. In that situation, the difference between the size of the components is even smaller whereby the amount of friction increases. If the element defining the opening and/or the component inserted into the opening are made from a deformable or compressible material, the opening may even be slightly smaller than the component being inserted into the opening. With regard to surfaces, shapes, and lines, two, or more, "corresponding" surfaces, shapes, or lines have generally the same size, shape, and contours.

As used herein, a "path of travel" or "path," when used in association with an element that moves, includes the space an element moves through when in motion. As such, any element that moves inherently has a "path of travel" or "path."

As used herein, the statement that two or more parts or components "engage" one another shall mean that the elements exert a force or bias against one another either directly or through one or more intermediate elements or components. Further, as used herein with regard to moving parts, a moving part may "engage" another element during the motion from one position to another and/or may "engage" another element once in the described position. Thus, it is understood that the statements, "when element A moves to element A first position, element A engages element B," and "when element A is in element A first position, element A engages element B" are equivalent statements and mean that element A either engages element B while moving to element A first position and/or element A engages element B while in element A first position.

As used herein, the term "operatively engage" means "engage and move." That is, "operatively engage" when used in relation to a first component that is structured to move a movable or rotatable second component means that the first component applies a force sufficient to cause the second component to move. For example, a screwdriver may be placed into contact with a screw. When no force is applied to the screwdriver, the screwdriver is merely "coupled" to the screw. If an axial force is applied to the screwdriver, the screwdriver is pressed against the screw and "engages" the screw. However, when a rotational force is applied to the screwdriver, the screwdriver "operatively engages" the screw and causes the screw to rotate. Further, with electronic components, "operatively engage" means that one component controls another component by a control signal or current.

As used herein, the term "number" shall mean one or an integer greater than one (e.g., a plurality).

As used herein, in the phrase "[x] moves between its first position and second position," or, "[y] is structured to move [x] between its first position and second position," "[x]" is the name of an element or assembly. Further, when [x] is an element or assembly that moves between a number of positions, the pronoun "its" means "[x]," i.e., the named element or assembly that precedes the pronoun "its."

As used herein, a "radial side/surface" for a circular or cylindrical body is a side/surface that extends about, or encircles, the center thereof or a height line passing through the center thereof. As used herein, an "axial side/surface" for a circular or cylindrical body is a side that extends in a plane extending generally perpendicular to a height line passing through the center. That is, generally, for a cylindrical soup can, the "radial side/surface" is the generally circular sidewall and the "axial side(s)/surface(s)" are the top and bottom of the soup can.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human. For instance, the term "subject" or "patient" refers to organisms including, but not limited to, humans and veterinary animals (dogs, cats, horses, pigs, cattle, sheep, goats, and the like). In the context of the technology, the term "subject" or "patient" generally refers to an individual who will be subject to a CT scan to diagnose a disease or injury; and/or to prepare for a treatment.

As used herein, a "diagnostic" test includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject having a cancer or the likelihood that such a subject will respond favorably to a compound (e.g., a pharmaceutical, e.g., a drug) or other treatment.

As used herein, the term "condition" refers generally to a disease, malady, injury, event, or change in health status.

As used herein, the term "treating" or "treatment" with respect to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. In some embodiments, "treatment" comprises exposing a patient or a portion thereof (e.g., a tissue, organ, body part, or other localize region of a patient body) to radiation (e.g., electromagnetic radiation, ionizing radiation).

As used herein, the term "perched position" refers to a patient in a generally standing position with a torso angled posteriorly with respect to a vertical axis, optionally also having bent knees.

DESCRIPTION

The technology provided herein relates to a medical imaging apparatus. While described in some embodiments for computed tomography (CT), the technology is not limited to use with CT and finds use for other medical imaging technologies such as, e.g., radiography, fluoroscopy, MRI, SPECT, PET, photon counting computed tomography, and portal imaging (e.g., prior to a treatment) or scanned projection radiography. Computed tomography (CT), and in particular computer X-ray tomography, is an imaging technique that generates cross-sectional images of a patient by mathematically combining multiple X-ray images (projections) taken along the plane of the cross-section at a range of angles. In conventional CT, generating a tomographic image involves providing a projection set of multiple projections over at least 180 degrees and preferably 360 degrees of angular range about the patient. The patient is typically moved through a gantry holding an X-ray source and X-ray detector that turn in coordinated opposition about the patient to acquire each X-ray projection set, either continuously during the orbital motion (helical scanning) or step-wise in between orbits (step scanning) to obtain X-ray projection sets for adjacent cross-sectional images that together describe a volume of tissue. Movement of the patient is conventional CT is provided by supporting a horizontal patient on a horizontally extending radio translucent table that is moved through the gantry.

In cone beam CT, the X-rays are generated in a cone shaped beam and measured with an area detector array. In fan beam CT, the X-rays used to acquire the projections are collimated to a thin fan beam lying within the plane of the cross-section and received by a narrow linear detector. The combination of the X-rays to a fan beam permits data acquisition with substantially reduced X-ray scatter and improved image fidelity in the cross-sectional or tomographic image. The fan beams generate cross-sectional images of "slices" that may be as thin as a few millimeters. Generating tomographic data for a significant volume of tissue in a reasonable time therefore requires rapid movement of the X-ray tube and detector in many orbits. For this reason, CT acquisition normally uses a specialized gantry system having a housing internally supporting the X-ray tube and detector on a bearing system for continuous or near-continuous rotation about an unobstructed bore volume. This gantry system is readily distinguishable from typical C-arm systems used, for example, for general-purpose X-ray imaging and cone-beam CT where only one or few orbits of the patient is/are performed.

CT imaging of some patients may preferably be performed with the patient in a vertical position (e.g., a sitting, kneeling, standing, perched, and/or reclining position (e.g., seated, seated and leaning backward, seated and leaning forward, standing, standing and leaning backward, standing and leaning forward, kneeling, kneeling and leaning forward, or kneeling and leaning backward)). For example, a lung cancer patient undergoing thoracic radiotherapy may prefer to be in a standing position so as not to promote the coughing that often accompanies this treatment. Some medical conditions such as vertebral fractures may be more evident in a weight-bearing standing position. Accordingly, CT scanners that record CT scans of patients in a vertical position would benefit medical diagnosis and treatment. Further, a CT scanner that is capable of scanning on multiple axes, e.g., to scan patients in a vertical position, patients positioned in a conventional horizontal position, and in other positions, would expand the use scenarios of the CT scanner to address more diseases, injuries, and maladies, and to improve the cost effectiveness of the CT scanner.

Apparatuses

Accordingly, in some embodiments, the technology relates to a multi-axis medical imaging apparatus (e.g., a multi-axis computed tomography scanner or a rapid multi-axis computed tomography (RMACT) scanner). In some embodiments, the medical imaging apparatus is a computerized tomography (CT) apparatus, a magnetic resonance imaging (MRI) apparatus, a positron emission tomography (PET) apparatus, a single-photon emission computerized tomography (SPECT) apparatus, a photon counting computed tomography apparatus, or a portal imaging or scan projection radiography apparatus. While the technology is described for exemplary embodiments wherein the medical imaging apparatus is a computerized tomography (CT) apparatus, the technology is not limited to a CT scanning apparatus and embodiments are to be understood to include other types of medical imaging apparatuses, methods, and systems.

In some embodiments, e.g., as shown in FIG. 1A, the technology provides a multi-axis CT scanner. In some embodiments, the multi-axis CT scanner is used by a user to obtain a CT scan of a patient. In some embodiments, the patient is positioned vertically. In some embodiments, a patient that is positioned vertically is positioned with a slight recline (e.g., within 20 degrees of vertical (e.g., within 5, 6, 7, 8, 9, 10, 11, 12, 13, 14, 15, 16, 17, 18, 19, or 20 degrees)) so that the patient may lean against a surface for support to provide increased immobilization of the patient and to limit motion of the patient. In some embodiments, the patient is positioned using a patient positioning system and/or patient support and the user operates a control unit. In some embodiments, the patient positioning system and/or patient support is as described in Int'l Pat. App. Pub. No. WO 2019/056055, in U.S. Pat. App. Pub. No. 2020/0268327, and in and in U.S. Pat. App. Ser. No. 63/237,513, each of which is incorporated herein by reference.

Figure 1B:
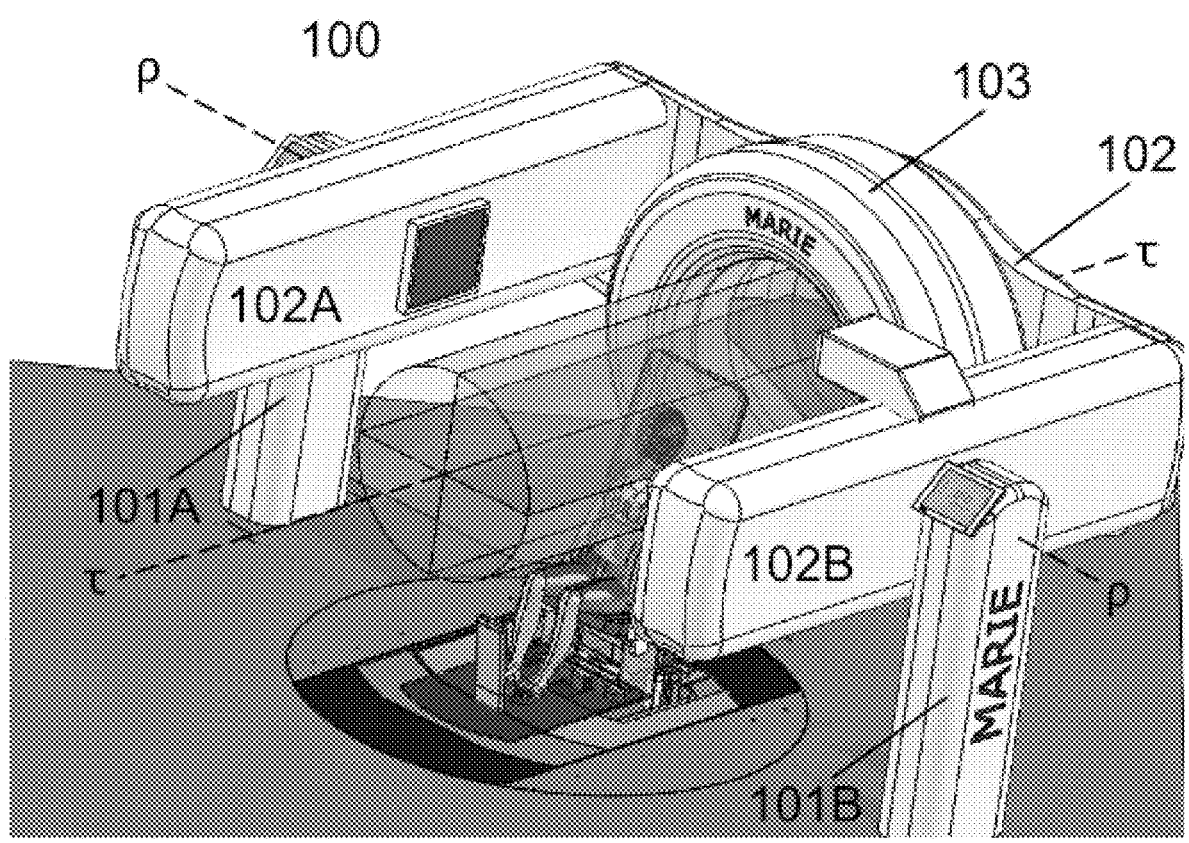
FIG. 1B is a drawing of an embodiment of a multi-axis CT scanner. The multi-axis CT scanner 100 comprises a first stanchion 101A, a second stanchion 101B, a gantry 102 comprising a first gantry arm 102A and a second gantry arm 102B, and a scanner ring 103. The gantry 102 rotates (and gantry arms 102A and 103B rotate) about an axis of rotation ρ relative to the first stanchion 101A and the second stanchion 101B. The scanner ring 103 is structured to move along an axis of translation (τ) that is parallel (e.g., substantially and/or essentially parallel) to the long dimension of the gantry arms 102A and 102B. The axis of translation τ is also perpendicular (e.g., substantially and/or essentially perpendicular) to the axis of rotation ρ. A patient is shown seated in a patient positioning system.
Figure 4A:
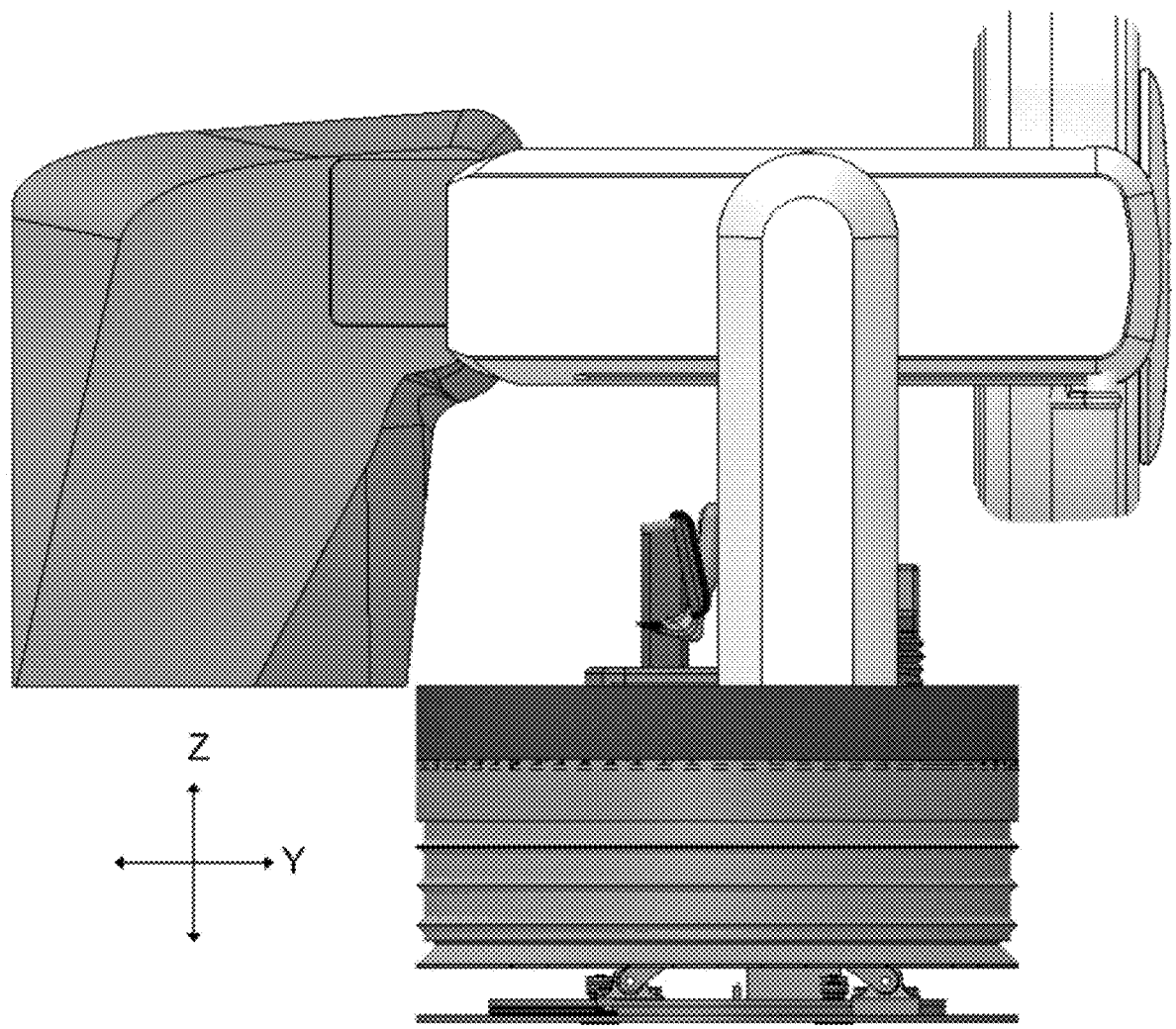
FIG. 4A is a drawing shown in a side view of a multi-axis CT scanner with the gantry in a horizontal position. The Z-axis and the Y-axis of a three-dimensional coordinate system are shown for reference.
Figure 4B:
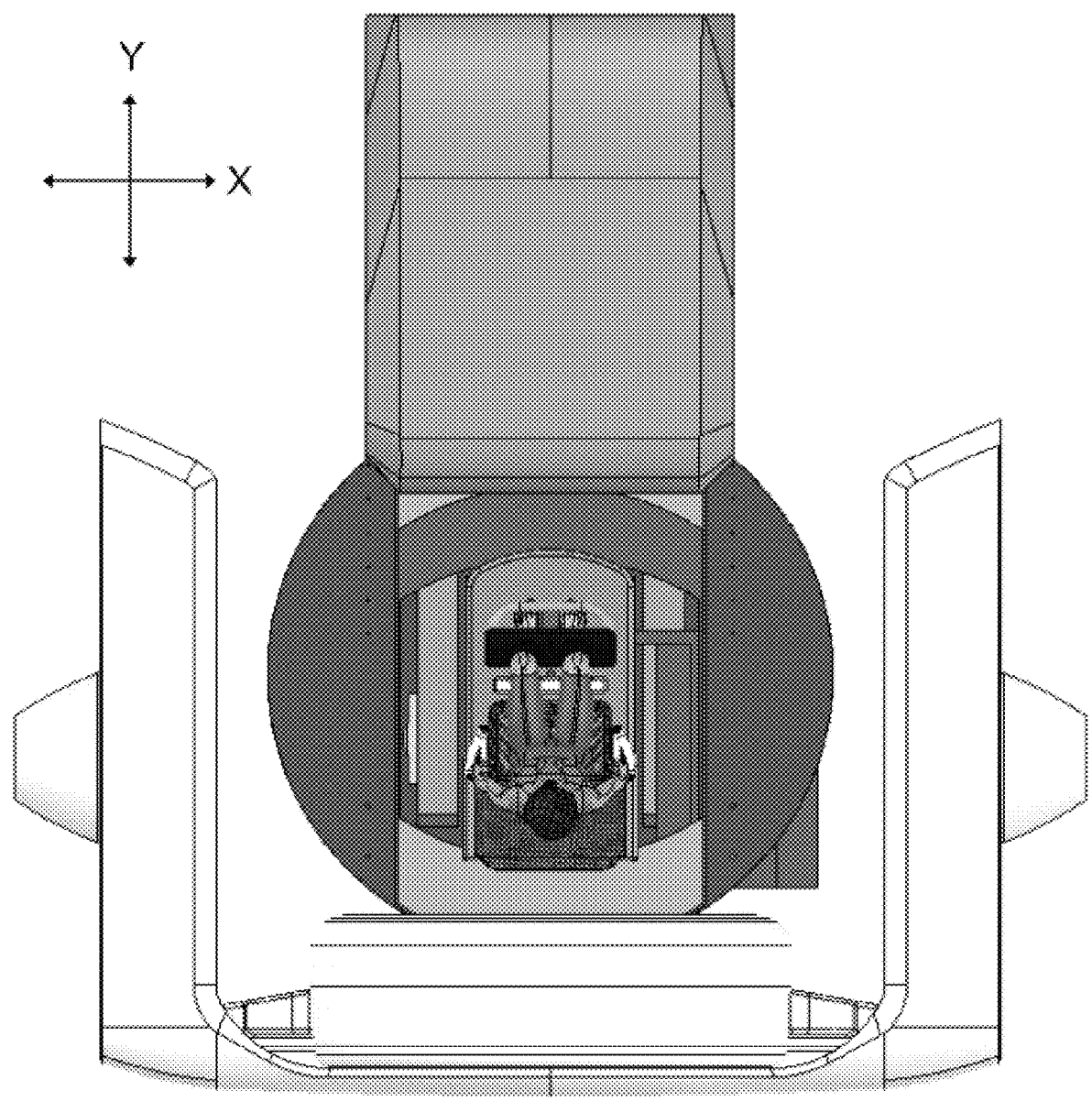
FIG. 4B is a drawing shown in a top view of a multi-axis CT scanner with the gantry in a horizontal position. The X-axis and the Y-axis of a three-dimensional coordinate system are shown for reference. In some embodiments, methods comprise translating the multi-axis CT scanner (e.g., by translating one or both stanchions) in the X-Y plane (e.g., in the plane of the floor), e.g., to position the scanner ring with respect to a patient and/or a region of interest of a patient.

In some embodiments, e.g., as shown in FIG. 1B, the technology provides a multi-axis CT scanner 100 comprising stanchions (e.g., a first stanchion 101A and/or a second stanchion 101B). In some embodiments, the stanchions are mounted into the floor of a room in which the multi-axis CT scanner is located. In some embodiments, the stanchions can be moved in the plane of the floor (e.g., to change their X-Y position in the X-Y plane as shown in FIG. 4B), e.g., to move the multi-axis CT scanner into a position to obtain a CT scan of a patient (see, e.g., FIG. 4B). In some embodiments, motors (e.g., motors structured to rotate the gantry 102 relative to the stanchions 101A and 101B), electrical supply wires, and/or communications cables are provided within one or both stanchions. Further, in some embodiments, the multi-axis CT scanner 100 comprises a gantry 102 (e.g., a "U-shaped" gantry). In some embodiments, the gantry 102 comprises a first gantry arm 102A and a second gantry arm 102B. In some embodiments, the gantry 102 rotates around an axis (e.g., axis ρ) relative to the first stanchion 101A and the second stanchion 101B, e.g., the first gantry arm 102A and the second gantry arm 102B rotate around an axis (e.g., axis ρ) relative to the first stanchion 101A and the second stanchion 101B. In some embodiments, motors (e.g., motors structured to rotate the gantry 102 relative to the stanchions 101A and 101B), electrical supply wires, and/or communications cables are provided within one or both gantry arms 102A and/or 102B.

Further, in some embodiments, the multi-axis CT scanner comprises a scanner ring 103 (e.g., a toroidal housing that comprises (e.g., encloses) the X-ray source and X-ray detector). In some embodiments, rotating the gantry 102 causes the scanner ring 103 to revolve on an arc around axis ρ, e.g., to move it from a first position to a second position. In some embodiments, the first position of the scanner ring 103 allows a patient to access and/or to exit a patient positioning system and/or patient support. In some embodiments, the second position of the scanner ring 103 is a position used to obtain a CT scan of a patient. In some embodiments, the second position of the scanner ring 103 is over the head of the patient. In some embodiments, the inner diameter of the scanner ring is 20 cm or more (e.g., 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 cm).

In some embodiments, the technology provides an advantage of comprising a scanner ring that is smaller and/or has less mass than conventional scanner rings. For example, in some embodiments, the scanner ring has a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms).

In some embodiments, a smaller and/or less massive scanner ring further contributes to the manipulability of the multi-axis CT scanner technology, e.g., because the gantry and/or scanner ring is easier to move and/or manipulate than in conventional technologies. In some embodiments, a smaller and/or less massive scanner ring further contributes to the advantage of the components of the multi-axis CT scanner being moved with minimal and/or decreased force provided by a user and/or a motor to move the multi-axis CT scanner ring technology, e.g., because the gantry and/or scanner ring is moved and/or manipulated with decreased and/or minimal force relative to previous technologies. In some embodiments, the smaller scanner ring comprises a rotating anode tube that draws 300 mA (e.g., 250, 260, 270, 280, 290, 300, 310, 320, 330, 340, or 350 mA) and provides approximately 4 and/or at least 4 (e.g., 3, 4, 5, 6, 7, 8 or more)×40-cm (e.g., 35.0, 35.1, 35.2, 35.3, 35.4, 35.5, 35.6, 35.7, 35.8, 35.9, 36.0, 36.1, 36.2, 36.3, 36.4, 36.5, 36.6, 36.7, 36.8, 36.9, 37.0, 37.1, 37.2, 37.3, 37.4, 37.5, 37.6, 37.7, 37.8, 37.9, 38.0, 38.1, 38.2, 38.3, 38.4, 38.5, 38.6, 38.7, 38.8, 38.9, 39.0, 39.1, 39.2, 39.3, 39.4, 39.5, 39.6, 39.7, 39.8, 39.9, 40.0, 40.1, 40.2, 40.3, 40.4, 40.5, 40.6, 40.7, 40.8, 40.9, 41.0, 41.1, 41.2, 41.3, 41.4, 41.5, 41.6, 41.7, 41.8, 41.9, 42.0, 42.1, 42.2, 42.3, 42.4, 42.5, 42.6, 42.7, 42.8, 42.9, 43.0, 43.1, 43.2, 43.3, 43.4, 43.5, 43.6, 43.7, 43.8, 43.9, 44.0, 44.1, 44.2, 44.3, 44.4, 44.5, 44.6, 44.7, 44.8, 44.9, or 45.0-cm) scans in an hour with a field of view of approximately 63 cm (e.g., 58.0, 58.1, 58.2, 58.3, 58.4, 58.5, 58.6, 58.7, 58.8, 58.9, 59.0, 59.1, 59.2, 59.3, 59.4, 59.5, 59.6, 59.7, 59.8, 59.9, 60.0, 60.1, 60.2, 60.3, 60.4, 60.5, 60.6, 60.7, 60.8, 60.9, 61.0, 61.1, 61.2, 61.3, 61.4, 61.5, 61.6, 61.7, 61.8, 61.9, 62.0, 62.1, 62.2, 62.3, 62.4, 62.5, 62.6, 62.7, 62.8, 62.9, 63.0, 63.1, 63.2, 63.3, 63.4, 63.5, 63.6, 63.7, 63.8, 63.9, 64.0, 64.1, 64.2, 64.3, 64.4, 64.5, 64.6, 64.7, 64.8, 64.9, or 65.0 cm), while also being smaller and comprising less mass than previous scanner rings. For example, in some embodiments, the scanner ring measures approximately 33.5 cm (e.g., 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 cm) across, e.g., from the inner circumference (e.g., the inner bore) to the outer circumference.

In some embodiments, the scanner ring comprises a source and a detector for CT, MRI, PET, SPECT, photon counting computed tomography, or portal imaging. Accordingly, in some embodiments, the scanner ring comprises a medical imaging source (e.g., electromagnetic radiation source, X-ray source, gamma ray source, radio wave source, photon source, proton source, positron source, gamma ray source (e.g., gamma rays from a positron source)) and a medical imaging detector (e.g., electromagnetic radiation detector, X-ray detector, photon detector, gamma ray detector), e.g., for one or more of these imaging modes.

Further, in some embodiments, the scanner ring 103 is structured to translate along an axis substantially parallel to the first gantry arm 102A and the second gantry arm 102B, e.g., along axis T as shown in FIG. 1B. In some embodiments, the scanner ring translates along a vertical (e.g., substantially and/or essentially vertical) axis, e.g., to obtain a CT scan of a patient in a vertical position. In some embodiments, the scanner ring translates along a horizontal (e.g., substantially and/or essentially horizontal) axis, e.g., to obtain a CT scan of a patient in a horizontal position. In some embodiments related to scanning a horizontal patient, the scanner ring 103 moves into scanning position to scan a stationary patient in contrast to conventional technologies in which a patient is moved into scanning position and the scanner is stationary. The present technology thus provides advantages over conventional technologies for obtaining CT scans of horizontal patients. In some embodiments, motors (e.g., motors structured to translate the scanner ring 103 relative to the gantry 102), electrical supply wires, and/or communications cables are provided within one or both gantry arms 102A and/or 102B. In some embodiments, the motor is coupled to a belt, chain, or a ball screw (e.g., comprising a threaded shaft and a ball assembly operationally attached to the scanner ring). In some embodiments, the ball screw comprises a threaded shaft having a diameter of 15-100 mm (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm). In some embodiments, the ball screw provides a translation of the scanner ring of 5-100 mm/revolution (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm/revolution). In some embodiments, the motor drives a belt operationally attached to the scanner ring.

In some embodiments, the scanner ring 103 comprises (e.g., encloses) an X-ray generator that moves within the scanner ring 103 and thus revolves around the patient. In some embodiments, the scanner ring 103 comprises (e.g., encloses) one or more X-ray detectors. In some embodiments, the X-ray generator produces a fan beam of X-rays in a plane extending across the scanner ring. In some embodiments, the X-ray detector comprises an arcuate detector array within said plane at a substantially constant radius from the X-ray generator source. In some embodiments, multiple stationary X-ray detectors are positioned around the circumference of the scanner ring 103 such that an X-ray detector is always on the opposite side of the from the X-ray source moving within the scanner ring 103. In some embodiments, the scanner ring 103 comprises a moving X-ray detector that moves within the scanner ring 103 and is positioned opposite the moving X-ray generator, e.g., the X-ray generator and the X-ray detector move in concert so that the X-ray generator and the X-ray detector are on opposite sides of the scanner ring 103. In some embodiments, the scanner ring 103 is translated into position and is stationary while the X-ray generator and X-ray detector move around the circumference of the scanner ring 103. In some embodiments, the scanner ring 103 is translated one or more times and/or is translated continuously while the X-ray generator and the X-ray detector move around the circumference of the scanner ring 103 (e.g., to provide a helical scan). In some embodiments, the multi-axis CT scanner comprises a slip ring to transmit electrical power from the scanner ring 103 to the X-ray generator and X-ray detector and to carry communications signals between the scanner ring 103 and the X-ray generator and X-ray detector.

In some embodiments, the multi-axis imaging apparatus finds use in providing (e.g., recording, acquiring) a portal image. In some embodiments, the multi-axis imaging apparatus finds use in scout scanning. In some embodiments in which the multi-axis imaging apparatus is used for portal imaging and/or scout scanning, the X-ray generator and the X-ray detector do not move (e.g., they do not rotate). In some embodiments, the scanner ring is stationary for portal imaging. In some embodiments, the scanner ring translates for scout scanning.

Figure 9:
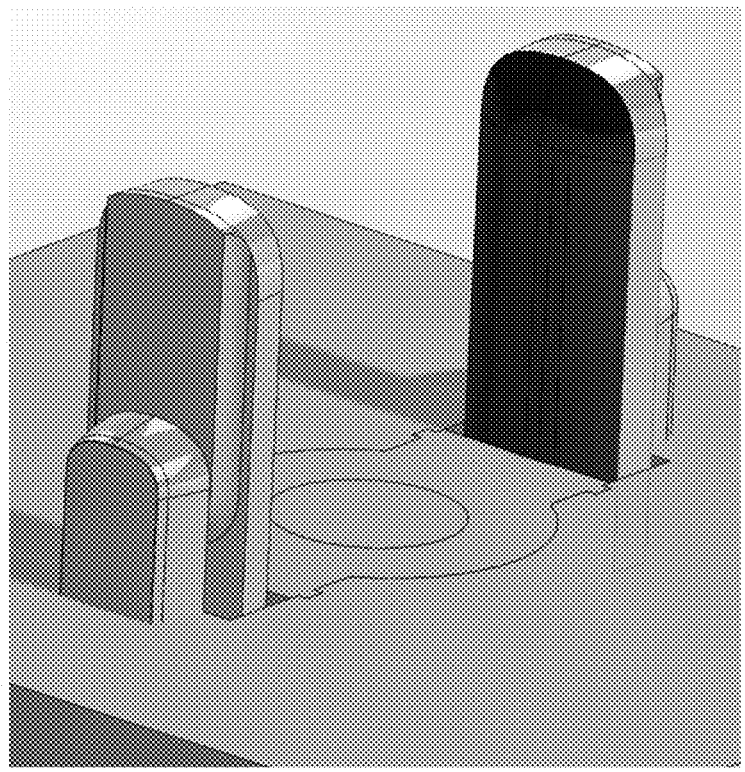
FIG. 9 is a drawing of an embodiment of the technology wherein the scanner ring moves upward from a position in the floor.
Figure 10:
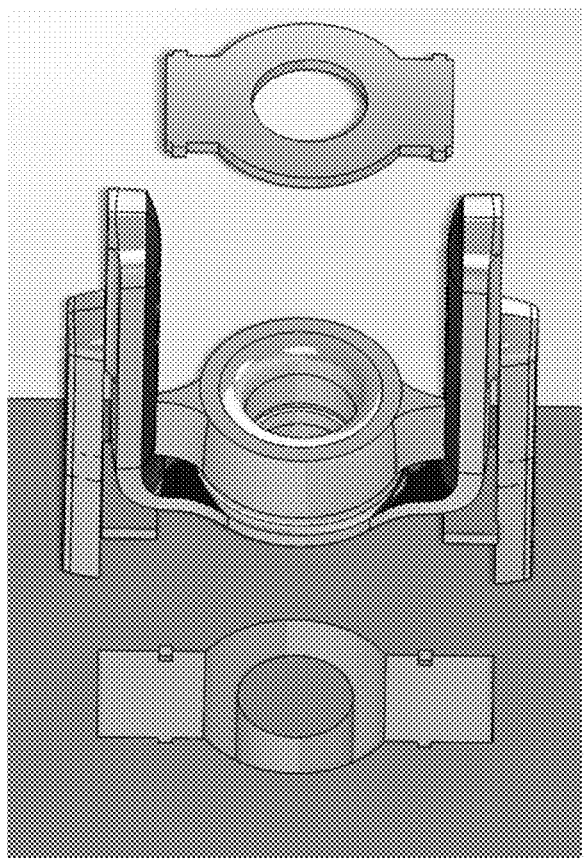
FIG. 10 is a drawing of an embodiment of the technology comprising a pit, a multi-axis CT scanner that moves upward from a position in the floor (e.g., from the pit), and a floor insert piece.
Figure 11:
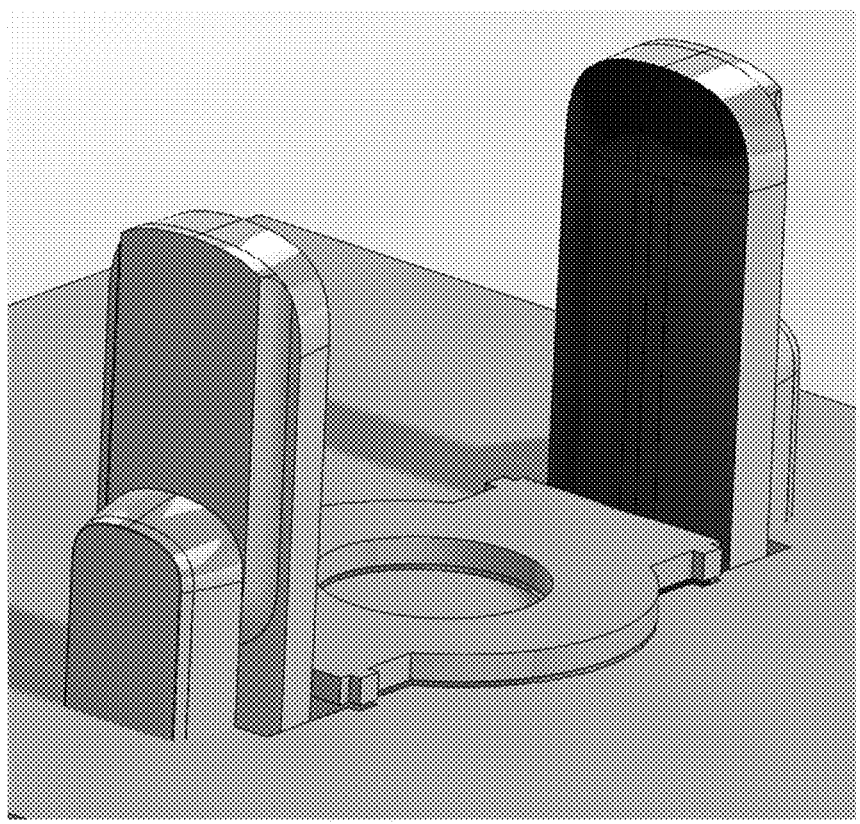
FIG. 11 is a drawing of an embodiment of the technology showing the floor insert piece being raised to allow the multi-axis CT scanner to move upward out of the floor (e.g., from the pit).
Figure 12:
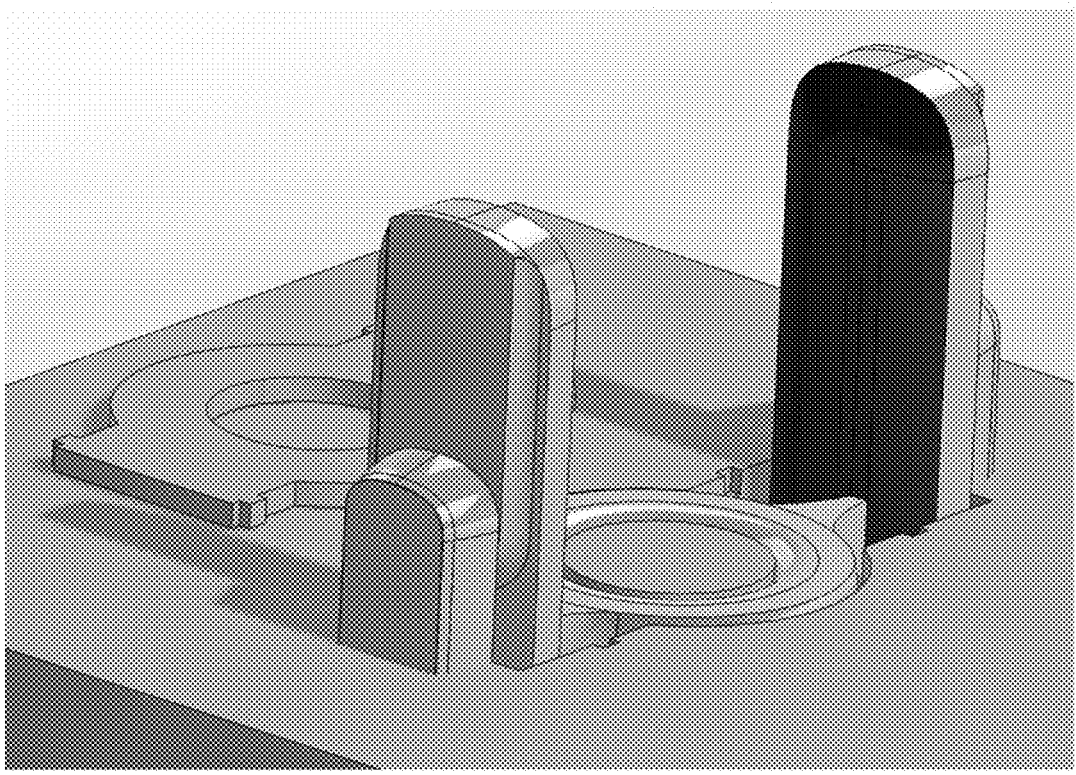
FIG. 12 is a drawing of an embodiment of the technology showing the floor insert piece having been moved to allow the multi-axis CT scanner to move upward out of the floor (e.g., from the pit).
Figure 13:
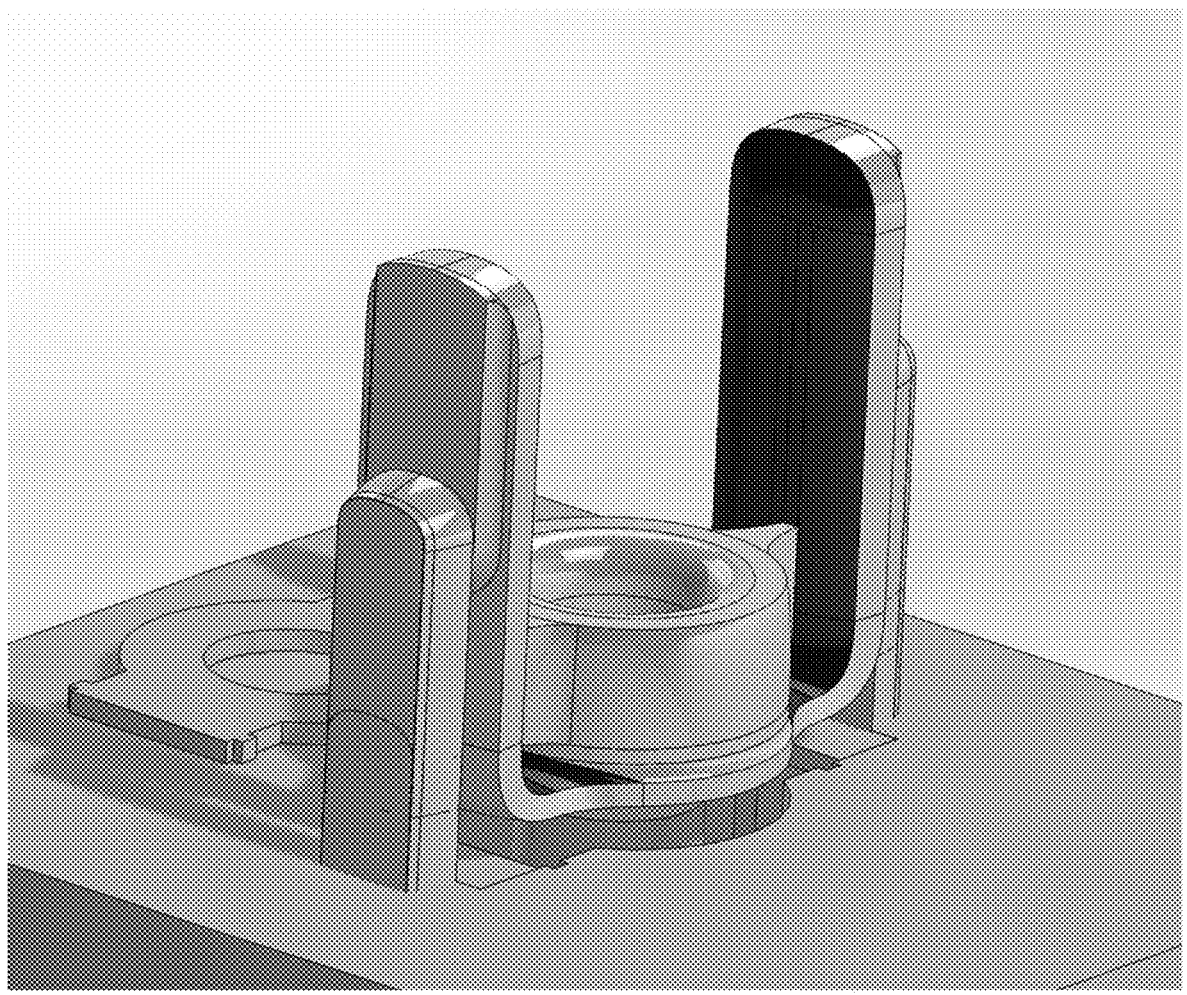
FIG. 13 is a drawing of an embodiment of the technology showing the multi-axis CT scanner moving upward out of the floor (e.g., from the pit) into a vertical position (e.g., to scan a patient in a vertical position or to scan a portion of a patient in a vertical position).
Figure 14:
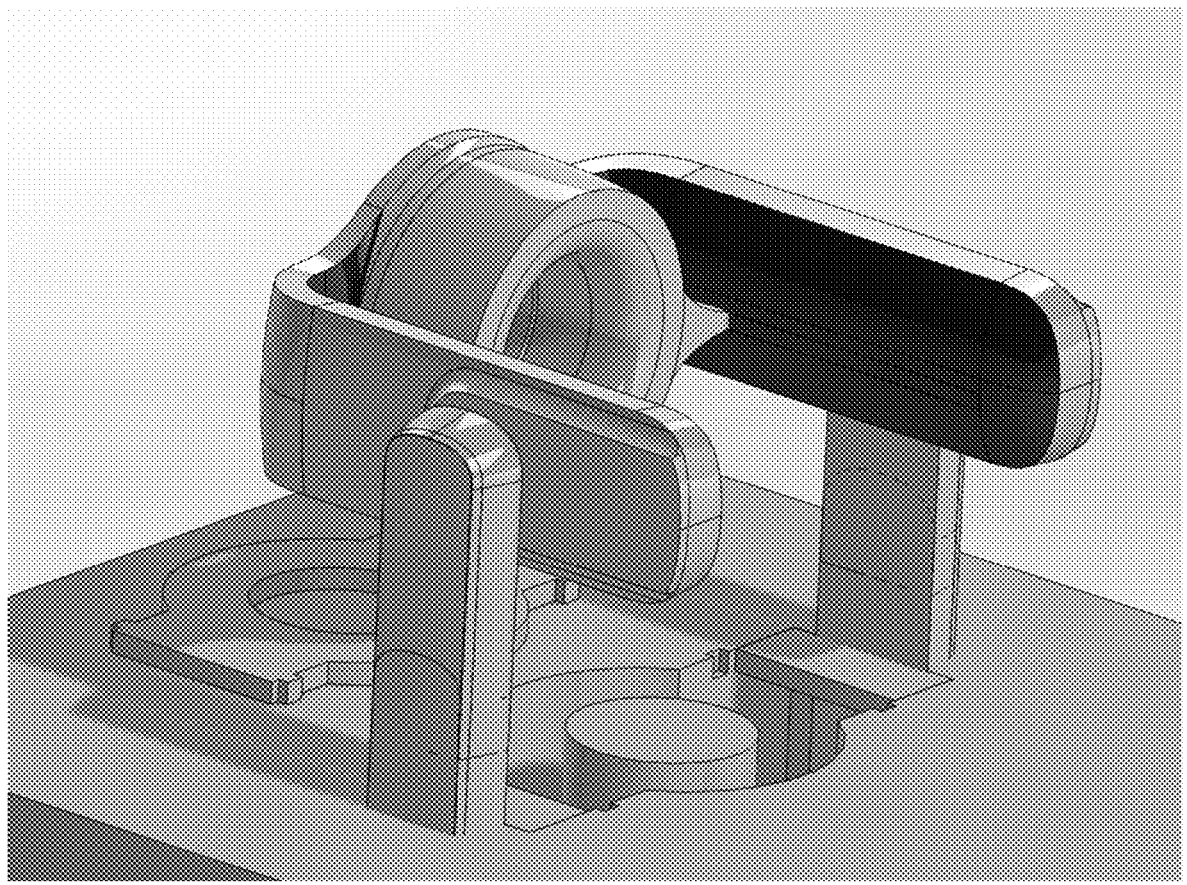
FIG. 14 is a drawing of an embodiment of the technology showing the multi-axis CT scanner rotating to a horizontal position after moving upward out of the floor (e.g., to scan a patient in a horizontal position or to scan a portion of a patient in a horizontal position).
Figure 15A:
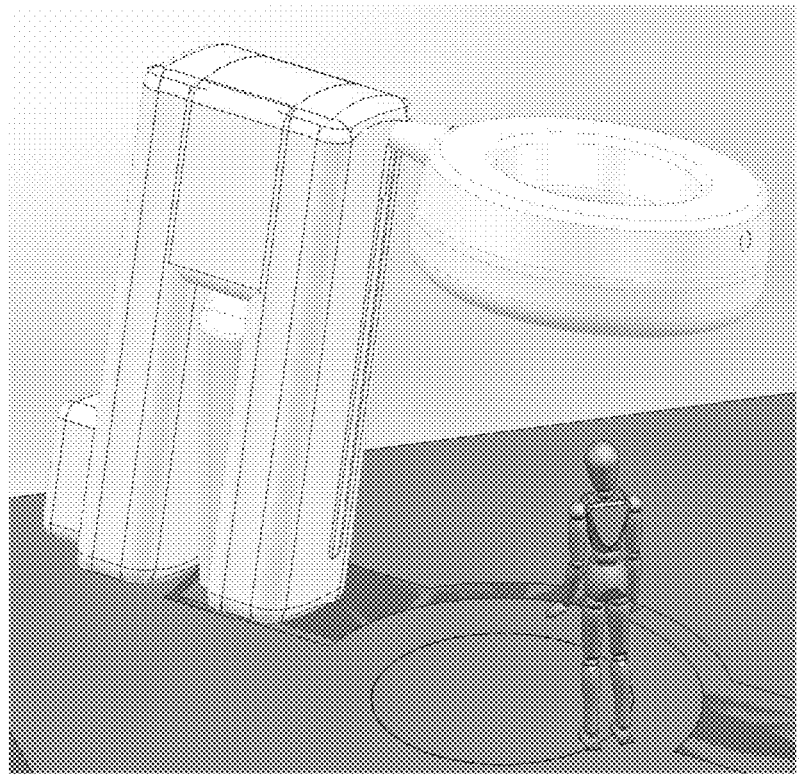
FIG. 15A is a model of an embodiment of the technology comprising one stanchion, a gantry comprising one gantry arm (e.g., an A-shaped gantry arm), and a scanner ring.
Figure 15B:
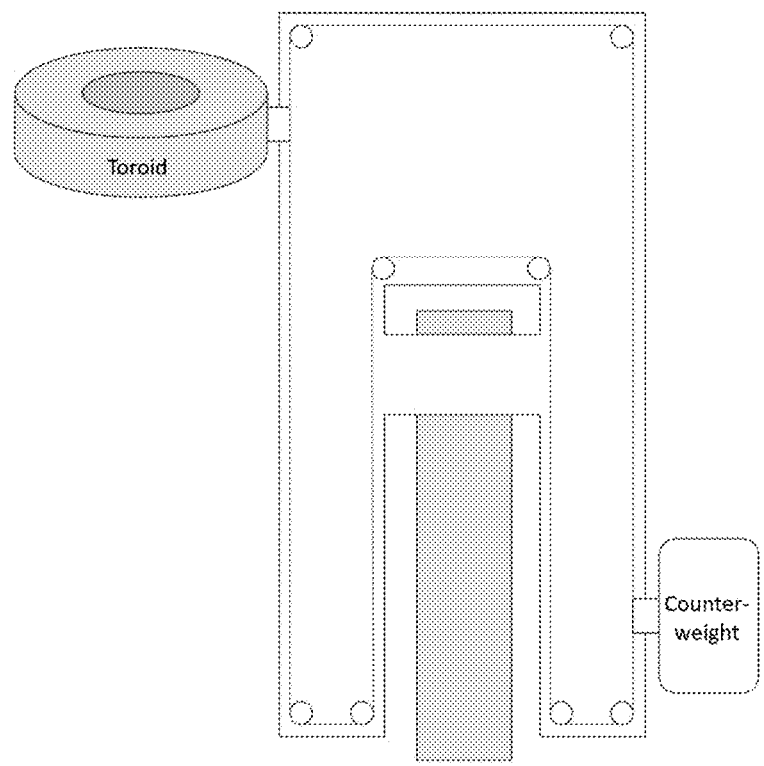
FIG. 15B is a schematic drawing of an embodiment of the technology comprising one stanchion, a gantry comprising one gantry arm (e.g., an A-shaped gantry arm), and a scanner ring. The embodiment shown in FIG. 15B shows a scanner ring and counterweight driven by a belt and pulley system.
Figure 16A:
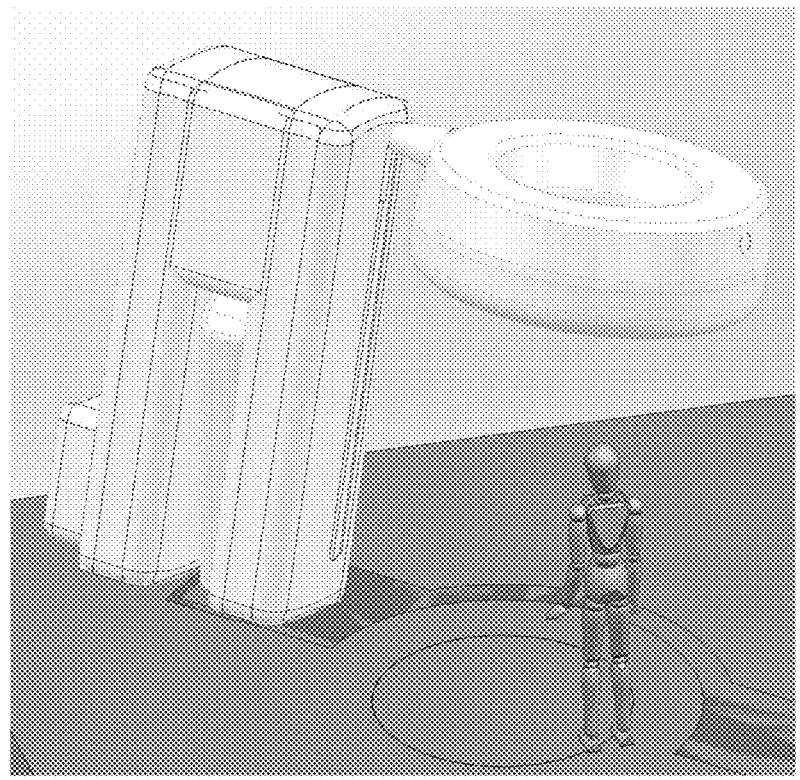
FIG. 16A is a model of an embodiment of the technology comprising one stanchion, a gantry comprising one gantry arm (e.g., an A-shaped gantry arm), and a scanner ring.
Figure 16B:
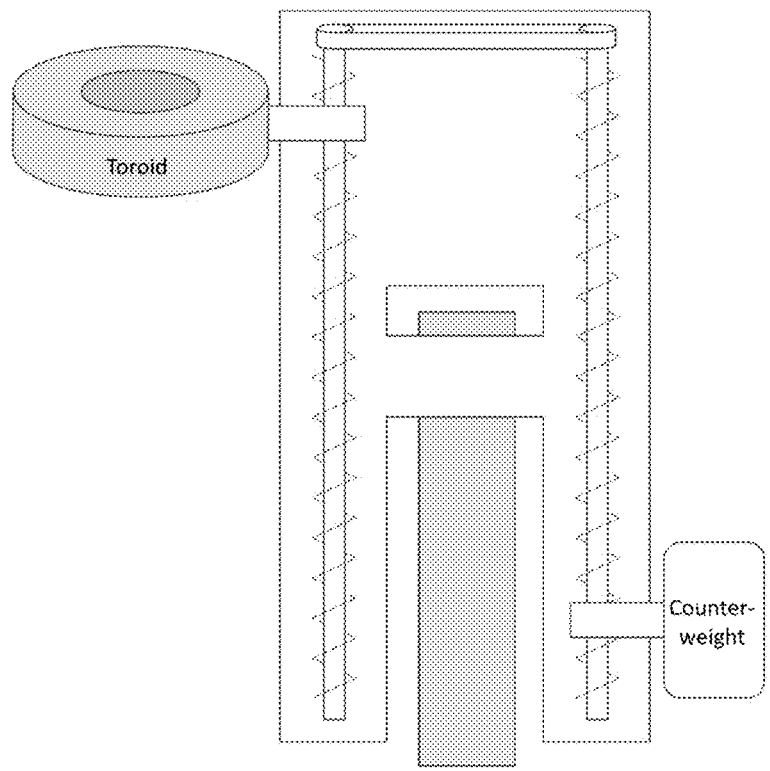
FIG. 16B is a schematic drawing of an embodiment of the technology comprising one stanchion, a gantry comprising one gantry arm (e.g., an A-shaped gantry arm), and a scanner ring. The embodiment shown in FIG. 16B shows a scanner ring and counterweight driven by a system comprising ball screws coordinated by a belt.

In some embodiments, the scanner ring is positioned beneath the patient. In some embodiments, the scanner ring is located within a recess (e.g., a pit) in the floor and translates up around the patient after the patient is positioned. In some embodiments, the scanner ring is positioned in a first position and is moved (e.g., rotated on the gantry) to be placed beneath the patient. In some embodiments, the scanner ring is placed as described in U.S. Pat. No. 9,301,726, incorporated herein by reference. In some embodiments, the technology provides a multi-axis imaging apparatus (e.g., a CT scanner) as shown in FIG. 9-14. For example, e.g., as shown in FIG. 9, in some embodiments, the multi-axis imaging apparatus comprises stanchions and a scanner ring that is provided in a first position in a pit in the floor. As shown in FIG. 10, the multi-axis imaging apparatus comprises stanchions (e.g., a first stanchion and/or a second stanchion). In some embodiments, the stanchions are mounted into the floor of a room in which the multi-axis imaging apparatus is located. In some embodiments, the stanchions can be moved in the plane of the floor (e.g., to change their X-Y position in the X-Y plane), e.g., to move the multi-axis imaging apparatus into a position to obtain a medical image of a patient.

In some embodiments, motors (e.g., motors structured to rotate the gantry relative to the stanchions), electrical supply wires, and/or communications cables are provided within one or both stanchions. Further, in some embodiments, the multi-axis imaging apparatus comprises a gantry (e.g., a "U-shaped" gantry). In some embodiments, the gantry comprises a first gantry arm and a second gantry arm. In some embodiments, the scanner ring moves along the gantry to move up out of the floor. In some embodiments, moving the scanner ring lifts a floor insert. In some embodiments, methods comprise moving the floor insert, e.g., to raise the scanner ring out of the floor. See FIG. 13.

In some embodiments, the gantry rotates around an axis relative to the first stanchion and the second stanchion, e.g., the first gantry arm and the second gantry arm rotate around an axis relative to the first stanchion and the second stanchion. See FIG. 14. In some embodiments, motors (e.g., motors structured to rotate the gantry relative to the stanchions, electrical supply wires, and/or communications cables) are provided within one or both gantry arms. Further, in some embodiments, the multi-axis imaging apparatus comprises a scanner ring (e.g., a toroidal housing that comprises (e.g., encloses) an imaging source and an imaging detector). In some embodiments, rotating the gantry causes the scanner ring to revolve on an arc around an axis, e.g., to move it from a first position to a second position. In some embodiments, the floor insert is replaced into the pit to cover the pit, e.g., so that a patient may be placed within an appropriate location within the medical imaging apparatus to record a medical image.

In some embodiments, e.g., as shown in FIGS. 15A, 15B, 16A, 16B, 17A, 17B, 18A, and 18B, the technology provides a multi-axis medical imaging apparatus (e.g., a CT scanning apparatus) comprising a single stanchion, a gantry comprising a gantry arm, and a scanner ring. In some embodiments, the stanchion is mounted into the floor of a room in which the multi-axis medical imaging apparatus is located. In some embodiments, the stanchions can be moved in the plane of the floor (e.g., to change their X-Y position in the X-Y plane of the floor), e.g., to move the multi-axis CT scanner into a position to obtain a CT scan of a patient. In some embodiments, motors (e.g., motors structured to rotate the gantry relative to the stanchion), electrical supply wires, and/or communications cables are provided within the stanchion. In some embodiments, the gantry rotates around an axis relative to the stanchion, e.g., the gantry arm rotates around an axis relative to the stanchion. In some embodiments, motors (e.g., motors structured to rotate the gantry relative to the stanchion), electrical supply wires, and/or communications cables are provided within the gantry arm. Further, in some embodiments, the multi-axis CT scanner comprises a scanner ring (e.g., a toroidal housing that comprises (e.g., encloses) the X-ray source and X-ray detector). See, e.g., 15A, 15B, 16A, 16B, 17A, 17B, 18A, and 18B. In some embodiments, rotating the gantry causes the scanner ring to revolve on an arc around an axis, e.g., to move it from a first position to a second position. In some embodiments, the first position of the scanner ring allows a patient to access and/or to exit a patient positioning system and/or patient support. In some embodiments, the second position of the scanner ring is a position used to obtain a CT scan of a patient. In some embodiments, the second position of the scanner ring is over the head of the patient. In some embodiments, the inner diameter of the scanner ring is 20 cm or more (e.g., 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 cm).

In some embodiments, the scanner ring comprises a source and a detector for CT, MRI, PET, SPECT, photon counting computed tomography, or portal imaging. Accordingly, in some embodiments, the scanner ring comprises a medical imaging source (e.g., electromagnetic radiation source, X-ray source, gamma ray source, radio wave source, photon source, proton source, positron source, gamma ray source (e.g., gamma rays from a positron source)) and a medical imaging detector (e.g., electromagnetic radiation detector, X-ray detector, photon detector, gamma ray detector), e.g., for one or more of these imaging modes.

Further, in some embodiments, the scanner ring is structured to translate along an axis substantially parallel to the gantry arm. In some embodiments, the scanner ring translates along a vertical (e.g., substantially and/or essentially vertical) axis, e.g., to obtain a CT scan of a patient in a vertical position. In some embodiments, the scanner ring translates along a horizontal (e.g., substantially and/or essentially horizontal) axis, e.g., to obtain a CT scan of a patient in a horizontal position. In some embodiments related to scanning a horizontal patient, the scanner ring moves into scanning position to scan a stationary patient in contrast to conventional technologies in which a patient is moved into scanning position and the scanner is stationary. The present technology thus provides advantages over conventional technologies for obtaining CT scans of horizontal patients. In some embodiments, motors (e.g., motors structured to translate the scanner ring relative to the gantry), electrical supply wires, and/or communications cables are provided within the gantry arm.

In some embodiments, the motor is coupled to a ball screw (e.g., comprising a threaded shaft and a ball assembly operationally attached to the scanner ring). See, e.g., FIGS. 16A and 16B. In some embodiments, the ball screw comprises a threaded shaft having a diameter of 15-100 mm (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm). In some embodiments, the ball screw provides a translation of the scanner ring of 5-100 mm/revolution (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm/revolution).

In some embodiments, a motor and a belt and pulley system is used to move the scanner ring. In some embodiments, the belt is operationally attached to the scanner ring. In some embodiments, the motor drives a belt operationally attached to the scanner ring. See, e.g., FIGS. 15A, 15B, 17A, 17B, 18A, and 18B. In some embodiments, the belt is operationally attached to the scanner ring and to the counterweights, e.g., to coordinate movement of the scanner ring mass and the counterweight mass.

Figure 17A:
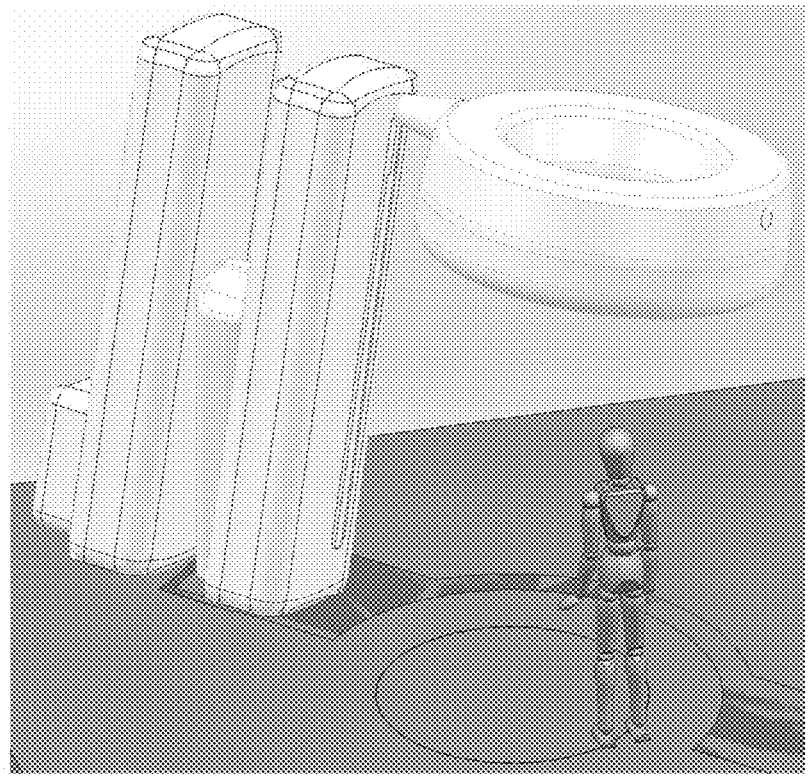
FIG. 17A is a model of an embodiment of the technology comprising one stanchion, a gantry comprising one gantry arm (e.g., an H-shaped gantry arm), and a scanner ring.
Figure 17B:
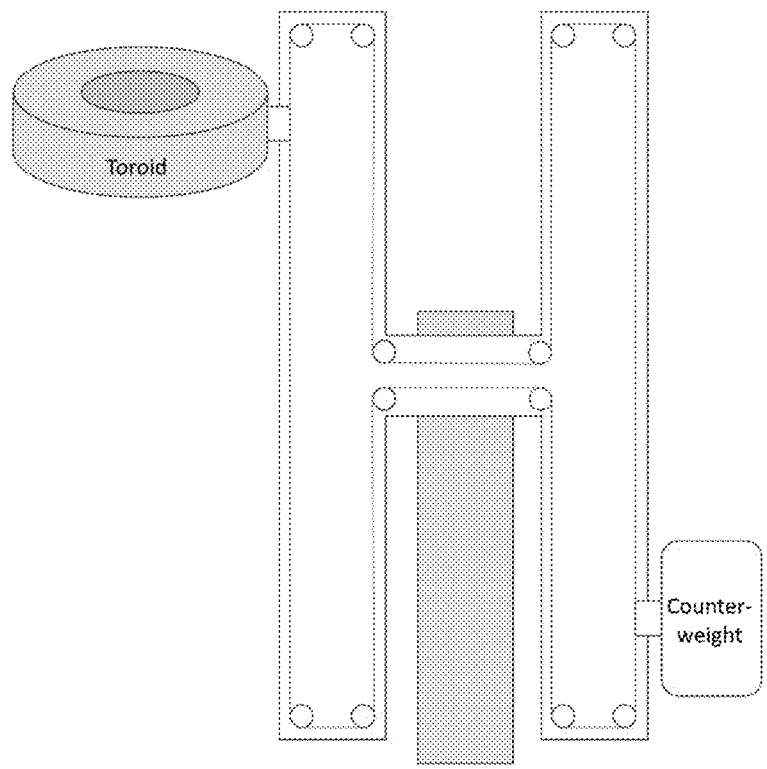
FIG. 17B is a schematic drawing of an embodiment of the technology comprising one stanchion, a gantry comprising one gantry arm (e.g., an H-shaped gantry arm), and a scanner ring. The embodiment shown in FIG. 17B shows a scanner ring and counterweight driven by a belt and pulley system.
Figure 18A:
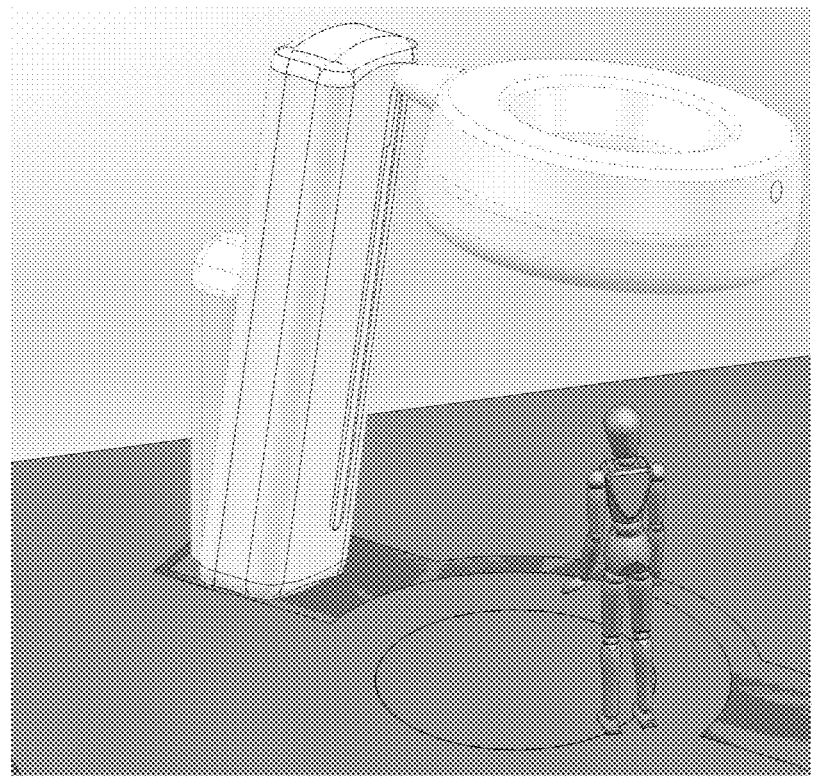
FIG. 18A is a model of an embodiment of the technology comprising one stanchion, a gantry comprising one gantry arm (e.g., an A-shaped gantry arm), and a scanner ring.
Figure 18B:
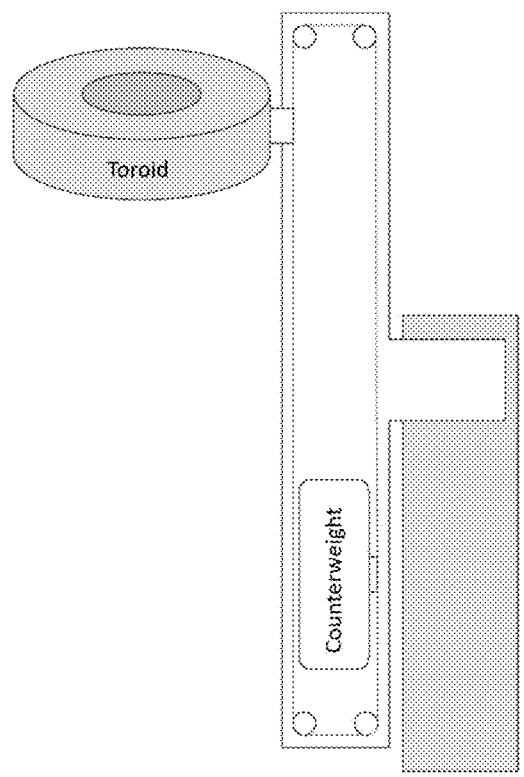
FIG. 18B is a schematic drawing of an embodiment of the technology comprising one stanchion, a gantry comprising one gantry arm (e.g., a T-shaped gantry arm), and a scanner ring. The embodiment shown in FIG. 18B shows a scanner ring and counterweight driven by a belt and pulley system.

In some embodiments, the gantry arm has an "A" shape as shown in FIGS. 15A, 15B, 16A, and 16B. In some embodiments, the gantry arm has an "H" shape as shown in FIGS. 17A and 17B. In some embodiments, the gantry arm has a "T" shape as shown in FIGS. 18A and 18B. In some embodiments of the medical imaging apparatus comprising a single stanchion and a single gantry arm described herein, the medical imaging apparatus comprises a counterweight (e.g., a supplemental mass component) as described below, e.g., to provide counterbalancing of the gantry arm and scanner ring.

In some embodiments, the scanner ring comprises (e.g., encloses) an X-ray generator that moves within the scanner ring and thus revolves around the patient. In some embodiments, the scanner ring comprises (e.g., encloses) one or more X-ray detectors. In some embodiments, the X-ray generator produces a fan beam of X-rays in a plane extending across the scanner ring. In some embodiments, the X-ray detector comprises an arcuate detector array within said plane at a substantially constant radius from the X-ray generator source. In some embodiments, multiple stationary X-ray detectors are positioned around the circumference of the scanner ring such that an X-ray detector is always on the opposite side of the from the X-ray source moving within the scanner ring. In some embodiments, the scanner ring comprises a moving X-ray detector that moves within the scanner ring and is positioned opposite the moving X-ray generator, e.g., the X-ray generator and the X-ray detector move in concert so that the X-ray generator and the X-ray detector are on opposite sides of the scanner ring. In some embodiments, the scanner ring is translated into position and is stationary while the X-ray generator and X-ray detector move around the circumference of the scanner ring. In some embodiments, the scanner ring is translated one or more times and/or is translated continuously while the X-ray generator and the X-ray detector move around the circumference of the scanner ring (e.g., to provide a helical scan). In some embodiments, the multi-axis CT scanner comprises a slip ring to transmit electrical power from the scanner ring to the X-ray generator and X-ray detector and to carry communications signals between the scanner ring and the X-ray generator and X-ray detector.

In some embodiments, the multi-axis imaging apparatus comprising a single stanchion finds use in providing (e.g., recording, acquiring) a portal image. In some embodiments, the multi-axis imaging apparatus finds use in scanned projection radiography ("scout scanning"). In some embodiments in which the multi-axis imaging apparatus is used for portal imaging and/or scanned projection radiography, the X-ray generator and the X-ray detector do not move (e.g., they do not rotate). In some embodiments, the scanner ring is stationary for portal imaging. In some embodiments, the scanner ring translates for scanned projection radiography.

Rapid Multi-Axis Computed Tomography

Horizontal CT scans and vertical CT scans can provide information for different purposes. For example, in imaging the spine for orthopedic purposes, an image obtained of a patient in a vertical position (e.g., while the spine is loaded) shows areas where the spine may be damaged and requires surgery. However, surgeries are performed on patients in horizontal positions, thus requiring an image of a patient in a horizontal position to plan the surgery. Thus, it may be advantageous to be able to obtain both types of images (e.g., an image of a patient in a horizontal position and an image of a patient in a vertical position) quickly in a single imaging session while the patient is placed on the CT scanner platform (e.g., patient support). Further, comparing images of patients in horizontal and vertical positions can provide diagnostic information based on differences in anatomy and/or physiology that become evident when comparing images obtained in the two orientations. For example, comparing images of patient vasculature obtained while the patient is in a horizontal position with images of patient vasculature obtained while the patient is in a vertical position may highlight problems in blood vessels that become evidence as a result of differences in hydrostatic pressures exerted on vasculature by blood in the two positions.

However, most conventional CT scanners are configured to produce horizontal CT scan images or vertical CT scan images but are not configured to produce both horizontal CT scan images and vertical CT scan images. Thus, obtaining horizontal and vertical CT scans of the same patient using conventional technology requires two CT scanners and positioning the patient independently on each one for imaging.

Thus, in some embodiments, the technology relates to a CT scanner that can provide CT scans of a patient in both horizontal and vertical positions after a patient is positioned on the CT scanner. That is, in some embodiments, the same CT scanner is used to obtain CT scans of a patient in a horizontal position and the patient in a vertical position. For example, embodiments provide that a patient is positioned on the CT scanner platform (e.g., patient support) in a vertical position; a CT scan is obtained of the patient in a vertical position; the CT platform (e.g., CT scanner gantry and patient support) is rotated to place the patient in a horizontal position; and a CT scan is obtained of the patient in the horizontal position. The patient can then exit the CT scanner while the patient support is in a horizontal position, or the CT gantry and patient support can be rotated to a vertical position so that the patient can exit the CT scanner from a standing position. Thus, embodiments of the technology provide a multi-axis rapid CT scanner that can be placed in horizontal scanning and vertical scanning positions, and in angles therebetween, with the patient placed on the scanner patient support. Both horizontal and vertical scans can be obtained in much less time that using conventional CT scanning technologies.

In some embodiments, the technology provides a rapid multi-axis CT scanner that is similar to the multi-axis CT scanner described herein, except the gantry arms are further connected by a bottom bridging component and the patient positioning system and/or patient support is/are replaced by a patient support that spans the top bridge connecting the two gantry arms and the added bottom bridge".

Figure 19A:
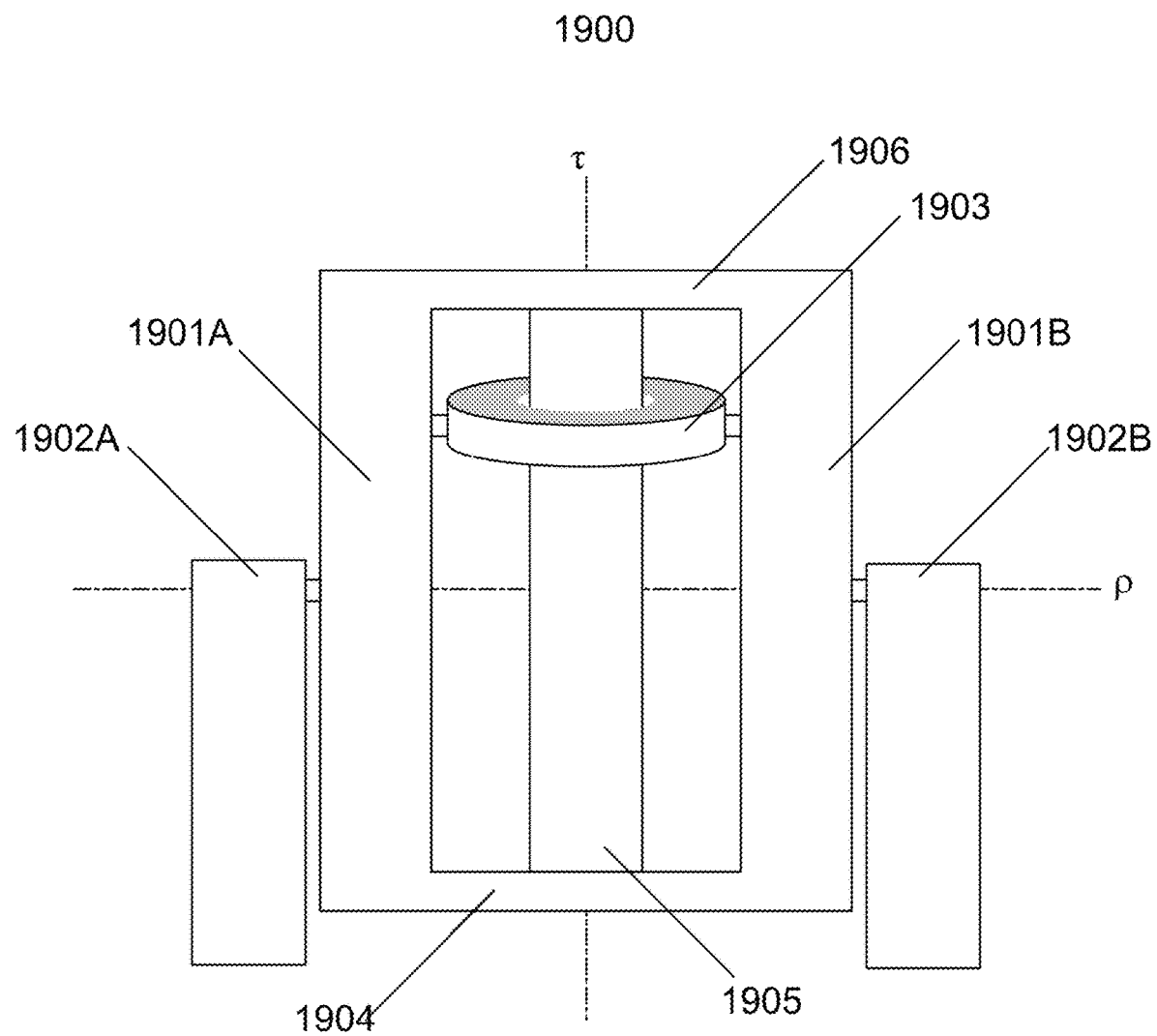
FIG. 19A is a drawing of a rapid multi-axis CT (RMACT) scanner shown in front view. The RMACT scanner 1900 comprises a first stanchion 1902A, a second stanchion 1902B, a first gantry arm 1901A, a second gantry arm 1901B, and a scanner ring 1903. A bottom bridge 1904 and a top bridge 1906 connect the first gantry arm 1901A to the second gantry arm 1901B. A patient support 1905 is connected to the bottom bridge 1904 and the top bridge 1906. The gantry comprising the first gantry arm 1901A and the second gantry arm 1901B rotates around axis ρ with respect to the first stanchion 1902A and the second stanchion 1902B. Scanner ring 1903 translates along axis T with respect to the gantry comprising the first gantry arm 1901A and the second gantry arm 1901B. The RMACT scanner 1900 in FIG. 19A is shown with the patient support 1905 in a vertical position (e.g., a substantially and/or effectively vertical position), e.g., to support a patient in a vertical position (e.g., substantially and/or effectively vertical position) such as a standing or other upright (e.g., sitting, kneeling, perched) position.
Figure 19B:
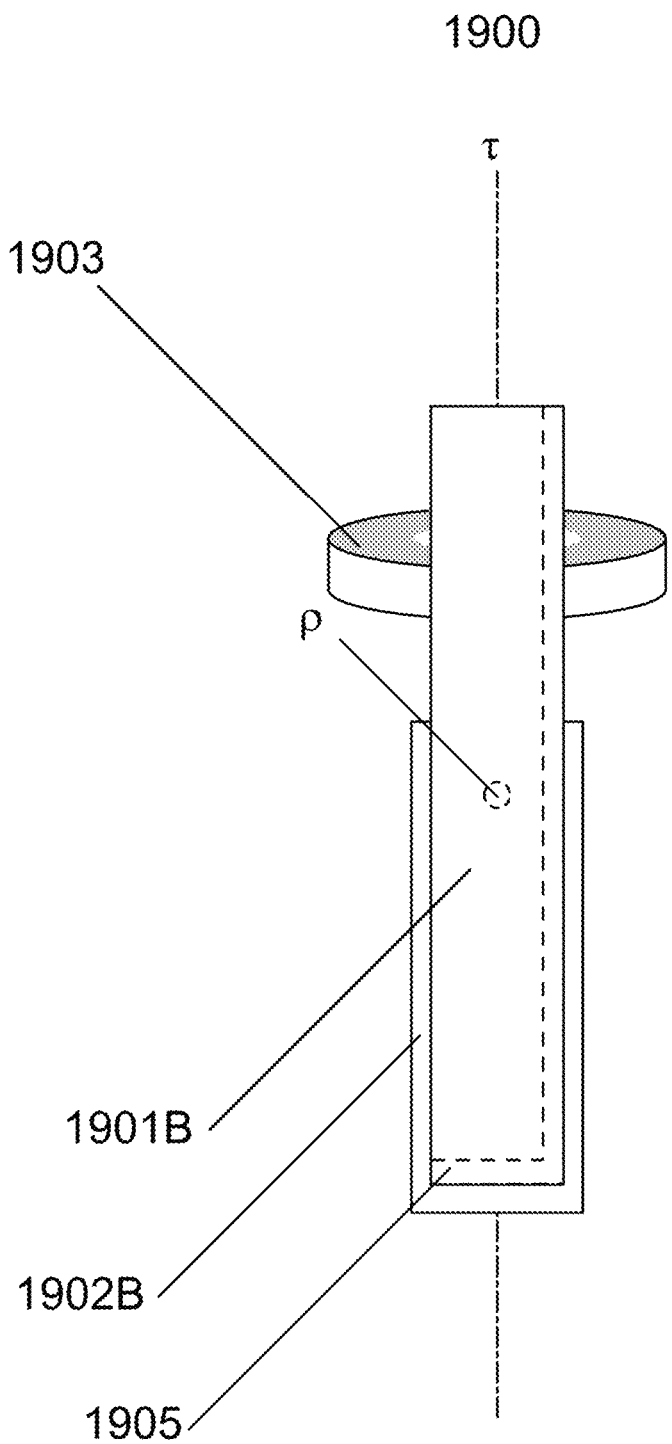
FIG. 19B is a drawing of the RMACT scanner 1900 of FIG. 19A shown in a side view.
Figure 19C:
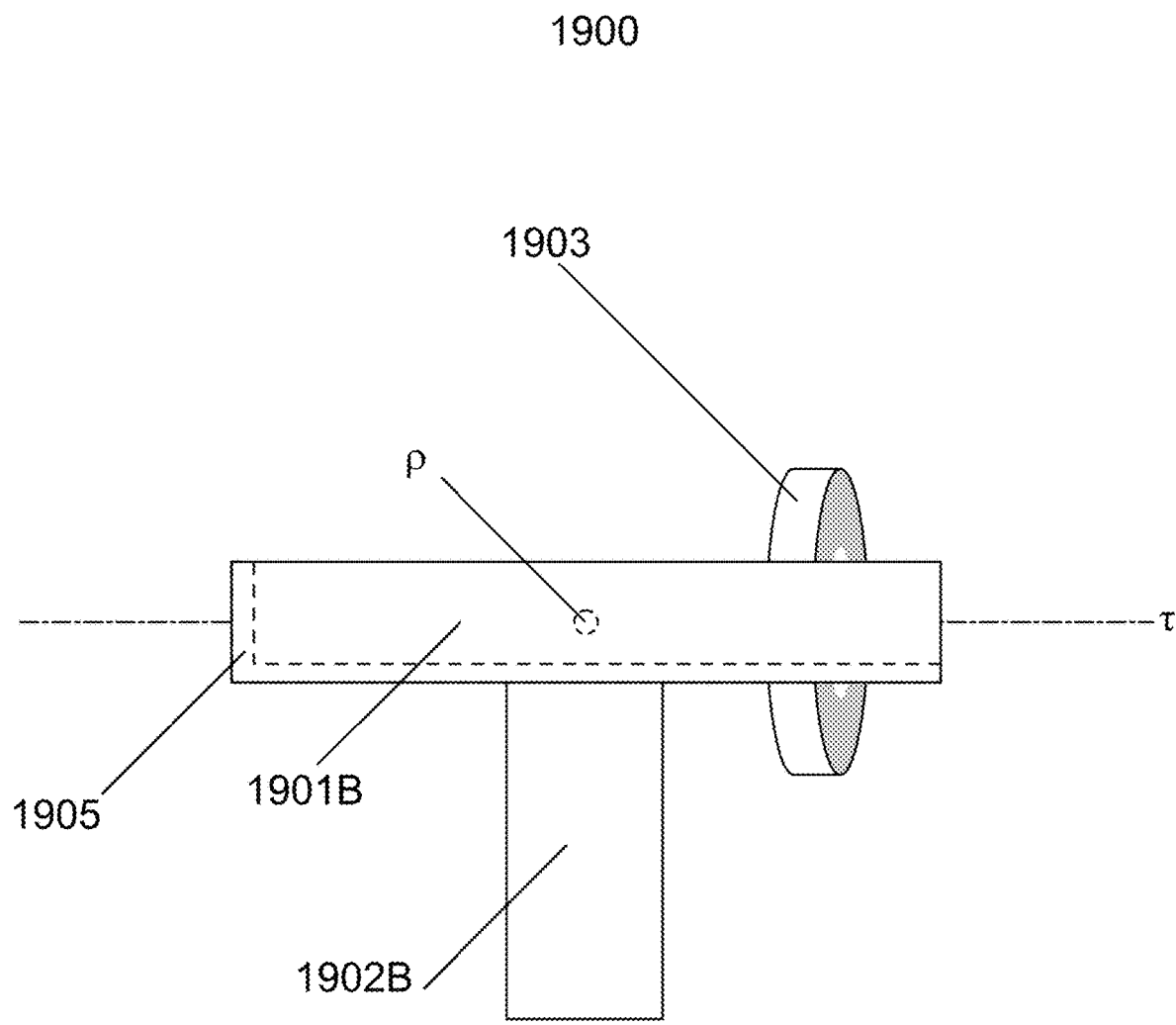
FIG. 19C is a drawing of the RMACT scanner 1900 of FIG. 19A and FIG. 19B shown in a side view with the gantry (and patient support) rotated 90° with respect to the position of the gantry (and patient support) as shown in FIG. 19B to provide the patient support 1905 in a horizontal position (e.g., a substantially and/or effectively horizontal position), e.g., to support a patient in a horizontal position (e.g., a substantially and/or effectively horizontal position) such as a lying position (e.g., prone, supine, Trendelenburg, or other horizontal position) with legs straight or bent.

For example, e.g., as shown in FIG. 19A to FIG. 19C, embodiments of the technology provide a multi-axis imaging technology that is a rapid multi-axis computed tomography (RMACT) imaging technology. In some embodiments, e.g., as shown in FIG. 19A to C, the RMACT imaging technology provides a rapid multi-axis CT (RMACT) scanner. In some embodiments, the RMACT scanner 1900 comprises a first stanchion 1902A, a second stanchion 1902B, a first gantry arm 1901A, a second gantry arm 1901B, and a scanner ring 1903; a bottom bridge 1904 and a top bridge 1906 that connect the first gantry arm 1901A to the second gantry arm 1901B; and a patient support 1905 that is connected to the bottom bridge 1904 and the top bridge 1906. In some embodiments, the height of the gantry, e.g., the distance from the top bridge 1906 to the bottom bridge 1904 is approximately 2.3 m (e.g., 2.0 to 2.5 m (e.g., 2.0, 2.1, 2.2, 2.3, 2.4, or 2.5 m)).

As shown in FIGS. 19B and 19C, the RMACT gantry comprising the first gantry arm 1901A and the second gantry arm 1901B rotates around axis ρ with respect to the first stanchion 1902A and the second stanchion 1902B. In some embodiments, the RMACT scanner is structured to comprise the gantry and patient support (e.g., comprising a patient) in a first position (e.g., a horizontal position), the RMACT scanner is structured to rotate the gantry and patient support by approximately 45 to 135° (e.g., 45, 50, 55, 60, 65, 70, 75, 80, 85, 90, 95, 100, 105, 110, 115, 120, 125, 130, or 135°), and the RMACT scanner is structured to comprise the gantry and patent support (e.g., comprising the patient) in a second position (e.g., a vertical position). In some embodiments, the RMACT scanner is structured to rotate the gantry and patient support by approximately 90° (e.g., 80 to 100° (e.g., 80, 81, 82, 83, 84, 85, 86, 87, 88, 89, 90, 91, 92, 93, 94, 95, 96, 97, 98, 99, or 100° C.)).

Further, scanner ring 1903 translates along axis T with respect to the gantry comprising the first gantry arm 1901A and the second gantry arm 1901B. The RMACT scanner 1900 in FIG. 19A and FIG. 19B is shown with the patient support 1905 in a vertical position (e.g., a substantially and/or effectively vertical position) to support a patient in a vertical position (e.g., substantially and/or effectively vertical position) such as a standing or perched position. The RMACT scanner 1900 shown in FIG. 19C is shown with the gantry (and patient support) rotated 90° with respect to the position of the gantry (and patient support) as shown in FIG. 19B to provide the patient support 1905 in a horizontal position (e.g., a substantially and/or effectively horizontal position), e.g., to support a patient in a horizontal position (e.g., a substantially and/or effectively horizontal position) such as a lying position (e.g., prone, supine, Trendelenburg, or other horizontal position) with legs straight or bent.

In some embodiments, the stanchions are mounted into the floor of a room in which the RMACT scanner is located. In some embodiments, the stanchions can be moved in the plane of the floor (e.g., to change their X-Y position in the X-Y plane), e.g., to move the RMACT scanner into a position to obtain a CT scan of a patient. In some embodiments, motors (e.g., motors structured to rotate the gantry relative to the stanchions 1902A and 1902B), electrical supply wires, and/or communications cables are provided within one or both stanchions. In some embodiments, motors (e.g., motors structured to rotate the gantry relative to the stanchions), electrical supply wires, and/or communications cables are provided within one or both gantry arms 1901A and/or 1901B.

Further, in some embodiments, the multi-axis CT scanner comprises a scanner ring 1903 (e.g., a toroidal housing that comprises (e.g., encloses) the X-ray source and X-ray detector). In some embodiments, rotating the gantry causes the scanner ring 1903 to revolve on an arc around axis ρ, e.g., to move it from a first position to a second position. In some embodiments, the inner diameter of the scanner ring is 20 cm or more (e.g., 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 cm).

In some embodiments, the technology provides an advantage of comprising a scanner ring that is smaller and/or has less mass than conventional scanner rings. For example, in some embodiments, the scanner ring has a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms).

In some embodiments, a smaller and/or less massive scanner ring further contributes to the manipulability of the RMACT scanner technology, e.g., because the gantry and/or scanner ring is easier to move and/or manipulate than in conventional technologies. In some embodiments, a smaller and/or less massive scanner ring further contributes to the advantage of the components of the multi-axis CT scanner being moved with minimal and/or decreased force provided by a user and/or a motor to move the RMACT scanner ring technology, e.g., because the gantry and/or scanner ring is moved and/or manipulated with decreased and/or minimal force relative to previous technologies. In some embodiments, the smaller scanner ring comprises a rotating anode tube that draws 300 mA (e.g., 250, 260, 270, 280, 290, 300, 310, 320, 330, 340, or 350 mA) and provides approximately 4 and/or at least 4 (e.g., 3, 4, 5, 6, 7, 8 or more)×40-cm (e.g., 35.0, 35.1, 35.2, 35.3, 35.4, 35.5, 35.6, 35.7, 35.8, 35.9, 36.0, 36.1, 36.2, 36.3, 36.4, 36.5, 36.6, 36.7, 36.8, 36.9, 37.0, 37.1, 37.2, 37.3, 37.4, 37.5, 37.6, 37.7, 37.8, 37.9, 38.0, 38.1, 38.2, 38.3, 38.4, 38.5, 38.6, 38.7, 38.8, 38.9, 39.0, 39.1, 39.2, 39.3, 39.4, 39.5, 39.6, 39.7, 39.8, 39.9, 40.0, 40.1, 40.2, 40.3, 40.4, 40.5, 40.6, 40.7, 40.8, 40.9, 41.0, 41.1, 41.2, 41.3, 41.4, 41.5, 41.6, 41.7, 41.8, 41.9, 42.0, 42.1, 42.2, 42.3, 42.4, 42.5, 42.6, 42.7, 42.8, 42.9, 43.0, 43.1, 43.2, 43.3, 43.4, 43.5, 43.6, 43.7, 43.8, 43.9, 44.0, 44.1, 44.2, 44.3, 44.4, 44.5, 44.6, 44.7, 44.8, 44.9, or 45.0-cm) scans in an hour with a field of view of approximately 63 cm (e.g., 58.0, 58.1, 58.2, 58.3, 58.4, 58.5, 58.6, 58.7, 58.8, 58.9, 59.0, 59.1, 59.2, 59.3, 59.4, 59.5, 59.6, 59.7, 59.8, 59.9, 60.0, 60.1, 60.2, 60.3, 60.4, 60.5, 60.6, 60.7, 60.8, 60.9, 61.0, 61.1, 61.2, 61.3, 61.4, 61.5, 61.6, 61.7, 61.8, 61.9, 62.0, 62.1, 62.2, 62.3, 62.4, 62.5, 62.6, 62.7, 62.8, 62.9, 63.0, 63.1, 63.2, 63.3, 63.4, 63.5, 63.6, 63.7, 63.8, 63.9, 64.0, 64.1, 64.2, 64.3, 64.4, 64.5, 64.6, 64.7, 64.8, 64.9, or 65.0 cm), while also being smaller and comprising less mass than previous scanner rings. For example, in some embodiments, the scanner ring measures approximately 33.5 cm (e.g., 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 cm) across, e.g., from the inner circumference (e.g., the inner bore) to the outer circumference.

In some embodiments, the scanner ring comprises a source and a detector for CT, MRI, PET, SPECT, photon counting computed tomography, or portal imaging. Accordingly, in some embodiments, the scanner ring comprises a medical imaging source (e.g., electromagnetic radiation source, X-ray source, gamma ray source, radio wave source, photon source, proton source, positron source, gamma ray source (e.g., gamma rays from a positron source)) and a medical imaging detector (e.g., electromagnetic radiation detector, X-ray detector, photon detector, gamma ray detector), e.g., for one or more of these imaging modes.

Further, in some embodiments, the scanner ring 1903 is structured to translate along an axis substantially parallel to the long dimension of the first gantry arm 1901A and the second gantry arm 1902B, e.g., along axis T as shown in FIG. 19A-C. In some embodiments, the scanner ring translates along a vertical (e.g., substantially and/or essentially vertical) axis, e.g., to obtain a CT scan of a patient in a vertical position. In some embodiments, the scanner ring translates along a horizontal (e.g., substantially and/or essentially horizontal) axis, e.g., to obtain a CT scan of a patient in a horizontal position. In some embodiments related to scanning a horizontal patient, the scanner ring 1903 moves into scanning position to scan a stationary patient in contrast to conventional technologies in which a patient is moved into scanning position and the scanner is stationary. In some embodiments, motors (e.g., motors structured to translate the scanner ring 1903 relative to the gantry), electrical supply wires, and/or communications cables are provided within one or both gantry arms. In some embodiments, the motor is coupled to a belt, chain, or a ball screw (e.g., comprising a threaded shaft and a ball assembly operationally attached to the scanner ring).

In some embodiments, the motor is coupled to a ball screw (e.g., comprising a threaded shaft and a ball assembly operationally attached to the scanner ring). In some embodiments, the ball screw comprises a threaded shaft having a diameter of 15-100 mm (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm) In some embodiments, the ball screw provides a translation of the scanner ring of 5-100 mm/revolution (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm/revolution).

In some embodiments, the motor drives a belt operationally attached to the scanner ring. In some embodiments, a motor and a belt and pulley system is used to move the scanner ring. In some embodiments, the belt is operationally attached to the scanner ring. In some embodiments, the motor drives a belt operationally attached to the scanner ring. In some embodiments, the belt is operationally attached to the scanner ring and to counterweights, e.g., to coordinate movement of the scanner ring mass and a counterweight mass, e.g., as described herein.

In some embodiments, the RMACT scanner ring 1903 comprises (e.g., encloses) an X-ray generator that moves within the scanner ring 1903 and thus revolves around the patient. In some embodiments, the RMACT scanner ring 1903 comprises (e.g., encloses) one or more X-ray detectors. In some embodiments, the X-ray generator produces a fan beam of X-rays in a plane extending across the scanner ring. In some embodiments, the X-ray detector comprises an arcuate detector array within said plane at a substantially constant radius from the X-ray generator source. In some embodiments, multiple stationary X-ray detectors are positioned around the circumference of the scanner ring 1903 such that an X-ray detector is always on the opposite side of the from the X-ray source moving within the scanner ring 1903. In some embodiments, the scanner ring 1903 comprises a moving X-ray detector that moves within the scanner ring 1903 and is positioned opposite the moving X-ray generator, e.g., the X-ray generator and the X-ray detector move in concert so that the X-ray generator and the X-ray detector are on opposite sides of the scanner ring 1903. In some embodiments, the scanner ring 1903 is translated into position and is stationary while the X-ray generator and X-ray detector move around the circumference of the scanner ring 1903. In some embodiments, the scanner ring 1903 is translated one or more times and/or is translated continuously while the X-ray generator and the X-ray detector move around the circumference of the scanner ring 1903 (e.g., to provide a helical scan). In some embodiments, the RMACT scanner comprises a slip ring to transmit electrical power from the scanner ring 1903 to the X-ray generator and X-ray detector and to carry communications signals between the scanner ring 1903 and the X-ray generator and X-ray detector.

In some embodiments, the RMACT apparatus finds use in providing (e.g., recording, acquiring) a portal image. In some embodiments, the multi-axis imaging apparatus finds use in scout scanning. In some embodiments in which the RMACT apparatus is used for portal imaging and/or scout scanning, the X-ray generator and the X-ray detector do not move (e.g., they do not revolve around the patient). In some embodiments, the scanner ring is stationary for portal imaging. In some embodiments, the scanner ring translates for scout scanning.

In some embodiments, the technology provides methods for obtaining a number of medical images (e.g., CT scan(s), magnetic resonance imaging (MRI) scan(s), positron emission tomography (PET) scan(s), single-photon emission computerized tomography (SPECT) scan(s), photon counting computed tomography scan(s), or portal image(s) or scanogram(s) (e.g., scanned projection radiography image (s)) using the RMACT scanner as described herein. In some embodiments, methods comprise providing a rapid multi-axis CT scanner as described herein. For example, in some embodiments, methods comprise providing a rapid multi-axis CT scanner comprises a first stanchion, a second stanchion, a first gantry arm, a second gantry arm, and a scanner ring; a bottom bridge and a top bridge that connect the first gantry arm to the second gantry arm; and a patient support that is connected to the bottom bridge and the top bridge. (see, e.g., FIG. 19A-C). In some embodiments, the technology relates to methods of scanning a patient using the RMACT scanner as described herein (e.g., to obtain a first image (e.g., a first CT image) of a patient in a horizontal position and to obtain a second image (e.g., a first CT image) of the patient in a vertical position). Accordingly, in some embodiments, methods comprise providing a rapid multi-axis CT (RMACT) scanner as described herein; scanning a patient in a horizontal position to obtain a first image; rotating the gantry, patient support, and/or patient (e.g., by approximately 90° (e.g., 80 to 100° (e.g., 80, 81, 82, 83, 84, 85, 86, 87, 88, 89, 90, 91, 92, 93, 94, 95, 96, 97, 98, 99, or 100° C.))); and scanning the patient in a vertical position to obtain a second image. In some embodiments, methods comprise providing a rapid multi-axis CT (RMACT) scanner as described herein; scanning a patient in a vertical position to obtain a first image; rotating the gantry, patient support, and/or patient (e.g., by approximately 90° (e.g., 80 to 100° (e.g., 80, 81, 82, 83, 84, 85, 86, 87, 88, 89, 90, 91, 92, 93, 94, 95, 96, 97, 98, 99, or 100° C.))); and scanning the patient in a horizontal position to obtain a second image. In some embodiments, methods further comprise comparing the first image and the second image. In the embodiments of methods comprising obtaining a first image (e.g., a first CT image) of a patient in a horizontal position and obtaining a second image (e.g., a first CT image) of the patient in a vertical position, the patient remains on the patient support (e.g., and is rotated on the patient support) between obtaining the first image and obtaining the second image.

In some embodiments, methods further comprise positioning a patient (e.g., on the patient support) for imaging with the RMACT scanner. In some embodiments, the patient is in a vertical position and methods comprise providing a patient in a vertical position. In some embodiments, the patient is standing (e.g., standing, standing and leaning backward, standing and leaning forward, perched, etc.) and methods comprise providing a patient in a standing (e.g., standing, standing and leaning backward, standing and leaning forward, perched, etc.) position. In some embodiments, the patient is sitting (e.g., seated, seated and leaning backward, seated and leaning forward, etc.) and methods comprise providing a patient in a sitting (e.g., seated, seated and leaning backward, seated and leaning forward, etc.) position. In some embodiments, the patient is kneeling (e.g., kneeling, kneeling and leaning forward, or kneeling and leaning backward), and methods comprise providing a patient in a kneeling (kneeling, kneeling and leaning forward, or kneeling and leaning backward) position.

In some embodiments, methods comprise providing a patient support to hold a patient in a vertical position (e.g., seated, seated and leaning backward, seated and leaning forward, standing, standing and leaning backward, standing and leaning forward, perched, kneeling, kneeling and leaning forward, or kneeling and leaning backward, or other vertical or substantially vertical position). Embodiments provide that the position and/or configuration of the patient anatomy (e.g., patient limbs, joints) in the vertical position (e.g., with respect to the patient support) is the same or similar as the position and/or configuration of the patient in the horizontal position (e.g., with respect to the patient support) after rotation of the patient and patient support. For example, in some embodiments, a patient is provided in a vertical position with knees bent and the patient is rotated to a horizontal position also with knees bent.

In some embodiments, the patient support is made from a light and strong material, such as a composite (e.g., carbon fiber (e.g., foam filled carbon fiber)). The patient support is manufactured to minimize and/or eliminate flex (e.g., due to gravity and patient mass) in the patient support, e.g., as the RMACT scanner is rotated between horizontal and vertical positions.

In some embodiments, the patient support comprises a number of patient support components, e.g., a shin rest, a seat, a heel stop (e.g., as described in Int'l Pat. App. Pub. No. WO 2019/056055, in U.S. Pat. App. Pub. No. 2020/

Figure 20A:
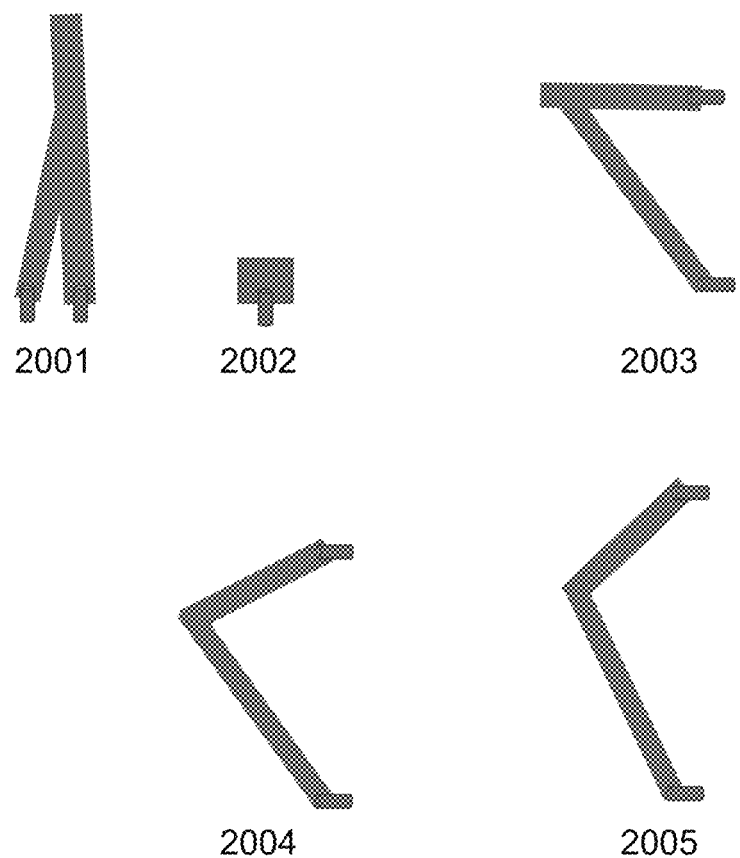
FIG. 20A shows modular patient support components for use with the patient support of the RMACT scanner.
Figure 20B:
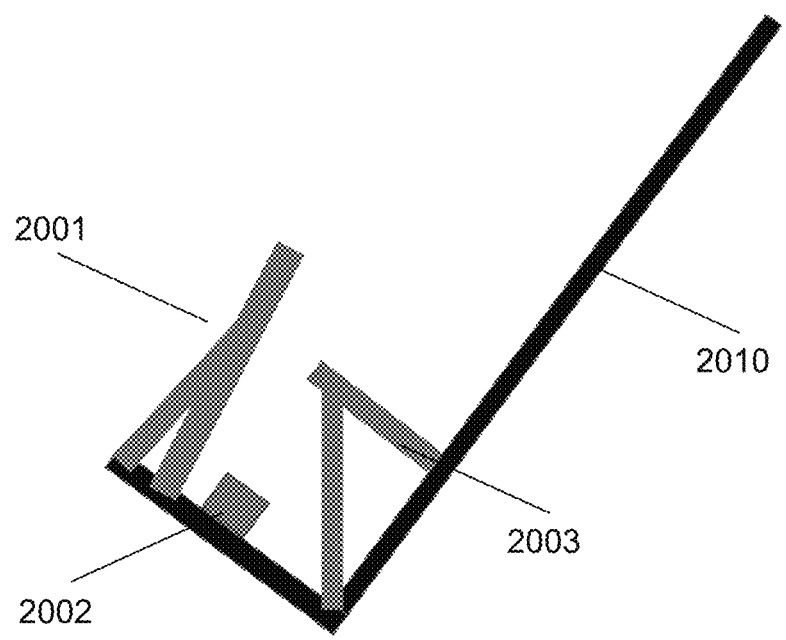
FIG. 20B shows a configuration of modular patient support components attached to a patient support to support a patient in a seated position.
Figure 20C:
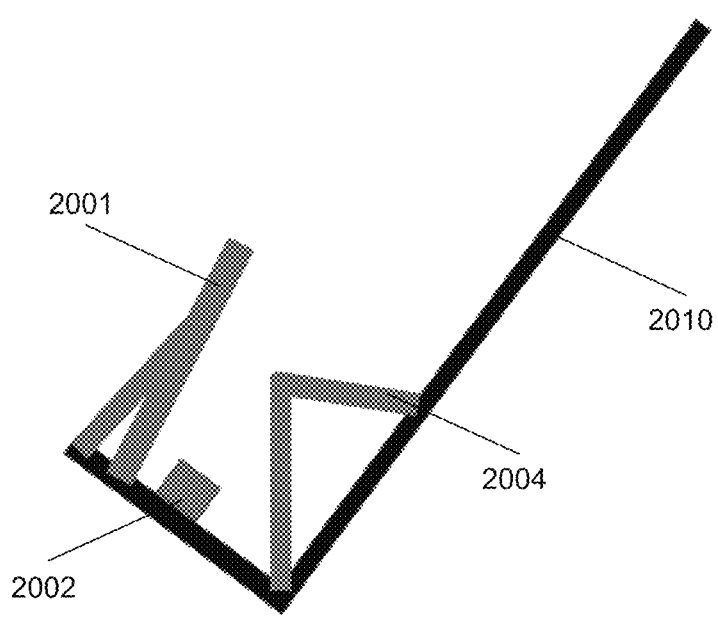
FIG. 20C shows a configuration of modular patient support components attached to a patient support to support a patient in a perched position.

0268327, and in U.S. Pat. App. Ser. No. 63/237,513, each of which is incorporated herein by reference). See, e.g., FIG. 20A. The exemplary patient support components shown in FIG. 20A include a shin rest (2001), a heel stop (2002), a seat (2003) (e.g., to position a patient in a seated position), a first perched seat (2004) (e.g., to position a patient in a first type of perched position), and a second perched seat (2005) (e.g., to position a patient in a second type of perch position). The components comprise interface structures (e.g., pegs, tabs, hooks) that are structured to interface with and attach the patient support components to the patient support. In some embodiments, the patient support components are modular and are used in combinations with the patient support to provide a number of different configurations for support different patient postures. For example, e.g., as shown in FIG. 20B, a shin rest 2001, a heel stop 2002, and a seat 2003 may be attached to the patient support 2010 to provide support for a patient in a seated position. As shown in FIG. 2C, a shin rest 2001, a heel stop 2002, and a perched seat 2004 may be attached to the patient support 2010 to provide support for a patient in a perched position. In some embodiments, the seat 2003 or perched seat (2004, 2005) may be attached at a number of places along the long axis of the patient support. In some embodiments, the seat 2003 or perched seat (2004, 2005) may be translated along the long axis of the patient support. In some embodiments, the shin rest and heel stop are also movable and/or translatable to provide custom configurable support for a patient placed on the patient support. In some embodiments, patient support components are produced using customized manufacturing methods (e.g., three-dimensional printing) with shapes customized for a specific patient to place the patient in one or more optimal postures.

In some embodiments, methods comprise rotating the gantry of the RMACT scanner. In some embodiments, rotating the gantry comprises rotating the gantry around an axis ρ relative to the first stanchion and/or the second stanchion. In some embodiments, methods comprise rotating the gantry from a horizontal position (e.g., a substantially and/or essentially horizontal position) to a vertical position (e.g., substantially and/or essentially vertical position), e.g., a rotation of approximately 90°. In some embodiments, methods comprise rotating the gantry from a vertical position (e.g., a substantially and/or essentially vertical position) to a horizontal position (e.g., substantially and/or essentially horizontal position), e.g., a rotation of approximately 90°. In some embodiments, rotating the gantry comprises activating a motor to apply a force to rotate the gantry. In some embodiments, rotating the gantry comprises manually pushing and/or pulling the gantry to rotate it. In some embodiments, methods comprise applying a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) to rotate the gantry, e.g., using a motor and/or using manual force. That is, in some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor.

In some embodiments, methods comprise translating the scanner ring of the RMACT scanner, e.g., from a first position away from the patient to a second position where the scanner ring surrounds the patient and/or the patient support. In some embodiments, translating the scanner ring comprises translating the scanner ring along an axis of translation (T) that is parallel (e.g., substantially and/or essentially parallel) to the long dimension of the gantry arms. In some embodiments, the scanner ring is translated approximately 0.20 to 2.00 m (e.g., 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, or 2.00 m).

In some embodiments, the gantry of the RMACT scanner and patient are in a vertical position (e.g., substantially and/or essentially vertical position) when the scanner ring is translated. In some embodiments, the gantry and patient are in a horizontal position (e.g., substantially and/or essentially horizontal position) when the scanner ring is translated (e.g., to obtain a CT scan of a lying patient).

In some embodiments, translating the scanner ring of the RMACT scanner comprises activating a motor to apply a force to translate the scanner ring. In some embodiments, translating the scanner ring comprises activating a rotatory motor to drive a belt or chain attached to the scanner ring. In some embodiments, translating the scanner ring comprises activating a motor coupled to a ball screw operationally coupled to the scanner ring. In some embodiments, the ball screw comprises a threaded shaft having a diameter of 15-100 mm (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100). In some embodiments, the ball screw provides a translation of the scanner ring of 5-100 mm/revolution (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mm/revolution).

In some embodiments, translating the scanner ring of the RMACT scanner comprises manually pushing and/or pulling the scanner ring to translate it. In some embodiments, methods comprise applying a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) to translate the scanner ring, e.g., using a motor and/or using manual force. That is, in some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor.

In some embodiments, methods comprise translating the RMACT scanner in the plane of the floor. For example, in some embodiments, methods comprise translating the RMACT scanner (e.g., by translating one or both stanchions) in the X-Y plane (e.g., in the plane of the floor), e.g., to position the scanner ring with respect to a patient and/or a region of interest of a patient.

In some embodiments, methods comprise obtaining (e.g., acquiring, recording, etc.) a medical image. In some embodiments, methods comprise obtaining (e.g., acquiring, recording, etc.) a CT image, MRI image, PET image, SPECT image, photon counting computed tomography image, or a portal image or scanned projection radiography image (e.g., "scout" scan). In some embodiments, methods comprise activating an imaging source (e.g., electromagnetic radiation source, X-ray source, gamma ray source, radio wave source, photon source, proton source, positron source, gamma ray source (e.g., gamma rays from a positron source)). In some embodiments, methods comprise activating an imaging detector (e.g., electromagnetic radiation detector, X-ray detector, photon detector, gamma ray detector), e.g., detecting electromagnetic radiation, X-rays, gamma rays, radio waves, photons, protons, positrons, etc. using the detector.

In some embodiments relating to CT scanning methods, methods comprise generating X-rays using an X-ray generator of the scanner ring of the RMACT scanner. In some embodiments, methods comprise detecting X-rays using an X-ray detector of the scanner ring. In some embodiments, methods comprise revolving an X-ray generator and an opposed X-ray detector around the patient. In some embodiments, methods comprise revolving an X-ray generator and an opposed X-ray detector around the patient while the scanner ring is stationary with respect to the gantry arms. In some embodiments, methods comprise revolving an X-ray generator and an opposed X-ray detector around the patient while the scanner ring moves with respect to the gantry arms.

In some embodiments, methods comprise translating the scanner ring, e.g., to a position where the scanner ring does not surround the patient and/or the patient support (e.g., to allow the patient to exit the RMACT scanning system). In some embodiments, methods comprise rotating the gantry to a horizontal position (e.g., substantially and/or essentially horizontal position). In some embodiments, translating the scanner ring away from the patient and/or rotating the gantry to a horizontal position comprises applying a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) to the scanner ring and/or gantry, respectively. In some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor. In some embodiments, translating the scanner ring away from the patient and/or rotating the gantry to a horizontal position comprises activating a motor to apply a force to translate the scanner ring away from the patient and/or rotate the gantry to a horizontal position. In some embodiments, translating the scanner ring away from the patient and/or rotating the gantry to a horizontal position comprises manually pushing and/or pulling the scanner ring to translate it away from the patient and/or the gantry to rotate it to a horizontal position. In some embodiments, methods comprise translating the scanner ring away from the patient and/or rotating the gantry to a horizontal position by a human user using manual force. In some embodiments, methods comprise translating the scanner ring away from the patient and/or rotating the gantry to a horizontal position by a human user using manual force and without the aid of a motor. For example, in some embodiments, methods comprise translating the scanner ring away from the patient and/or rotating the gantry to a horizontal position by a human user using manual force in the absence of electrical power, e.g., to allow a user to exit the CT scanner in the event of a power outage.

In some embodiments, the RMACT scanner comprises a gantry that is balanced (e.g., counterbalanced) with respect to the axis of rotation of the gantry. In some embodiments, the RMACT scanner comprises a counterweight for counterbalancing the gantry and/or the scanner ring. In some embodiments, the RMACT scanner comprises a counterweight for translation of the scanner ring.

Counterweighting and counterbalancing.

In some embodiments, the technology provides a multi-axis imaging apparatus (e.g., a computerized tomography (CT) apparatus, a magnetic resonance imaging (MRI) apparatus, a positron emission tomography (PET) apparatus, a single-photon emission computerized tomography (SPECT) apparatus, a photon counting computed tomography apparatus, or a portal imaging or scanned projection radiography apparatus) comprising counterbalancing and/or counterweighing to minimize the force applied to the apparatus to rotate the gantry and/or to translate the scanner ring. In some embodiments, the multi-axis imaging apparatus is a multi-axis computed tomography scanner or a rapid multi-axis computed tomography (RMACT) scanner. In some embodiments, a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is applied to the gantry to rotate it. In some embodiments, a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is applied to translate it. In some embodiments, the force is applied by a human alone, by a motor alone, or by a combination of a human and a motor (e.g., human with motor assistance). This design reduces drive train size and associated manufacturing and maintenance costs, improves accuracy, and improves system safety for patients and operators because movement of system components does not generate a force sufficient to injure a person and/or damage objects with which components may collide.

Figure 5A:
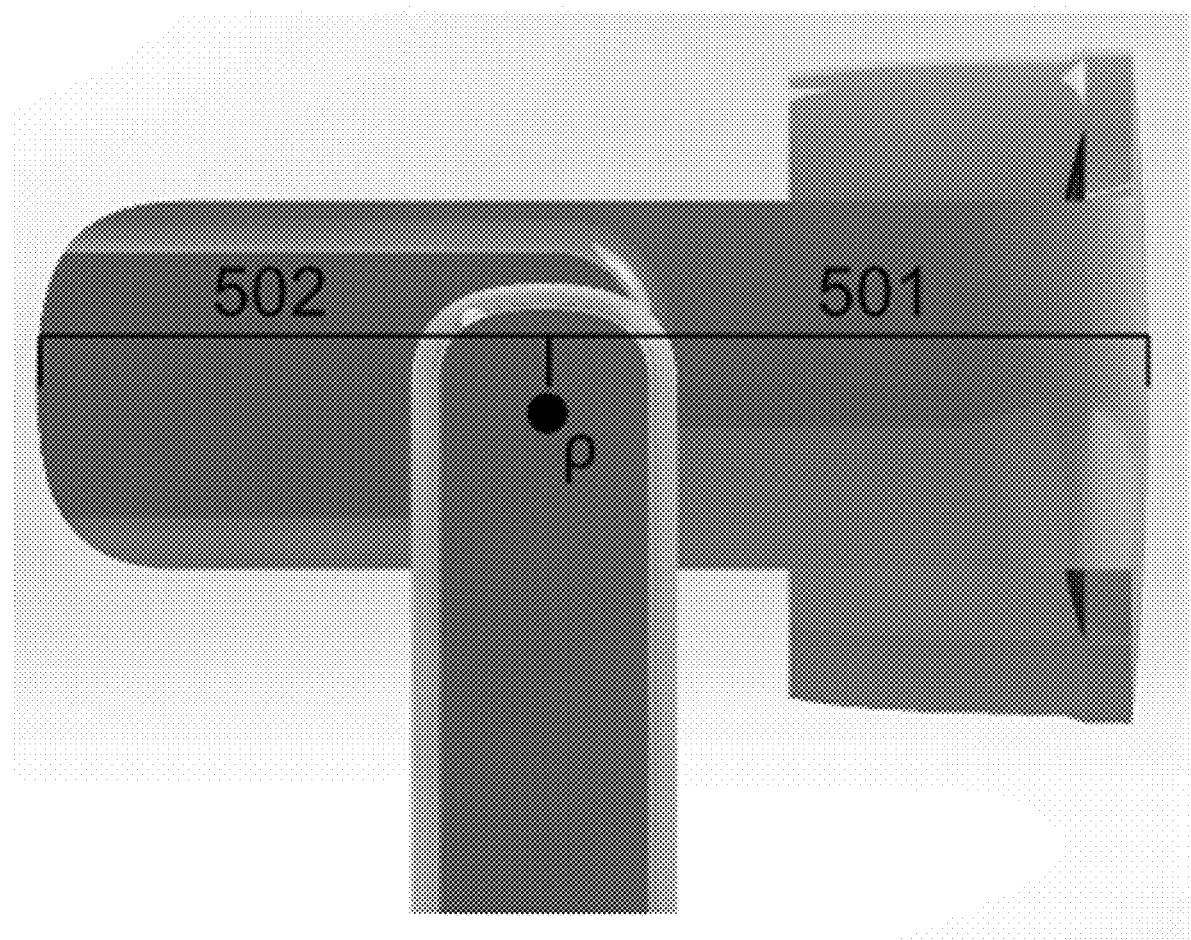
FIG. 5A is a drawing shown in a side view of a multi-axis CT scanner with the gantry in a horizontal position (e.g., a substantially and/or essentially horizontal position). The gantry rotates on the gantry arms around the axis of rotation ρ. The gantry comprises a top portion 501 separated by the axis ρ from a bottom portion 502. The top portion 501 comprises a portion of both gantry arms connected to the scanner ring; the bottom portion 502 comprises a portion of both gantry arms.
Figure 5B:
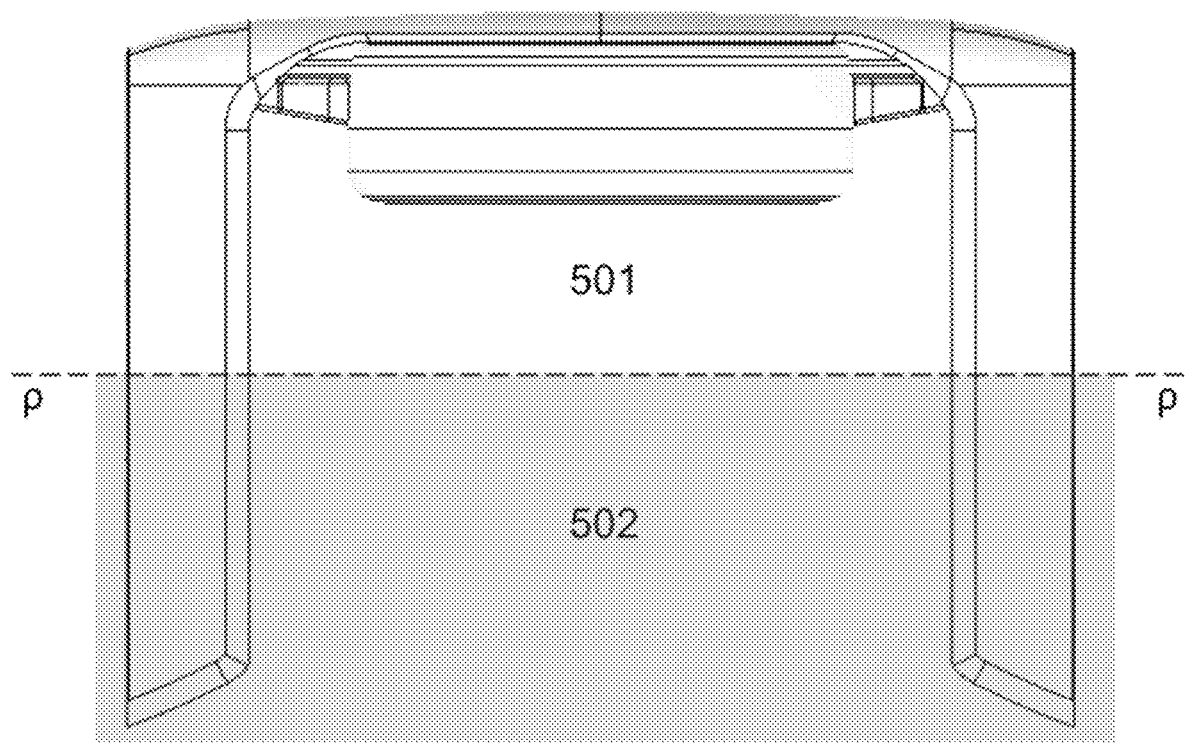
FIG. 5B is a drawing shown in a front view of a multi-axis CT scanner with the gantry in a vertical position (e.g., a substantially and/or essentially vertical position). The gantry rotates on the gantry arms around the axis of rotation ρ. The gantry comprises a top portion 501 separated by the axis β from a bottom portion 502. The top portion 501 is the portion of the gantry above the axis ρ in the drawing and comprises a portion of both gantry arms and the scanner ring. The bottom portion 502 is the portion of the gantry below the axis ρ, within the gray shaded box, that comprises a portion of both gantry arms.

For example, as shown in FIG. 5A and FIG. 5B, in some embodiments, the gantry is balanced around the axis of rotation p so that the torque applied by gravity to the mass of the top portion 501 of the gantry is equal to (e.g., substantially and/or essentially equal to) the torque applied by gravity to the mass of the bottom portion 502 of the gantry. In some embodiments, the ratio of the torque applied by gravity to the mass of the top portion 501 of the gantry is to the torque applied by gravity to the mass of the bottom portion 502 of the gantry is approximately 3:1, 2.5:1, 2:1, 1:1, 1:2, 1:2.5, or 1:3.

In some embodiments, each gantry arm comprises a counterweight within the bottom portion of the gantry (e.g., the bottom portion 502 of the gantry in the shaded region of FIG. 5B) to provide sufficient mass to counterbalance the mass of the top portion 501 of the gantry. Accordingly, a small force (e.g., a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N)) is needed to rotate the gantry. In some embodiments, the force is applied by a motor (e.g., a rotary motor). In some embodiments, the force is applied by a human operator of the multi-axis CT scanner (e.g., by applying a manual force on the gantry to rotate it). In some embodiments, the force is applied by a combination of a motor and a human.

In some embodiments, the scanner ring is counterbalanced with a counterweight associated with (e.g., inside and/or outside) a gantry arm in a single-gantry apparatus or with one or both of the gantry arms in a two-gantry arm apparatus. For example, in some embodiments, the scanner ring has a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms) and is counterbalanced with a counterweight having a mass of approximately 1000 kilograms (e.g., approximately 900, 910, 920, 930, 940, 950, 960, 970, 980, 990, 1000, 1010, 1020, 1030, 1040, 1050, 1060, 1070, 1080, 1090, or 1100 kilograms). The technology is not limited to a mass of scanner ring and counterweight that is in a ratio of approximately 1:1. Accordingly, the technology comprises embodiments in which the scanner ring and counterweight have masses in a ratio of approximately 3:1, 2.5:1, 2:1, 1:1, 1:2, 1:2.5, or 1:3.

In some embodiments, a belt and pulley system is used to attach the scanner ring to the counterweights, e.g., to coordinate movement of the scanner ring mass and the counterweight mass. In some embodiments, a rotary motor is used to translate the scanner ring. In some embodiments, a ball screw is used to translate the scanner ring. Accordingly, a small force (e.g., a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N)) is needed to translate the scanner ring. In some embodiments, the force is applied by a motor (e.g., a rotary motor, a motor coupled to a ball screw). In some embodiments, the force is applied by a human operator of the multi-axis medical imaging apparatus (e.g., by applying a manual force on the scanner ring to translate it). In some embodiments, the force is applied by a combination of a motor and a human.

Figure 6:
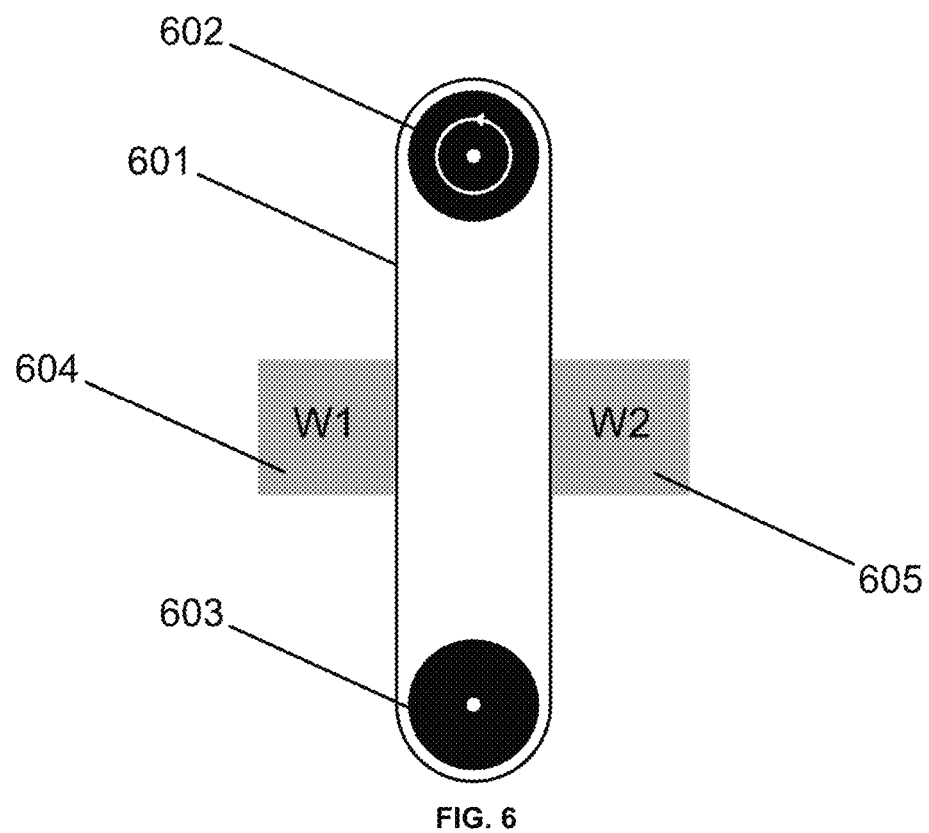
FIG. 6 is a schematic drawing of an embodiment scanner ring counterweight system. comprising a belt 601, a motor 602, a pulley 603, a first weight (W1) 604, and a second weight (W2) 605 representing the scanner ring.

For example, e.g., as shown in FIG. 6, embodiments of a scanner ring counterweight system comprise a belt 601, a motor 602, a pulley 603, a first weight (W1) 604, and a second weight (W2) 605. The first weight (W1) 604 is attached to the belt 601 and provides a counterweight having a mass equal to (e.g., substantially and/or essentially equal to) the mass of the scanner ring, represented by the second weight (W2) 605 that is attached to the belt 601. The scanner ring is translated by action of the motor 602. The first weight (W1) 604 is associated with one or both gantry arms and may be inside or outside the gantry arms. Further, the first weight (W1) 604 may be distributed equally or unequally between the gantry arms.

Figure 7:
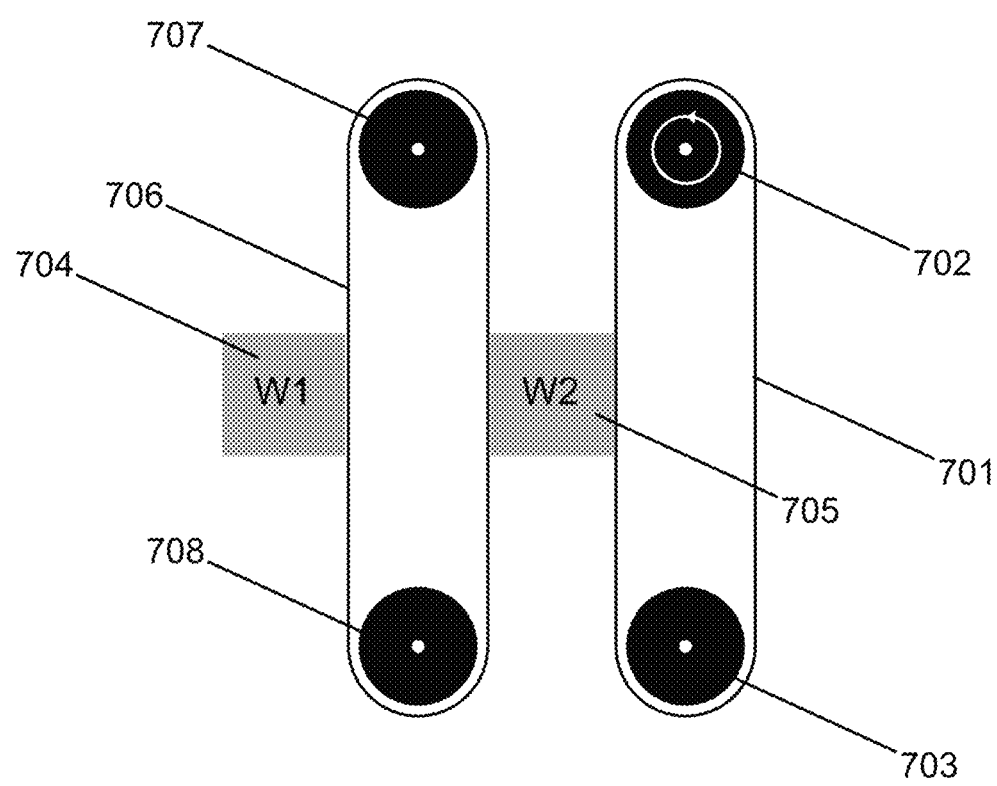
FIG. 7 is a schematic drawing of an embodiment of a scanner ring counterweight system comprising a first belt 701, a motor 702, a first pulley 703, a first weight (W1) 704, a second weight (W2) 705 representing the scanner ring, a second belt 706, a second pulley 707, and a third pulley 708.

As a further example, e.g., as shown in FIG. 7, embodiments of a scanner ring counterweight system comprise a first belt 701, a motor 702, a first pulley 703, a first weight (W1) 704, a second weight (W2) 705, a second belt 706, a second pulley 707, and a third pulley 708. The first weight (W1) 704 is attached to the second belt 706 and is a counterweight having a mass equal to (e.g., substantially and/or essentially equal to) the mass of the scanner ring, represented by the second weight (W2) 705 that is attached to the first belt 701 and the second belt 706. The scanner ring is translated by action of the motor 702. The first weight (W1) 704 is associated with one or both gantry arms and may be inside or outside the gantry arms. Further, the first weight (W1) 704 may be distributed equally or unequally between the gantry arms.

Figure 8:
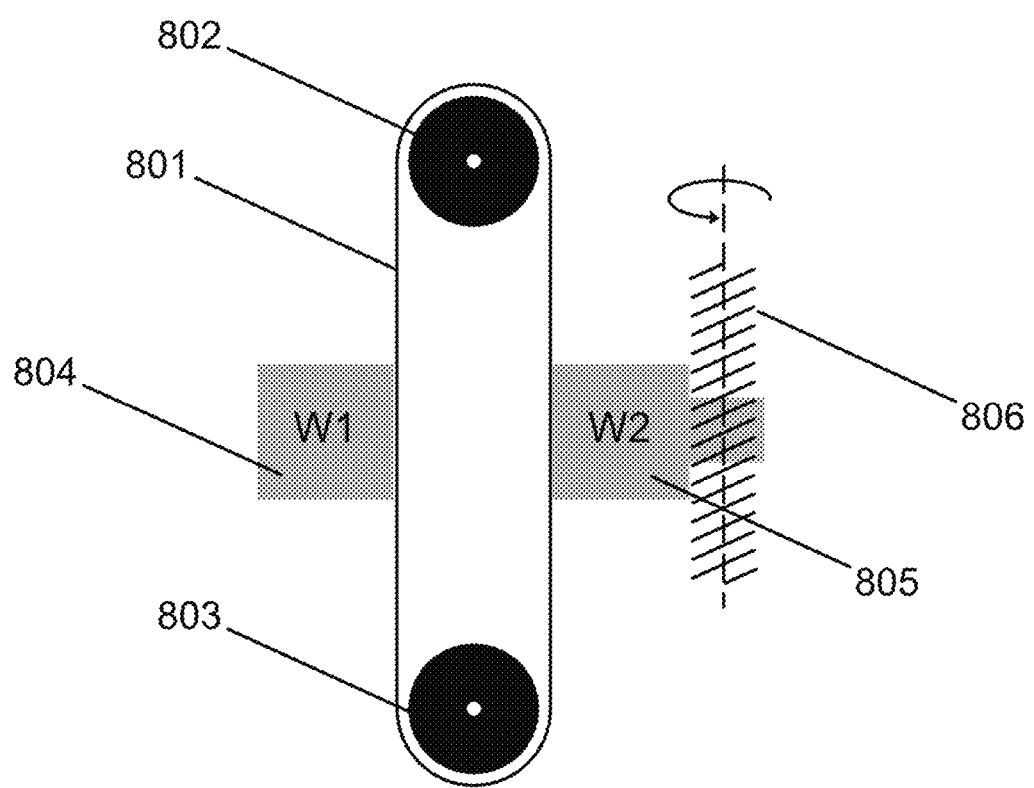
FIG. 8 is a schematic drawing of an embodiment of a scanner ring counterweight system comprising a belt 801, a motor 802, a pulley 803, a first weight (W1) 804, a second weight (W2) 805 representing the scanner ring, and a ball screw 806 that turns on an axis represented by the dashed line.

As yet another example, e.g., as shown in FIG. 8, embodiments of a scanner ring counterweight system comprise a belt 801, a motor 802, a pulley 803, a first weight (W1) 804, a second weight (W2) 805, and a motor coupled to a ball screw 806 (e.g., comprising a threaded shaft and a ball assembly). The first weight (W1) 804 is attached to the belt 801 and is a counterweight having a mass equal to (e.g., substantially and/or essentially equal to) the mass of the scanner ring, represented by the second weight (W2) 805 that is attached to the belt 801. The scanner ring is translated by action of the motor coupled to the ball screw 806, e.g., that turns on an axis represented by the dashed line. The threaded shaft of the ball screw is driven by a motor to turn the threaded shaft an axis represented by the dashed line. The threaded shaft engages with a ball assembly operationally attached to the scanner ring. Rotation of the threaded shaft causes translation of the ball assembly and scanner ring. In some embodiments, the ball screw comprises a threaded shaft having a diameter of 15-100 mm (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100). In some embodiments, the ball screw provides a translation of the scanner ring of 5-100 mm/revolution (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mm/revolution). The first weight (W1) 804 is associated with one or both gantry arms and may be inside or outside the gantry arms. Further, the first weight (W1) 804 may be distributed equally or unequally between the gantry arms.

In some embodiments, friction and electrical resistance provided by the motor and mechanical components used to move the scanner (e.g., ball screw, belt and pulley system, etc.) introduce approximately 30 N of resistance (e.g., approximately 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, or 35.0 N) that are overcome by the force applied to move the scanner ring (e.g., a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N)). One of ordinary skill in the art understands that the pitch of the screw in a ball screw embodiment and/or the size of the motor can be varied to change (e.g., increase or decrease) the friction and resistance provided by the motor and mechanical components and thus the force used to rotate the gantry and/or to translate the scanner ring.

In some embodiments, e.g., as shown in FIGS. 15A, 15B, 16A, 16B, 17A, 17B, 18A, and 18B, the technology provides a multi-axis medical imaging apparatus (e.g., a CT scanning apparatus) comprising a single stanchion, a gantry comprising a gantry arm, a scanner ring, and a counterweight (e.g., provided by a supplemental mass), e.g., to provide counterbalancing.

The technology is not limited to embodiments comprising counterweighting and/or counterbalancing. Accordingly, in some embodiments, the technology provides a multi-axis imaging apparatus (e.g., a computerized tomography (CT) apparatus, a magnetic resonance imaging (MRI) apparatus, a positron emission tomography (PET) apparatus, a single-photon emission computerized tomography (SPECT) apparatus, a photon counting computed tomography apparatus, or a portal imaging apparatus) that is counterbalancing-free and/or counterweighing-free (e.g., the multi-axis imaging apparatus does not comprise counterweighting and/or the multi-axis imaging apparatus does not comprise counterbalancing). In some embodiments of the multi-axis imaging apparatus that does not comprise counterweighting and/or does not comprise counterbalancing, a motor or motor-assisted human applies a force to rotate and/or translate the imaging apparatus.

Furthermore, the technology comprises use of other drive technologies and methods, e.g., belts, screws, chains, pulleys, rods, gears, hydraulics, etc.

Methods

In some embodiments, the technology provides methods for obtaining a medical image (e.g., a CT scan, a magnetic resonance imaging (MRI) scan, a positron emission tomography (PET) scan, a single-photon emission computerized tomography (SPECT) scan, a photon counting computed tomography scan, or a portal image or scanogram (e.g., scanned projection radiography image). While exemplary methods are described for obtaining a CT scan, the technology is not limited to methods for obtaining a CT scan and includes embodiments for obtaining other types of medical images.

In some embodiments, methods comprise providing a multi-axis CT scanner as described herein or a rapid multi-axis computed tomography (RMACT) scanner as described herein. For example, in some embodiments, methods comprise providing a multi-axis CT scanner comprising a first stanchion, a second stanchion, a gantry comprising a first gantry arm and a second gantry arm, and a scanner ring (see, e.g., FIG. 1B). In some embodiments, methods comprise providing a multi-axis CT scanner comprising a single stanchion, a gantry comprising a gantry arm, and a scanner ring. See, e.g., FIGS. 15A, 15B, 16A, 16B, 17A, 17B, 18A, and 18B.

Figure 4C:
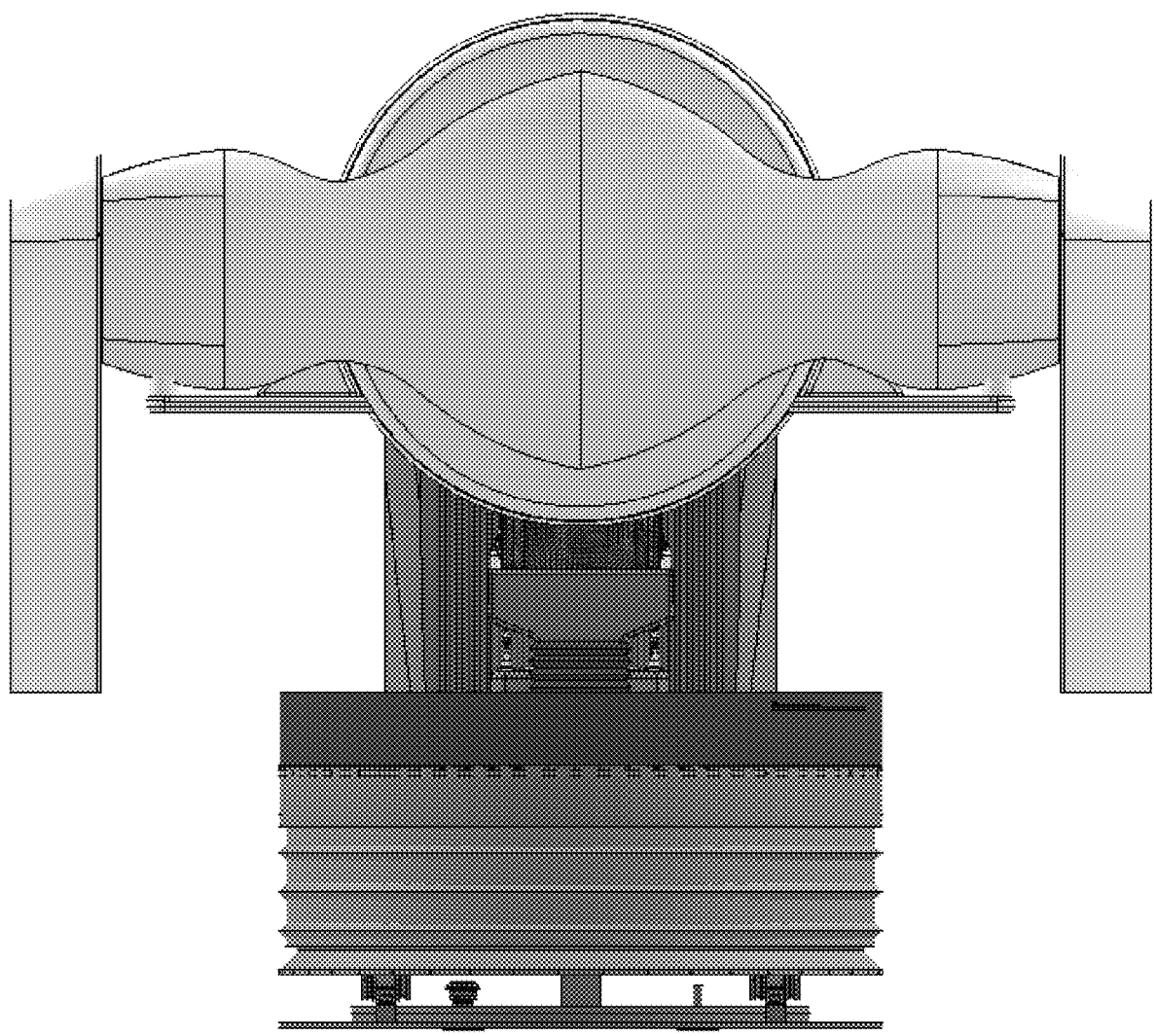
FIG. 4C is a drawing shown in a rear view of a multi-axis CT scanner with the gantry in a horizontal position.
Figure 4D:
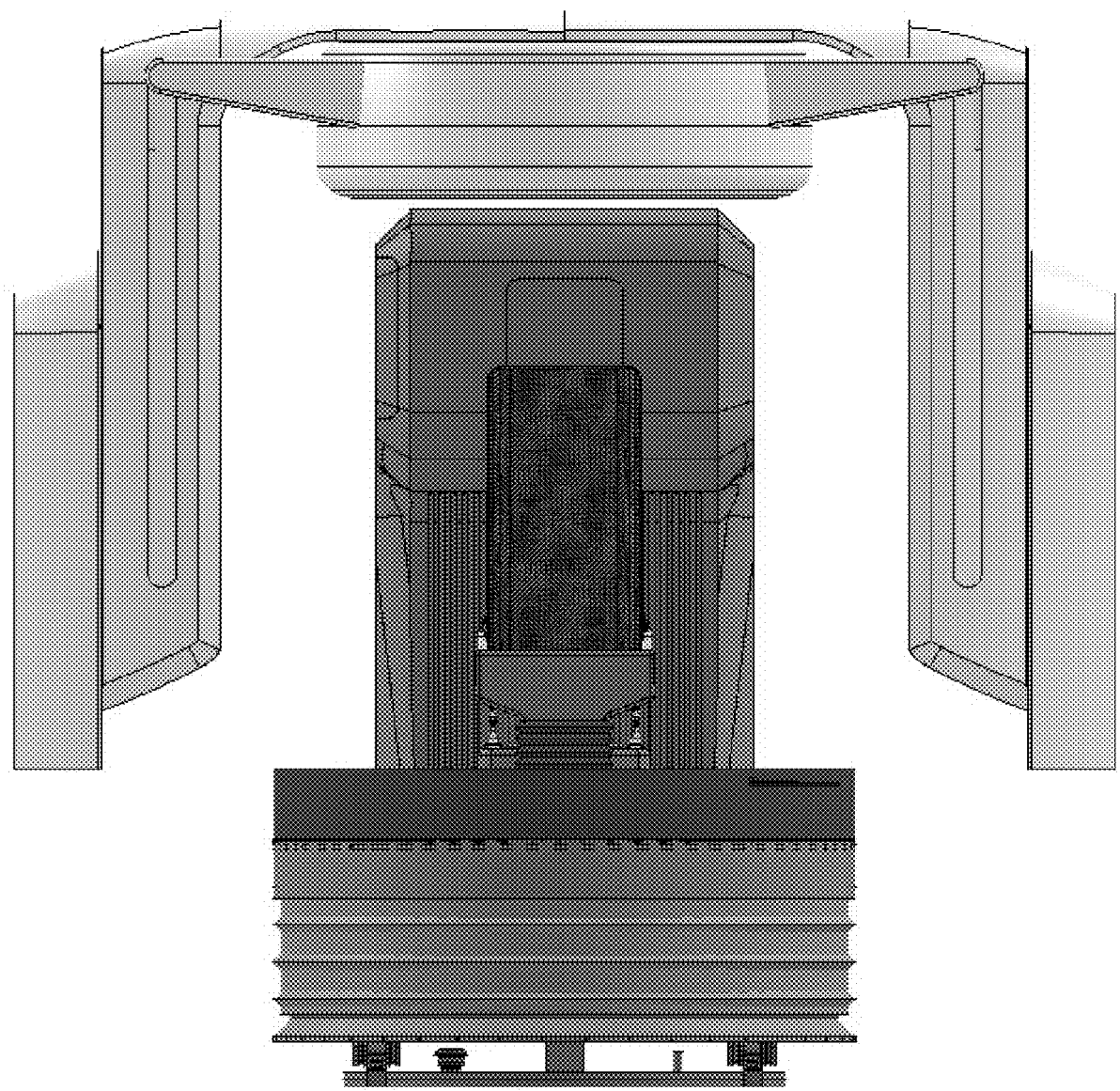
FIG. 4D is a drawing shown in a front view of a multi-axis CT scanner with the gantry in a vertical position.
Figure 4E:
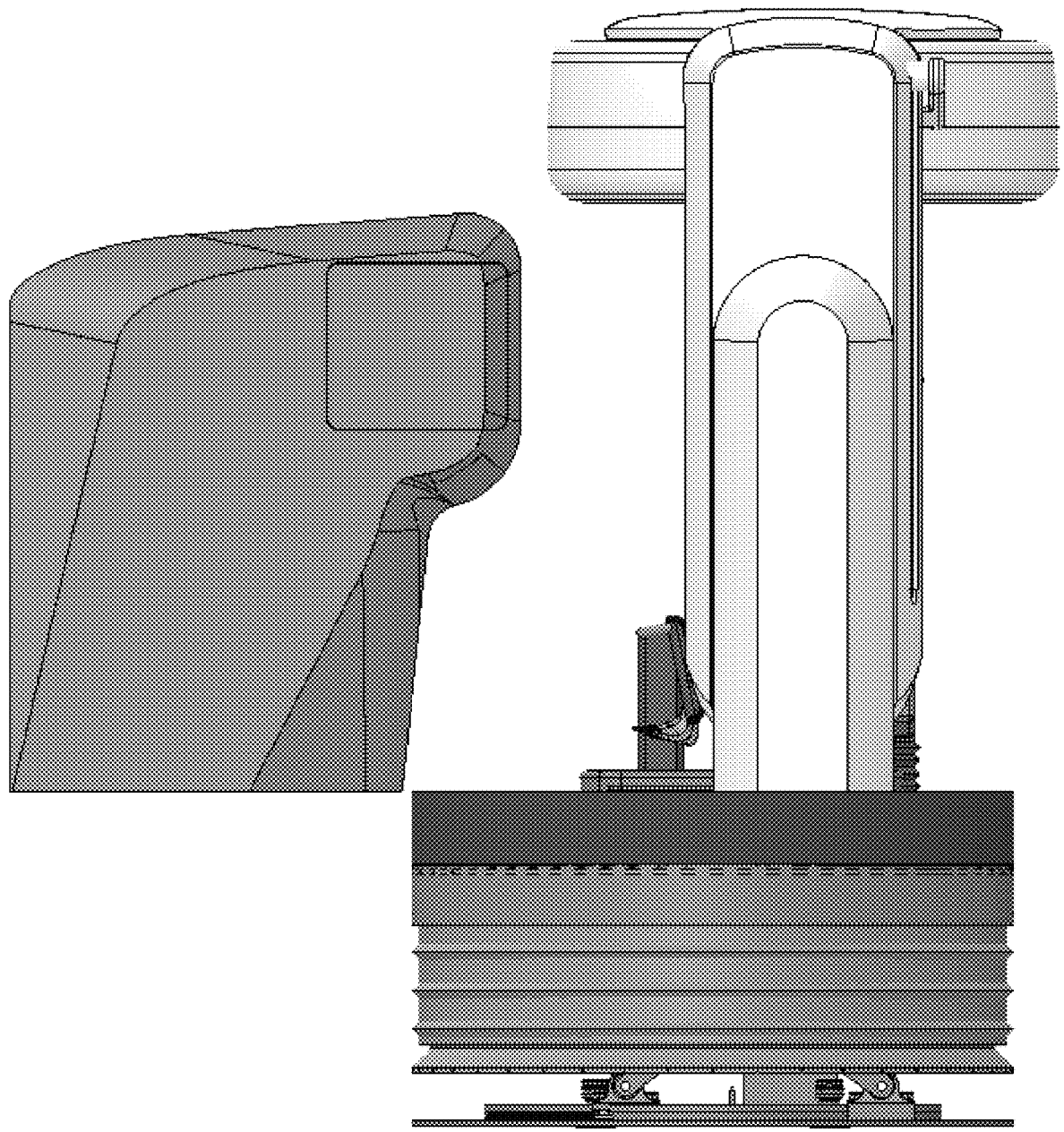
FIG. 4E is a drawing shown in a side view of a multi-axis CT scanner with the gantry in a vertical position.
Figure 4F:
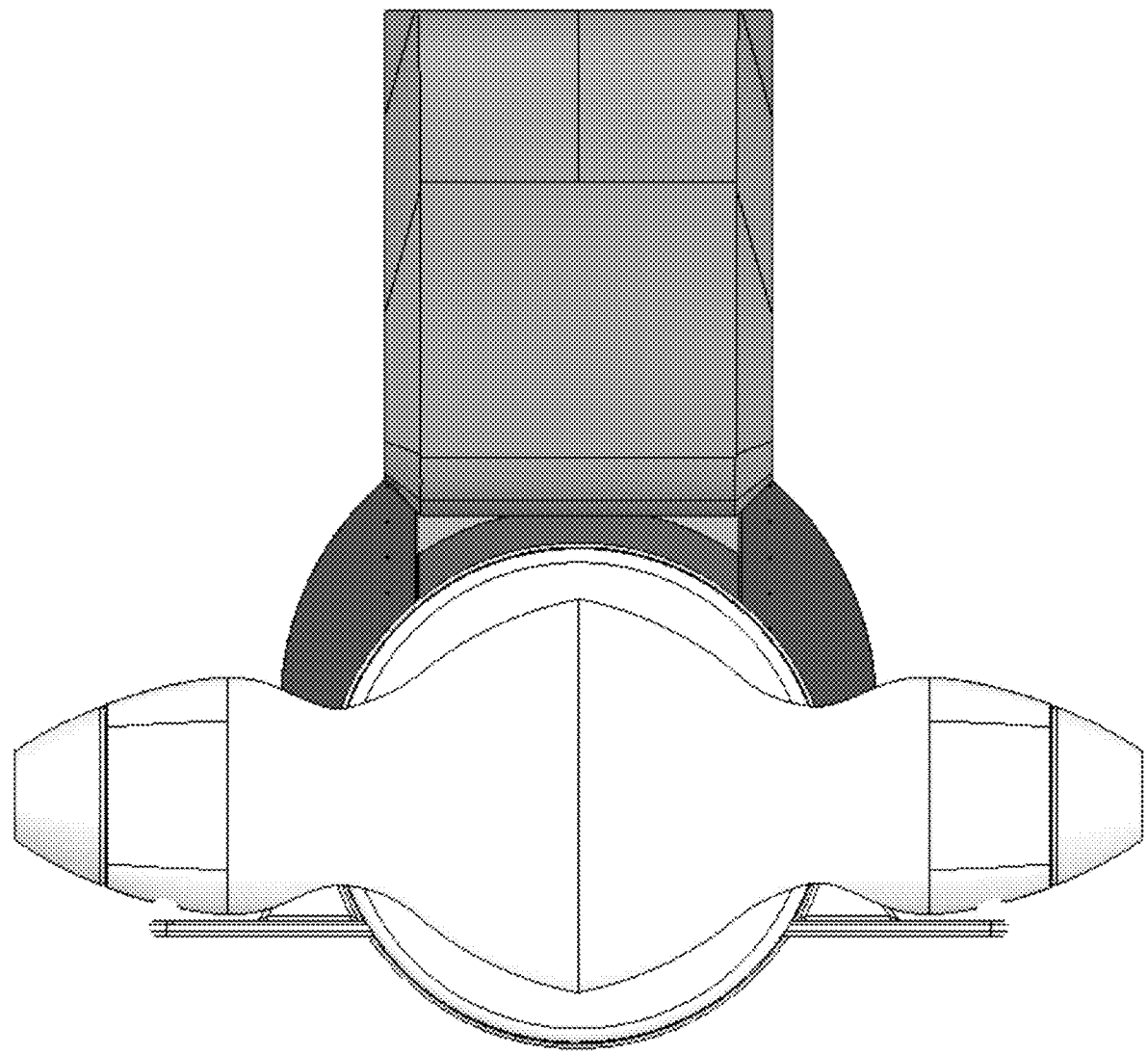
FIG. 4F is a drawing shown in a top view of a multi-axis CT scanner with the gantry in a vertical position.

In some embodiments, the gantry is structured to rotate with respect to the stanchions and/or the scanner ring is structured to translate with respect to the gantry arms. See, e.g., FIG. 4C showing a rear view of a multi-axis CT scanner with the gantry in a horizontal position and FIG. 4D showing a front view of a multi-axis CT scanner with the gantry in a vertical position. As shown in FIG. 4D, providing the gantry in a vertical position allows scanning a patient positioned in a vertical position. Accordingly, in some embodiments, methods comprise scanning a patient in a vertical position. FIG. 4E and FIG. 4F show a multi-axis CT scanner with the gantry in a vertical position.

In some embodiments, the multi-axis CT scanner comprises a gantry that counterbalances the scanner ring and a top portion of the gantry with a bottom portion of the gantry with respect to the axis of rotation of the gantry. In some embodiments, the multi-axis CT scanner comprises a counterweight for translation of the scanner ring.

Figure 2:
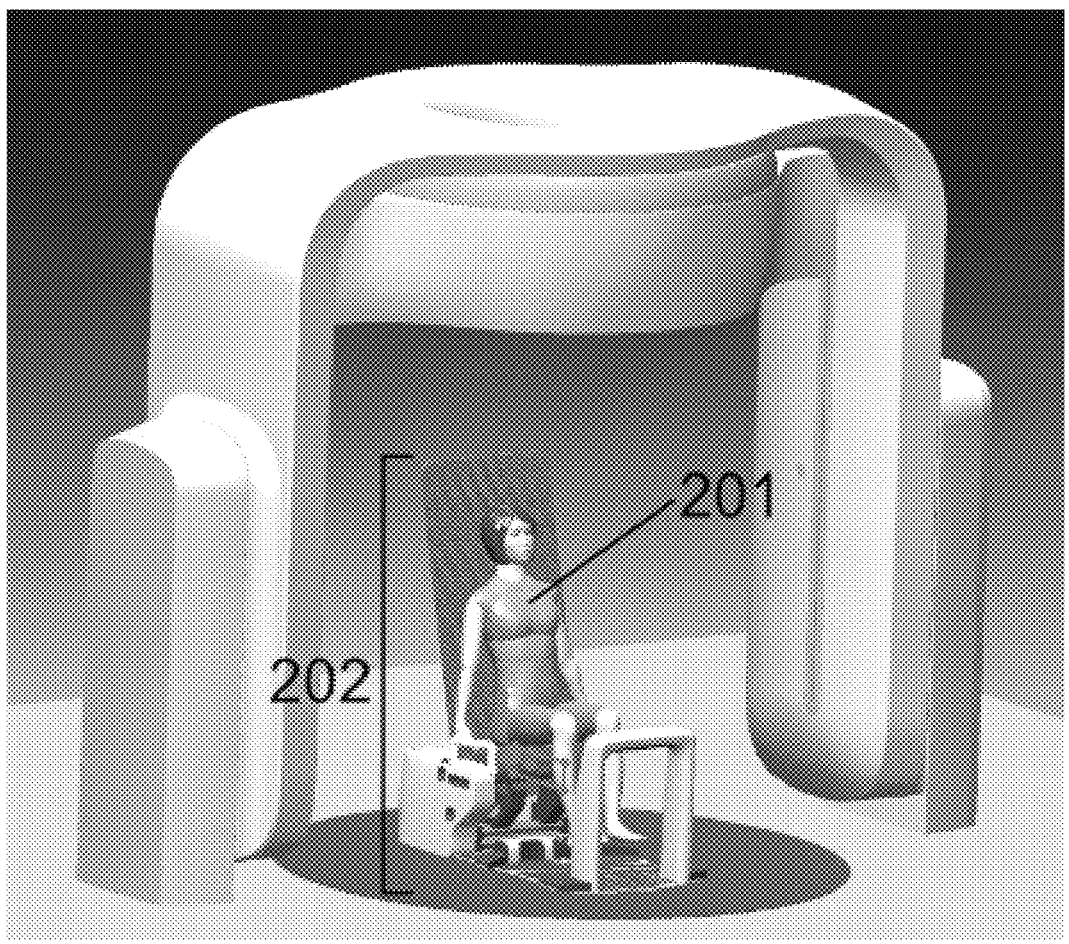
FIG. 2 is a drawing showing a patient 201 sitting in a patient positioning system 202. In some embodiments, methods comprise providing a multi-axis CT scanner and placing a patient 201 within the scan volume of the multi-axis CT scanner. In some embodiments, methods comprise placing a patient 201 on a patient positioning system 202 that is provided within the scan volume of the multi-axis CT scanner.

In some embodiments, methods comprise positioning a patient. In some embodiments, e.g., as shown in FIG. 2, positioning a patient comprises positioning a patient 201 using a patient positioning system 202 (e.g., as described in Int'l Pat. App. Pub. No. WO 2019/056055, in U.S. Pat. App. Pub. No. 2020/0268327, and in and in U.S. Pat. App. Ser. No. 63/237,513, each of which is incorporated herein by reference). In some embodiments, the patient is in a vertical position and methods comprise providing a patient in a vertical position. In some embodiments, the patient is standing (e.g., standing, standing and leaning backward, standing and leaning forward, perched, etc.) and methods comprise providing a patient in a standing (e.g., standing, standing and leaning backward, standing and leaning forward, perched, etc.) position. In some embodiments, the patient is sitting (e.g., seated, seated and leaning backward, seated and leaning forward, etc.) and methods comprise providing a patient in a sitting (e.g., seated, seated and leaning backward, seated and leaning forward, etc.) position. In some embodiments, the patient is kneeling (e.g., kneeling, kneeling and leaning forward, or kneeling and leaning backward), and methods comprise providing a patient in a kneeling (kneeling, kneeling and leaning forward, or kneeling and leaning backward) position. In some embodiments, methods comprise providing a patient positioning system and/or patient support to hold a patient in a vertical position (e.g., seated, seated and leaning backward, seated and leaning forward, standing, standing and leaning backward, standing and leaning forward, perched, kneeling, kneeling and leaning forward, or kneeling and leaning backward, or other vertical or substantially vertical position). See, e.g., Int'l Pat. App. Pub. No. WO 2019/056055, in U.S. Pat. App. Pub. No. 2020/ 0268327, and in and in U.S. Pat. App. Ser. No. 63/237,513, each of which is incorporated herein by reference.

In some embodiments, methods comprise providing a multi-axis CT scanner and placing a patient 201 within the scan volume of the multi-axis CT scanner. In some embodiments, methods comprise placing a patient 201 on a patient positioning system 202 that is provided within the scan volume of the multi-axis CT scanner.

Figure 3A:
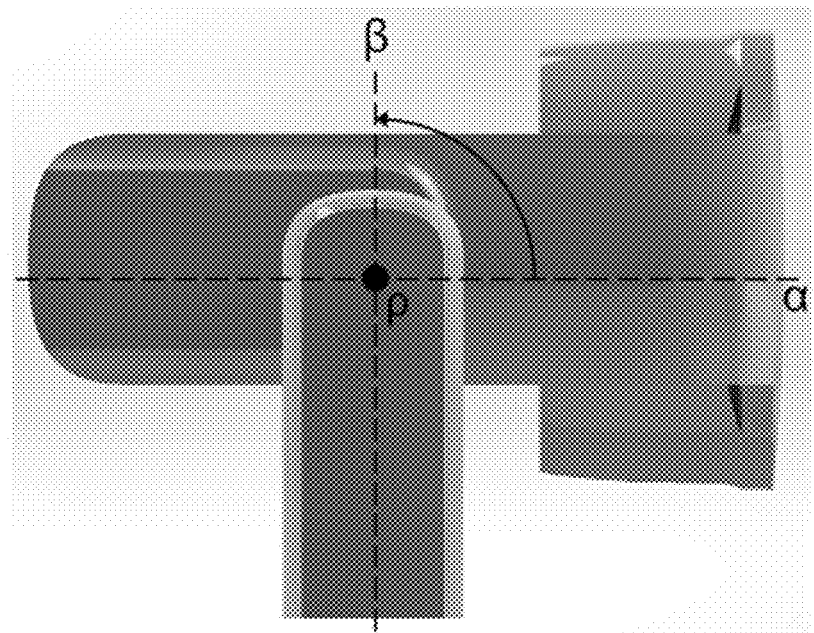
FIG. 3A is a drawing shown in a side view of a multi-axis CT scanner. The gantry is shown in a horizontal position (e.g., a substantially and/or essentially horizontal position), e.g., aligned with axis α. In some embodiments of the technology, methods comprise rotating the gantry and scanner ring around an axis of rotation (e.g., axis ρ) to provide the gantry in a vertical position (e.g., a substantially and/or essentially vertical position), e.g., aligned with axis β. In some embodiments, axis α is parallel (e.g., substantially and/or essentially parallel) to the floor. In some embodiments, axis β is perpendicular (e.g., substantially and/or essentially perpendicular) to the floor.
Figure 3B:
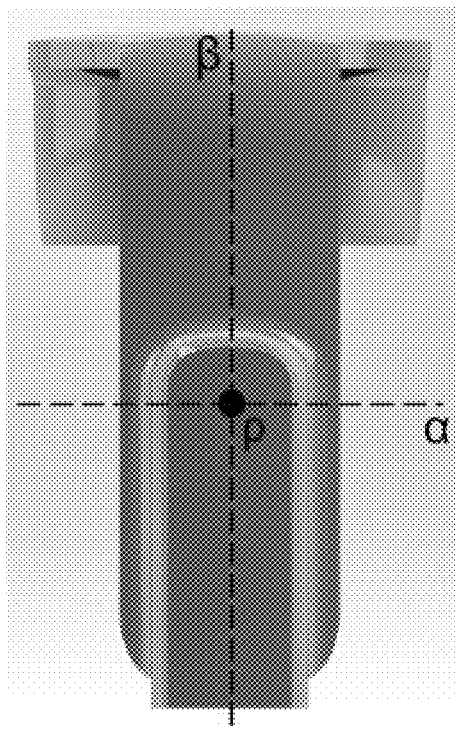
FIG. 3B is a drawing shown in a side view of a multi-axis CT scanner. The gantry is shown in a vertical position and/or substantially vertical position, e.g., aligned with axis β. In some embodiments, methods comprise rotating the gantry and scanner ring around an axis of rotation (e.g., ρ) to provide the gantry in a vertical and/or substantially vertical position, e.g., aligned with axis β. The axis of rotation p is normal to the plane of the page and perpendicular (e.g., substantially and/or essentially perpendicular) to both axis α and axis β. For example, method embodiments comprise rotating the gantry from a horizontal position (e.g., from a position aligned with axis α) around an axis of rotation (e.g., axis ρ) to a vertical position (e.g., to a position aligned with axis β).

In some embodiments, e.g., as shown in FIG. 3A and FIG. 3B, methods comprise rotating the gantry. In some embodiments, rotating the gantry comprises rotating the gantry around an axis ρ relative to the first stanchion and/or the second stanchion. In some embodiments, e.g., as shown in FIG. 3A and FIG. 3B, methods comprise rotating the gantry from a horizontal position (e.g., a substantially and/or essentially horizontal position) to a vertical position (e.g., substantially and/or essentially vertical position), e.g., a rotation of approximately 90°. For example, in some embodiments, methods comprise rotating the gantry from a position in which the gantry arms are parallel with (e.g., substantially and/or essentially parallel with) axis α shown as in FIG. 3A to a position in which the gantry arms are parallel with (e.g., substantially and/or essentially parallel with) axis β as shown in FIG. 3B. In some embodiments, axis α is parallel (e.g., substantially and/or essentially parallel) to the floor. In some embodiments, axis β is perpendicular (e.g., substantially and/or essentially perpendicular) to the floor. In some embodiments, methods comprise rotating the gantry to align the long axis of the gantry arms to be parallel with (e.g., substantially and/or essentially parallel with) the spine of the patient. For example, in some embodiments, axis β as shown in FIG. 3B is parallel with (e.g., substantially and/or essentially parallel with) the spine of the patient. The technology is not limited to rotations of approximately 90° (e.g., substantially and/or essentially 90°) as shown in FIG. 3A and FIG. 3B. Accordingly, the technology encompasses rotating the gantry through any angle (e.g., 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees). In some embodiments, e.g., as shown in FIG. 3A and FIG. 3B, the axis α and/or the axis β is/are or can be provided at any angle in the plane of the page, e.g., rotated around axis ρ relative to the positions of axis α and/or axis β shown in FIG. 3A or 3B.

In some embodiments, rotating the gantry comprises activating a motor to apply a force to rotate the gantry. In some embodiments, rotating the gantry comprises manually pushing and/or pulling the gantry to rotate it. In some embodiments, methods comprise applying a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) to rotate the gantry, e.g., using a motor and/or using manual force. That is, in some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor.

Figure 3C:
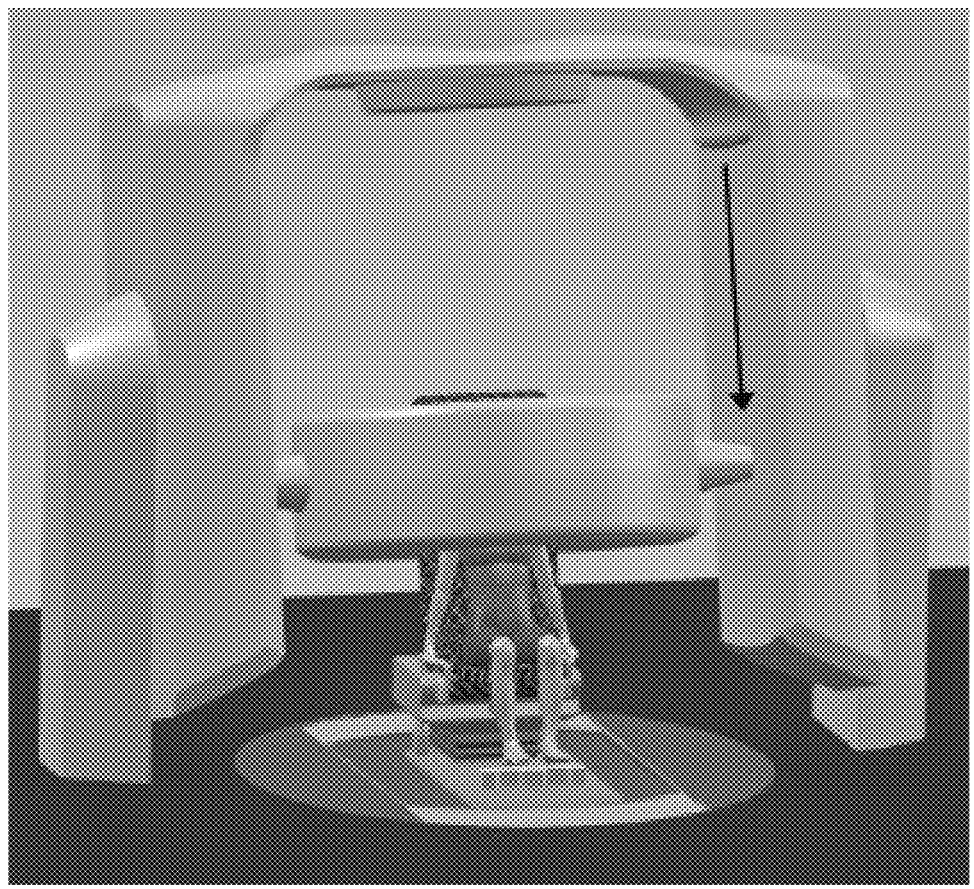
FIG. 3C is a drawing shown in a front view of a multi-axis CT scanner. The gantry is shown in a vertical position (e.g., substantially and/or essentially vertical position). A patient is shown sitting in a patient positioning system (see, e.g., FIG. 2). In some embodiments, methods comprise translating the scanner ring from a first position (e.g., as shown in FIG. 2) to a second position (e.g., as shown in FIG. 3C). The scanner ring in the second position provides a CT scanner for obtaining a CT scan of a region of interest of the patient. The technology is not limited to rotations of 90° (e.g., substantially and/or essentially 90°) as shown in FIG. 3A and FIG. 3B. Accordingly, the technology encompasses positioning the scanner ring along any axis that is perpendicular to the axis of rotation ρ. In some embodiments, the axis α and/or the axis β is/are or can be provided at any angle in the plane of the page, e.g., rotated around axis ρ relative to the positions of axis α and/or axis β shown in FIG. 3A and/or FIG. 3B.

In some embodiments, e.g., as shown in FIG. 3C, methods comprise translating the scanner ring, e.g., from a first position away from the patient (e.g., as shown in FIG. 2) to a second position where the scanner ring surrounds the patient and/or the patient positioning system (e.g., as shown in FIG. 3C). In some embodiments, translating the scanner ring comprises translating the scanner ring along an axis of translation (T) that is parallel (e.g., substantially and/or essentially parallel) to the long dimension of the gantry arms. In some embodiments, the scanner ring is translated approximately 0.20 to 2.00 m (e.g., 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, or 2.00 m).

In some embodiments, the gantry is in a vertical position (e.g., substantially and/or essentially vertical position) when the scanner ring is translated. In some embodiments, the gantry is in a horizontal position (e.g., substantially and/or essentially horizontal position) when the scanner ring is translated (e.g., to obtain a CT scan of a lying patient). In some embodiments, the gantry is at an angle of 0-200 degrees (e.g., 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 degrees) with respect to the floor when the scanner ring is translated.

In some embodiments, translating the scanner ring comprises activating a motor to apply a force to translate the scanner ring. In some embodiments, translating the scanner ring comprises activating a rotatory motor to drive a belt or chain attached to the scanner ring. In some embodiments, translating the scanner ring comprises activating a motor coupled to a ball screw operationally coupled to the scanner ring. In some embodiments, the ball screw comprises a threaded shaft having a diameter of 15-100 mm (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100). In some embodiments, the ball screw provides a translation of the scanner ring of 5-100 mm/revolution (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mm/revolution).

In some embodiments, translating the scanner ring comprises manually pushing and/or pulling the scanner ring to translate it. In some embodiments, methods comprise applying a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) to translate the scanner ring, e.g., using a motor and/or using manual force. That is, in some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor.

In some embodiments, methods comprise translating the multi-axis CT scanner in the plane of the floor. For example, in some embodiments, methods comprise translating the multi-axis CT scanner (e.g., by translating one or both stanchions) in the X-Y plane (e.g., in the plane of the floor), e.g., to position the scanner ring with respect to a patient and/or a region of interest of a patient (see, e.g., FIG. 4A and FIG. 4B and the three-dimensional coordinate system showing the X-Y plane for reference).

In some embodiments, methods comprise obtaining (e.g., acquiring, recording, etc.) a medical image. In some embodiments, comprise obtaining (e.g., acquiring, recording, etc.) a CT image, MRI image, PET image, SPECT image, photon counting computed tomography image, or a portal image or scanned projection radiography image (e.g., "scout" scan). In some embodiments, methods comprise activating an imaging source (e.g., electromagnetic radiation source, X-ray source, gamma ray source, radio wave source, photon source, proton source, positron source, gamma ray source (e.g., gamma rays from a positron source)). In some embodiments, methods comprise activating an imaging detector (e.g., electromagnetic radiation detector, X-ray detector, photon detector, gamma ray detector), e.g., detecting electromagnetic radiation, X-rays, gamma rays, radio waves, photons, protons, positrons, etc. using the detector.

In some embodiments relating to CT scanning methods, methods comprise generating X-rays using an X-ray generator of the scanner ring. In some embodiments, methods comprise detecting X-rays using an X-ray detector of the scanner ring. In some embodiments, methods comprise revolving an X-ray generator and an opposed X-ray detector around the patient. In some embodiments, methods comprise revolving an X-ray generator and an opposed X-ray detector around the patient while the scanner ring is stationary with respect to the gantry arms. In some embodiments, methods comprise revolving an X-ray generator and an opposed X-ray detector around the patient while the scanner ring moves with respect to the gantry arms.

In some embodiments, methods comprise reversing the translating and rotating steps above to move the scanner ring and/or gantry, e.g., allow the patient to exit the medical imaging apparatus (e.g., CT scanner). For example, in some embodiments, methods comprise translating the scanner ring, e.g., to a position where the scanner ring does not surround the patient and/or the patient positioning system. In some embodiments, methods comprise rotating the gantry to a horizontal position (e.g., substantially and/or essentially horizontal position). In some embodiments, translating the scanner ring away from the patient and/or rotating the gantry to a horizontal position comprises applying a force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) to the scanner ring and/or gantry, respectively. In some embodiments, the force of 50 N or less (e.g., less than 50.0, 49.5, 49.0, 48.5, 48.0, 47.5, 47.0, 46.5, 46.0, 45.5, 45.0, 44.5, 44.0, 43.5, 43.0, 42.5, 42.0, 41.5, 41.0, 40.5, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.5, 30.0, 29.5, 29.0, 28.5, 28.0, 27.5, 27.0, 26.5, 26.0, 25.5, 25.0, 24.5, 24.0, 23.5, 23.0, 22.5, 22.0, 21.5, 21.0, 20.5, 20.0, 19.5, 19.0, 18.5, 18.0, 17.5, 17.0, 16.5, 16.0, 15.5, 15.0, 14.5, 14.0, 13.5, 13.0, 12.5, 12.0, 11.5, 11.0, 10.5, or 10.0 N) is provided by a human, by a motor, or by a combination of a human and a motor. In some embodiments, translating the scanner ring away from the patient and/or rotating the gantry to a horizontal position comprises activating a motor to apply a force to translate the scanner ring away from the patient and/or rotate the gantry to a horizontal position. In some embodiments, translating the scanner ring away from the patient and/or rotating the gantry to a horizontal position comprises manually pushing and/or pulling the scanner ring to translate it away from the patient and/or the gantry to rotate it to a horizontal position. In some embodiments, methods comprise translating the scanner ring away from the patient and/or rotating the gantry to a horizontal position by a human user using manual force. In some embodiments, methods comprise translating the scanner ring away from the patient and/or rotating the gantry to a horizontal position by a human user using manual force and without the aid of a motor. For example, in some embodiments, methods comprise translating the scanner ring away from the patient and/or rotating the gantry to a horizontal position by a human user using manual force in the absence of electrical power, e.g., to allow a user to exit the CT scanner in the event of a power outage.

Systems

The technology provides embodiments of systems. For example, the technology provides multi-axis medical imaging systems. In some embodiments, the medical imaging system is a computerized tomography (CT) system, a magnetic resonance imaging (MRI) system, a positron emission tomography (PET) system, a single-photon emission computerized tomography (SPECT) system, a photon counting computed tomography system, or a portal imaging system or scanned projection radiography imaging system. While the technology is described for exemplary embodiments wherein the medical imaging system is a computerized tomography (CT) system, the technology is not limited to a CT scanning system and embodiments are to be understood to include other types of medical imaging systems.

For example, in some embodiments, systems comprise a multi-axis medical imaging apparatus as described herein, e.g., a multi-axis medical imaging apparatus comprising a first stanchion, a second stanchion, a gantry comprising a first gantry arm and a second gantry arm, and a scanner ring (see, e.g., FIG. 1B). In some embodiments, systems comprise a multi-axis medical imaging apparatus as described herein, e.g., a multi-axis medical imaging apparatus comprising a stanchion, a gantry comprising a gantry arm, and a scanner ring (see, e.g., FIGS. 15A, 15B, 16A, 16B, 17A, 17B, 18A, and 18B). In some embodiments, systems comprise a rapid multi-axis computerized tomography system as described herein.

In some embodiments, systems comprise a multi-axis medical imaging apparatus comprising a gantry structured to rotate with respect to the stanchion(s). Accordingly, in some embodiments, systems comprise a multi-axis medical imaging apparatus comprising a motor structured to rotate the gantry with respect to the stanchions. In some embodiments, systems comprise a multi-axis medical imaging apparatus comprising a scanner ring structured to translate with respect to the gantry arm(s). Accordingly, in some embodiments, the multi-axis medical imaging apparatus comprises a motor structured to translate the scanner ring with respect to the gantry arms. In some embodiments, systems comprise a multi-axis medical imaging apparatus comprising a counterbalanced gantry/scanner ring (e.g., a gantry/scanner ring comprising the gantry and scanner ring). In some embodiments, the multi-axis medical imaging apparatus comprises a mass to provide a counterweight for scanner ring translation. In some embodiments, systems comprise a multi-axis medical imaging apparatus comprising a medical imaging source and a detector (e.g., systems comprise a multi-axis medical imaging apparatus comprising a scanner ring that comprises a medical imaging source opposed to a detector, e.g., that move around the scanner ring).

In some embodiments, systems comprise a multi-axis medical imaging apparatus as described herein and a patient positioning system and/or patient support, e.g., as described in Int'l Pat. App. Pub. No. WO 2019/056055, in U.S. Pat. App. Pub. No. 2020/0268327, and in and in U.S. Pat. App. Ser. No. 63/237,513, each of which is incorporated herein by reference.

In some embodiments, systems comprise a multi-axis medical imaging apparatus as described herein and software components and/or hardware components structured to rotate the gantry and/or to translate the scanner ring. In some embodiments, systems comprise software components structured to perform a method as described herein.

In some embodiments, systems comprise a multi-axis medical imaging apparatus, software for obtaining (e.g., recording, acquiring) a medical image, and software for controlling gantry rotation and scanner ring translation.

In some embodiments, systems comprise a multi-axis medical imaging apparatus as described herein and a controller. In some embodiments, the medical imaging source and detector communicate with the controller. In some embodiments, the controller activates the medical imaging source and collects the image projections from the detector. In some embodiments, the controller controls movement of the medical imaging source and detector in opposition around the scanner ring. In some embodiments, the controller communicates with a camera (e.g., a horizontal camera and/or a vertical camera) positioned to obtain an elevational image and/or a plan image of a region occupied by a patient. In some embodiments, the controller communicates with a graphic display terminal for providing output images such as tomographic images, positioning information, and user input devices such as a keyboard for receiving instructions from a user. In some embodiments, the controller has a general computer architecture including one or more processors communicating with a memory for the storage of nontransient control programs (e.g., to store tomographic projection sets and resulting tomographic images).

In some embodiments, systems comprise a multi-axis medical imaging apparatus as described herein, a patient in an upright (e.g., vertical (e.g., substantially and/or essentially vertical position)), and a user who interacts with controls structured to move the multi-axis medical imaging apparatus and acquire medical images of said patient or a portion thereof.

In some embodiments, systems comprise a multi-axis medical imaging apparatus and an imaging subsystem. In some embodiments, a controller controls the imaging subsystem. In some embodiments, the imaging subsystem comprises one or more cameras that record images of objects (e.g., the patient positioning system and/or patient support and/or the patient) within the scanner ring of the multi-axis medical imaging apparatus. In some embodiments, the imaging subsystem comprises one or more cameras provided on the scanner ring of the multi-axis medical imaging apparatus. Accordingly, in some embodiments, systems comprise a multi-axis medical imaging apparatus comprising one or more cameras (e.g., a scanner ring comprising one or more cameras). In some embodiments, the cameras record images that are subsequently processed by software (e.g., configured to perform image recording, image analysis, image storage, image manipulation, and/or image comparison methods) and/or hardware components (e.g., microprocessors, graphics processors, communications buses configured to communicate, record, analyze, store, manipulate, and/or compare images) of the imaging subsystem.

In particular embodiments, systems comprise a multi-axis CT scanner as described herein, e.g., a multi-axis CT scanner comprising a first stanchion, a second stanchion, a gantry comprising a first gantry arm and a second gantry arm, and a scanner ring (see, e.g., FIG. 1B). In particular embodiments, systems comprise a multi-axis CT scanner as described herein, e.g., a multi-axis CT scanner comprising a stanchion, a gantry comprising a gantry arm, and a scanner ring (see, e.g., FIGS. 15A, 15B, 16A, 16B, 17A, 17B, 18A, and 18B). In some embodiments, systems comprise a multi-axis CT scanner comprising a gantry structured to rotate with respect to the stanchions. Accordingly, in some embodiments, systems comprise a multi-axis CT scanner comprising a motor structured to rotate the gantry with respect to the stanchions. In some embodiments, systems comprise a multi-axis CT scanner comprising a scanner ring structured to translate with respect to the gantry arms. Accordingly, in some embodiments, the multi-axis CT scanner comprises a motor structured to translate the scanner ring with respect to the gantry arms. In some embodiments, systems comprise a multi-axis CT scanner comprising a counterbalanced gantry/scanner ring. In some embodiments, the multi-axis CT scanner comprises a mass to provide a counterweight for scanner ring translation. In some embodiments, systems comprise a multi-axis CT scanner comprising an X-ray generator and an X-ray detector (e.g., systems comprise a multi-axis CT scanner comprising a scanner ring that comprises a revolving X-ray generator opposed to a revolving X-ray detector, e.g., that move around the scanner ring).

In some embodiments, systems comprise a multi-axis CT scanner as described herein and a patient positioning system and/or patient support, e.g., as described in Int'l Pat. App. Pub. No. WO 2019/056055, in U.S. Pat. App. Pub. No. 2020/0268327, and in and in U.S. Pat. App. Ser. No. 63/237,513, each of which is incorporated herein by reference.

In some embodiments, systems comprise a multi-axis CT scanner as described herein and software components and/or hardware components structured to rotate the gantry and/or to translate the scanner ring. In some embodiments, systems comprise software components structured to perform a method as described herein.

In some embodiments, systems comprise a multi-axis CT scanner, software for obtaining (e.g., recording, acquiring) a CT scan, and software for controlling gantry rotation and scanner ring translation.

In some embodiments, systems comprise a multi-axis CT scanner as described herein and a controller. In some embodiments, the X-ray generator and X-ray detector communicate with the controller. In some embodiments, the controller activates the X-ray tube and collects the tomographic projections from the X-ray detector. In some embodiments, the controller controls movement of the X-ray generator and X-ray detector in opposition around the scanner ring. In some embodiments, the controller communicates with a camera (e.g., a horizontal camera and/or a vertical camera) positioned to obtain an elevational image and/or a plan image of a region occupied by a patient. In some embodiments, the controller communicates with a graphic display terminal for providing output images such as tomographic images, positioning information, and user input devices such as a keyboard for receiving instructions from a user. In some embodiments, the controller has a general computer architecture including one or more processors communicating with a memory for the storage of non-transient control programs (e.g., to store tomographic projection sets and resulting tomographic images).

In some embodiments, systems comprise a multi-axis CT scanner as described herein, a patient in an upright (e.g., vertical (e.g., substantially and/or essentially vertical position)), and a user who interacts with controls structured to move the multi-axis CT scanner and acquire CT scans of said patient or a portion thereof.

In some embodiments, systems comprise a multi-axis CT scanner and an imaging subsystem. In some embodiments, a controller controls the imaging subsystem. In some embodiments, the imaging subsystem comprises one or more cameras that record images of objects (e.g., the patient positioning system and/or patient support and/or the patient) within the scanner ring of the multi-axis CT scanner. In some embodiments, the imaging subsystem comprises one or more cameras provided on the scanner ring of the multi-axis CT scanner. Accordingly, in some embodiments, systems comprise a multi-axis CT scanner comprising one or more cameras (e.g., a scanner ring comprising one or more cameras). In some embodiments, the cameras record images that are subsequently processed by software (e.g., configured to perform image recording, image analysis, image storage, image manipulation, and/or image comparison methods) and/or hardware components (e.g., microprocessors, graphics processors, communications buses configured to communicate, record, analyze, store, manipulate, and/or compare images) of the imaging subsystem.

In some embodiments, the imaging subsystem is configured to image the patient positioning system and/or patient support (e.g., as described in Int'l Pat. App. Pub. No. WO 2019/056055, in U.S. Pat. App. Pub. No. 2020/0268327, and in and in U.S. Pat. App. Ser. No. 63/237,513, each of which is incorporated herein by reference). In some embodiments, the imaging subsystem is configured to produce a model of the patient positioning system and/or patient support using the images of the patient positioning system. In some embodiments, the imaging subsystem is configured to compare the position and/or configuration of the patient positioning system and/or patient support (e.g., using the model of the patient positioning system and/or patient support) with respect to a preset position and/or configuration of the patient positioning system and/or patient support (e.g., a model and/or parameters stored in a computer-readable medium and provided to a microprocessor for comparison with the model describing the patient positioning system and/or patient support). In some embodiments, the preset position of the patient positioning system and/or patient support provides a patient positioned using the patient positioning system and/or patient support in a vertical position.

In some embodiments, the imaging subsystem is configured to image the patient. In some embodiments, the imaging subsystem is configured to produce a model of the patient using the images of the patient. In some embodiments, the imaging subsystem is configured to compare the position of the patient (e.g., using the model of the patient) with respect to a preset position of the patient (e.g., a model and/or parameters stored in a computer-readable medium and provided to a microprocessor for comparison with the model describing the patient positioning system). In some embodiments, the preset position of the patient provides the patient in a vertical position. In some embodiments, the imaging subsystem is configured to monitor patient motion, e.g., to alert the system that images may have lower quality due to patient motion and/or to alert the system that the patient may be in a position that could interfere with motion of the multi-axis CT scanner. In some embodiments, the imaging subsystem is configured to find and/or identify ubiquitous rigid features of a human face (e.g., eye orbits, nose, ears, and/or mouth). In some embodiments, the imaging subsystem is configured to find and/or identify unique features (e.g., scars, tattoos, facial geometry). In some embodiments, the imaging subsystem is configured to track (e.g., using least-squares correlation) the ubiquitous features and unique features to track patient motion.

In some embodiments, the imaging subsystem is used to control motion of the gantry and/or scanner ring with respect to a patient. For example, in some embodiments, the imaging subsystem provides an image and/or a model of the multi-axis CT scanner and a superimposed computer-generated scan volume of the scanner ring as it moves along a planned trajectory to scan the patient. In some embodiments, the model presents a bounding box circumscribing the scan volume, e.g., in a side elevation and/or a top plan view to allow a user to confirm the positioning of the gantry and/or scan ring prior to the scan. In some embodiments, the imaging subsystem is used to monitor the trajectory of the gantry and/or the scanner ring to minimize and/or eliminate the chance that a collision with the patient will occur during the scan.

In some embodiments, the imaging subsystem is configured to identify the identity of a patient and/or is configured to verify the identity of a patient, e.g., using facial scanning recognition, optical scanning recognition, and/or other technologies for identifying a person and/or verifying the identity of a patient. In some embodiments, the imaging subsystem is configured to use a combination of the ubiquitous features and unique features of a patient to identify a patient and/or to verify patient identity. In some embodiments, the imaging subsystem comprises a technology for determining the spatial position of a target, e.g., as described in U.S. Pat. No. 5,923,417, incorporated herein by reference. In some embodiments, the imaging subsystem comprises a technology for determining the spatial position and orientation of a body, e.g., as described in U.S. Pat. No. 6,061,644, incorporated herein by reference. In some embodiments, the imaging subsystem comprises a technology for optical tracking, e.g., NDI OPTOTRAK (see, e.g., Northern Digital Inc. (NDI) "Optical Tracking Education Guide" June 2016, P/N 8300349 Rev 001, incorporated herein by reference). In some embodiments, the imaging subsystem comprises a technology for tracking a target comprising receiving a depth image of a target and analyzing the depth image with a prior-trained collection of known poses to find an exemplar pose that represents an observed pose of the target, e.g., as described in platform. U.S. Pat. No. 7,974,443, incorporated herein by reference. In some embodiments, the imaging subsystem comprises a technology for a system to provide a three-dimensional virtual environment, capture a patient image with a camera, and correlate a patient position in physical space with a patient position in the virtual environment (see, e.g., U.S. Pat. No. 8,009,022, incorporated herein by reference).

In some embodiments, systems comprise a multi-axis medical imaging apparatus (e.g., CT scanner) and a light curtain subsystem. In some embodiments, a controller controls the light curtain subsystem. In some embodiments, the light curtain subsystem comprises a light source to produce a light curtain and a light detector. In some embodiments, the light curtain envelopes a volume enclosed by the scanner ring of the multi-axis medical imaging apparatus (e.g., CT scanner). In some embodiments, penetrating the light curtain disrupts detection of the light curtain by the light detection. In some embodiments, penetrating the light curtain indicates that an object (e.g., the patient, a component of the multi-axis medical imaging apparatus (e.g., CT scanner) or system comprising a multi-axis medical imaging apparatus (e.g., CT scanner)) is in a position that could collide with the multi-axis medical imaging apparatus (e.g., CT scanner) upon movement of the multi-axis medical imaging apparatus (e.g., CT scanner). That is, in some embodiments, the light curtain marks a volume within which objects are considered in a proper position and/or in a safe position (e.g., to minimize and/or eliminate harm caused by collision with the multi-axis medical imaging apparatus (e.g., CT scanner)). In some embodiments, the light curtain comprises a plurality of light beams. In some embodiments, the light curtain comprises a plurality of laser light beams. In some embodiments, light (e.g., laser light) from a source is redirected by one or more mirrors to produce the light curtain. In some embodiments, light (e.g., laser light) is produced from a rotating source and a circular mirror ring redirects the light (e.g., laser light) to form a cylindrical light curtain.

Some portions of this description describe the embodiments of the technology in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times to refer to these arrangements of operations as modules, without loss of generality. The described operations and their associated modules may be embodied in software, firmware, hardware, or any combinations thereof.

Certain steps, operations, or processes described herein may be performed or implemented with one or more hardware or software modules, alone or in combination with other devices. In some embodiments, a software module is implemented with a computer program product comprising a computer-readable medium containing computer program code, which can be executed by a computer processor for performing any or all steps, operations, or processes described.

In some embodiments, systems comprise a computer and/or data storage provided virtually (e.g., as a cloud computing resource). In particular embodiments, the technology comprises use of cloud computing to provide a virtual computer system that comprises the components and/or performs the functions of a computer as described herein. Thus, in some embodiments, cloud computing provides infrastructure, applications, and software as described herein through a network and/or over the internet. In some embodiments, computing resources (e.g., data analysis, calculation, data storage, application programs, file storage, etc.) are remotely provided over a network (e.g., the internet). A "microprocessor" or "processor" refers to one or more microprocessors that can be configured to communicate in a stand-alone and/or a distributed environment and can be configured to communicate via wired or wireless communications with other processors, where such one or more processors can be configured to operate on one or more processor-controlled devices that can be similar or different devices. Furthermore, "memory", unless otherwise specified, can include one or more processor-readable and accessible memory elements and/or components that can be internal to the processor-controlled device, external to the processor-controlled device, and can be accessed via a wired or wireless network.

Embodiments of the technology may also relate to an apparatus for performing the operations herein. This apparatus may be specially constructed for the required purposes and/or it may comprise a general-purpose computing device selectively activated or reconfigured by a computer program stored in the computer. Such a computer program may be stored in a non-transitory, tangible computer readable storage medium or any type of media suitable for storing electronic instructions, which may be coupled to a computer system bus. Furthermore, any computing systems referred to in the specification may include a single processor or may be architectures employing multiple processor designs for increased computing capability.

In some embodiments, the technology (e.g., a system) comprises an image reconstruction component (e.g., a hardware component and/or a software component) within the scanner ring and the image reconstruction component is configured to produce (e.g., reconstruct) medical images, e.g., from raw data (e.g., from raw image data). In some embodiments, the technology (e.g., a system) comprises a data transfer component that communicates raw image data acquired by the scanner ring (e.g., acquired by a detector of the scanner ring) to a component configured to produce (e.g., reconstruct) medical images. In some embodiments, the scanner ring comprises the data transfer component and the component configured to produce (e.g., reconstruct) medical images is separate from the medical imaging apparatus (e.g., a computer connected to the medical imaging apparatus by a wired and/or wireless communications component).

Methods of Treatment

In some embodiments, the technology relates to methods of treatment (e.g., methods of treating a patient). For example, in some embodiments, methods comprise imaging a patient in a vertical position and treating said patient in said vertical position, e.g., seated, seated and leaning backward, seated and leaning forward, standing, standing and leaning backward, standing and leaning forward, perched, kneeling, kneeling and leaning forward, or kneeling and leaning backward. In some embodiments, a patient is imaged in a vertical position, imaged in a horizontal position, and treated in a horizontal position (e.g., using a treatment comprising a surgery).

In some embodiments, the patient has a lung disease. In some embodiments, the patient thoracic (e.g., lung) area is imaged and treated. In some embodiments, the patient has an orthopedic condition and the area of the body comprising the orthopedic condition is imaged and treated.

In some embodiments, methods comprise obtaining a diagnostic image of a patient in a vertical position (e.g., seated, seated and leaning backward, seated and leaning forward, standing, standing and leaning backward, standing and leaning forward, perched, kneeling, kneeling and leaning forward, or kneeling and leaning backward); and treating a patient in a vertical position (e.g., seated, seated and leaning backward, seated and leaning forward, standing, standing and leaning backward, standing and leaning forward, perched, kneeling, kneeling and leaning forward, or kneeling and leaning backward), e.g., the same vertical position as in the imaging. In some embodiments, methods comprise obtaining a diagnostic image of a patient in a vertical position (e.g., seated, seated and leaning backward, seated and leaning forward, standing, standing and leaning backward, standing and leaning forward, perched, kneeling, kneeling and leaning forward, or kneeling and leaning backward); obtaining a portal image of said patient (e.g., to align the patient properly for treatment) prior to treatment; and treating a patient in a vertical position (e.g., seated, seated and leaning backward, seated and leaning forward, standing, standing and leaning backward, standing and leaning forward, perched, kneeling, kneeling and leaning forward, or kneeling and leaning backward), e.g., the same vertical position as in the imaging. In some embodiments, treating the patient comprises moving (e.g., rotating) the patient and exposing the patient to treatment at a plurality of angles and/or positions on the patient body.

In some embodiments, methods comprise imaging a patient in a vertical position (e.g., using the medical imaging apparatus as described herein) and treating the patient in a vertical position (e.g., with a radiotherapy apparatus). In some embodiments, methods comprise imaging a patient in a vertical position (e.g., a stationary vertical position) using a moving (e.g., translating and/or rotating) scanner (e.g., using a medical imaging apparatus as described herein) and treating the patient in a vertical position by rotating the patient (e.g., slowly rotating the patient) and exposing the patient to radiation from a stationary radiotherapy apparatus.

In some embodiments, methods comprise obtaining a diagnostic image of a patient in a vertical position (e.g., seated, seated and leaning backward, seated and leaning forward, standing, standing and leaning backward, standing and leaning forward, perched, kneeling, kneeling and leaning forward, or kneeling and leaning backward); obtaining a treatment planning image of the patient in a horizontal position (e.g., lying, lying with knees bent); and treating the patient in a horizontal position (e.g., using surgery and/or by exposing the patient to radiation).

Uses

In some embodiments, the technology provided herein finds use in medical, clinical, and research settings. For example, in some embodiments, the technology finds use in imaging a biological system, e.g., an organism (e.g., an animal, a human), organ, tissue, and/or cell. In some embodiments, the technology finds use in imaging a head, neck, lungs, heart, circulatory system (e.g., arteries and/or veins), abdomen, pelvic region, gastrointestinal system, axial skeleton (e.g., spine), kidneys, and/or extremities. For example, in some embodiments, the technology finds use in diagnosing and/or treating a disease and/or injury. For example, the technology finds use in preventive medicine, disease screening, disease diagnosis, disease treatment, and/or disease monitoring. For example, in some embodiments, the technology finds use in diagnosing and/or treating a cancer. In some embodiments, the technology finds use in imaging the chest, e.g., for diagnosis of pneumothorax, emphysema, cardiomegaly, fibrosis, diaphragmatic hernias, empyema, atelectasis, pneumonia, pulmonary edema, pulmonary hemorrhage, primary lung malignancy, or a metastatic disease. In some embodiments, the technology finds use in diagnosing and/or treating a calcification, bone trauma, hemorrhage, edema, infarction, and/or tumor. The technology also finds use in research settings, e.g., to image an animal, human, organ, or tissue for research uses. The technology also finds use in veterinary medical settings, e.g., to image an animal, organ, or tissue for diagnosis and/or treatment. In some embodiments, the technology finds use in industrial uses, e.g., to image a non-biological object, e.g., to identify characteristics of construction, material defects, internal contents, etc., without breaking or otherwise disrupting the non-biological object.

Although the disclosure herein refers to certain illustrated embodiments, it is to be understood that these embodiments are presented by way of example and not by way of limitation. All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A multi-axis medical imaging apparatus comprising:
a stanchion assembly;
a gantry coupled to the stanchion assembly; and
a scanner ring translatably coupled to the gantry,
wherein said scanner ring is structured to translate 0.20-2.00 m relative to said gantry.

2. The multi-axis medical imaging apparatus of claim 1, wherein said scanner ring comprises an imaging source and a detector.

3. The multi-axis medical imaging apparatus of claim 1, wherein said gantry is rotatably coupled to said stanchion assembly.

4. The multi-axis medical imaging apparatus of claim 3, wherein said gantry is structured to rotate from 0-200 degrees relative to said stanchion assembly.

5. The multi-axis medical imaging apparatus of claim 1, wherein a counterbalanced assembly comprises said gantry and said scanner ring.

6. The multi-axis medical imaging apparatus of claim 1, wherein a force of 50 N or less rotates a counterbalanced assembly comprising said gantry and said scanner ring relative to said stanchion assembly; and/or wherein a force of 50 N or less translates said scanner ring relative to said gantry.

7. The multi-axis medical imaging apparatus of claim 1, wherein said stanchion assembly comprises a motor operatively engaged with said gantry.

8. The multi-axis medical imaging apparatus of claim 1, wherein said gantry comprises a motor operatively engaged with said stanchion assembly.

9. The multi-axis medical imaging apparatus of claim 1, wherein said gantry comprises a motor operatively engaged with said scanner ring.

10. The multi-axis medical imaging apparatus of claim 9, wherein said motor is coupled to a ball screw, a belt, or a chain.

11. The multi-axis medical imaging apparatus of claim 1, wherein said gantry comprises a supplemental mass component providing a counterweight for said scanner ring.

12. The multi-axis medical imaging apparatus of claim 11, wherein said multi-axis imaging apparatus comprises a motor structured to move said supplemental mass component and said scanner ring.

13. The multi-axis medical imaging apparatus of claim 1, wherein said multi-axis medical imaging apparatus is structured to record a medical image of a subject in a vertical or substantially vertical position.

14. The multi-axis medical imaging apparatus of claim 13, wherein said scanner ring is structured to move from a first position over the head of said subject to a second position around said subject.

15. The multi-axis medical imaging apparatus of claim 1, wherein said scanner ring has an inner diameter of 20 cm or more.

16. The multi-axis medical imaging apparatus of claim 10, wherein said ball screw comprises a threaded shaft having a diameter of 15-100 mm.

17. The multi-axis medical imaging apparatus of claim 16, wherein said motor is structured to translate said scanner ring 5-100 mm per revolution of said threaded shaft.

18. The multi-axis medical imaging apparatus of claim 1, wherein said scanner ring comprises an X-ray generator and an X-ray detector.

19. A multi-axis medical imaging apparatus comprising:
   a stanchion assembly;
   a gantry coupled to the stanchion assembly; and
   a scanner ring coupled to the gantry,
   wherein a force of 50 N or less rotates a counterbalanced assembly comprising said gantry and said scanner ring relative to said stanchion assembly; and/or
   wherein a force of 50 N or less translates said scanner ring relative to said gantry.

20. The multi-axis medical imaging apparatus of claim 19, wherein said scanner ring comprises an imaging source and a detector.

21. The multi-axis medical imaging apparatus of claim 19, wherein said gantry is rotatably coupled to said stanchion assembly.

22. The multi-axis medical imaging apparatus of claim 21, wherein said gantry is structured to rotate from 0-200 degrees relative to said stanchion assembly.

23. The multi-axis medical imaging apparatus of claim 19, wherein said scanner ring is translatably coupled to said gantry.

24. The multi-axis medical imaging apparatus of claim 23, wherein said scanner ring is structured to translate 0.20-2.00 m relative to said gantry.

25. The multi-axis medical imaging apparatus of claim 19, wherein a counterbalanced assembly comprises said gantry and said scanner ring.

26. The multi-axis medical imaging apparatus of claim 19, wherein said stanchion assembly comprises a motor operatively engaged with said gantry.

27. The multi-axis medical imaging apparatus of claim 19, wherein said gantry comprises a motor operatively engaged with said stanchion assembly.

28. The multi-axis medical imaging apparatus of claim 19, wherein said gantry comprises a motor operatively engaged with said scanner ring.

29. The multi-axis medical imaging apparatus of claim 28, wherein said motor is coupled to a ball screw, a belt, or a chain.

30. The multi-axis medical imaging apparatus of claim 19, wherein said gantry comprises a supplemental mass component providing a counterweight for said scanner ring.

31. The multi-axis medical imaging apparatus of claim 30, wherein said multi-axis imaging apparatus comprises a motor structured to move said supplemental mass component and said scanner ring.

32. The multi-axis medical imaging apparatus of claim 19, wherein said multi-axis medical imaging apparatus is structured to record a medical image of a subject in a vertical or substantially vertical position.

33. The multi-axis medical imaging apparatus of claim 32, wherein said scanner ring is structured to move from a first position over the head of said subject to a second position around said subject.

34. The multi-axis medical imaging apparatus of claim 19, wherein said scanner ring has an inner diameter of 20 cm or more.

35. The multi-axis medical imaging apparatus of claim 29, wherein said ball screw comprises a threaded shaft having a diameter of 15-100 mm.

36. The multi-axis medical imaging apparatus of claim 35, wherein said motor is structured to translate said scanner ring 5-100 mm per revolution of said threaded shaft.

37. The multi-axis medical imaging apparatus of claim 19, wherein said scanner ring comprises an X-ray generator and an X-ray detector.

38. A multi-axis medical imaging apparatus comprising:
   a stanchion assembly comprising a motor;
   a gantry operatively engaged with the motor; and
   a scanner ring coupled to the gantry.

39. The multi-axis medical imaging apparatus of claim 38, wherein said scanner ring comprises an imaging source and a detector.

40. The multi-axis medical imaging apparatus of claim 38, wherein said gantry is rotatably coupled to said stanchion assembly.

41. The multi-axis medical imaging apparatus of claim 40, wherein said gantry is structured to rotate from 0-200 degrees relative to said stanchion assembly.

42. The multi-axis medical imaging apparatus of claim 38, wherein said scanner ring is translatably coupled to said gantry.

43. The multi-axis medical imaging apparatus of claim 42, wherein said scanner ring is structured to translate 0.20-2.00 m relative to said gantry.

44. The multi-axis medical imaging apparatus of claim 38, wherein a counterbalanced assembly comprises said gantry and said scanner ring.

45. The multi-axis medical imaging apparatus of claim 38, wherein a force of 50 N or less rotates a counterbalanced assembly comprising said gantry and said scanner ring relative to said stanchion assembly; and/or wherein a force of 50 N or less translates said scanner ring relative to said gantry.

46. The multi-axis medical imaging apparatus of claim 38, wherein said gantry comprises a motor operatively engaged with said stanchion assembly.

47. The multi-axis medical imaging apparatus of claim 38, wherein said gantry comprises a motor operatively engaged with said scanner ring.

48. The multi-axis medical imaging apparatus of claim 47, wherein said motor is coupled to a ball screw, a belt, or a chain.

49. The multi-axis medical imaging apparatus of claim 38, wherein said gantry comprises a supplemental mass component providing a counterweight for said scanner ring.

50. The multi-axis medical imaging apparatus of claim 49, wherein said multi-axis imaging apparatus comprises a motor structured to move said supplemental mass component and said scanner ring.

51. The multi-axis medical imaging apparatus of claim 38, wherein said multi-axis medical imaging apparatus is structured to record a medical image of a subject in a vertical or substantially vertical position.

52. The multi-axis medical imaging apparatus of claim 51, wherein said scanner ring is structured to move from a first position over the head of said subject to a second position around said subject.

53. The multi-axis medical imaging apparatus of claim 38, wherein said scanner ring has an inner diameter of 20 cm or more.

54. The multi-axis medical imaging apparatus of claim 48, wherein said ball screw comprises a threaded shaft having a diameter of 15-100 mm.

55. The multi-axis medical imaging apparatus of claim 54, wherein said motor is structured to translate said scanner ring 5-100 mm per revolution of said threaded shaft.

56. The multi-axis medical imaging apparatus of claim 38, wherein said scanner ring comprises an X-ray generator and an X-ray detector.

57. A multi-axis medical imaging apparatus comprising:
a stanchion assembly;
a gantry coupled to the stanchion assembly; and
a scanner ring coupled to the gantry,
wherein said gantry comprises a supplemental mass component providing a counterweight for said scanner ring.

58. The multi-axis medical imaging apparatus of claim 57, wherein said scanner ring comprises an imaging source and a detector.

59. The multi-axis medical imaging apparatus of claim 57, wherein said gantry is rotatably coupled to said stanchion assembly.

60. The multi-axis medical imaging apparatus of claim 59, wherein said gantry is structured to rotate from 0-200 degrees relative to said stanchion assembly.

61. The multi-axis medical imaging apparatus of claim 57, wherein said scanner ring is translatably coupled to said gantry.

62. The multi-axis medical imaging apparatus of claim 61, wherein said scanner ring is structured to translate 0.20-2.00 m relative to said gantry.

63. The multi-axis medical imaging apparatus of claim 57, wherein a counterbalanced assembly comprises said gantry and said scanner ring.

64. The multi-axis medical imaging apparatus of claim 57, wherein a force of 50 N or less rotates a counterbalanced assembly comprising said gantry and said scanner ring relative to said stanchion assembly; and/or wherein a force of 50 N or less translates said scanner ring relative to said gantry.

65. The multi-axis medical imaging apparatus of claim 57, wherein said stanchion assembly comprises a motor operatively engaged with said gantry.

66. The multi-axis medical imaging apparatus of claim 57, wherein said gantry comprises a motor operatively engaged with said stanchion assembly.

67. The multi-axis medical imaging apparatus of claim 57, wherein said gantry comprises a motor operatively engaged with said scanner ring.

68. The multi-axis medical imaging apparatus of claim 67, wherein said motor is coupled to a ball screw, a belt, or a chain.

69. The multi-axis medical imaging apparatus of claim 57, wherein said multi-axis imaging apparatus comprises a motor structured to move said supplemental mass component and said scanner ring.

70. The multi-axis medical imaging apparatus of claim 57, wherein said multi-axis medical imaging apparatus is structured to record a medical image of a subject in a vertical or substantially vertical position.

71. The multi-axis medical imaging apparatus of claim 70, wherein said scanner ring is structured to move from a first position over the head of said subject to a second position around said subject.

72. The multi-axis medical imaging apparatus of claim 57, wherein said scanner ring has an inner diameter of 20 cm or more.

73. The multi-axis medical imaging apparatus of claim 68, wherein said ball screw comprises a threaded shaft having a diameter of 15-100 mm.

74. The multi-axis medical imaging apparatus of claim 73, wherein said motor is structured to translate said scanner ring 5-100 mm per revolution of said threaded shaft.

75. The multi-axis medical imaging apparatus of claim 57, wherein said scanner ring comprises an X-ray generator and an X-ray detector.

76. A multi-axis medical imaging apparatus comprising:
a stanchion assembly;
a gantry coupled to the stanchion assembly; and
a scanner ring coupled to the gantry,
wherein said multi-axis medical imaging apparatus is structured to record a medical image of a subject in a vertical or substantially vertical position; and
wherein said scanner ring is structured to move from a first position over the head of said subject to a second position around said subject.

77. The multi-axis medical imaging apparatus of claim 76, wherein said scanner ring comprises an imaging source and a detector.

78. The multi-axis medical imaging apparatus of claim 76, wherein said gantry is rotatably coupled to said stanchion assembly.

79. The multi-axis medical imaging apparatus of claim 78, wherein said gantry is structured to rotate from 0-200 degrees relative to said stanchion assembly.

80. The multi-axis medical imaging apparatus of claim 76, wherein said scanner ring is translatably coupled to said gantry.

81. The multi-axis medical imaging apparatus of claim 80, wherein said scanner ring is structured to translate 0.20-2.00 m relative to said gantry.

82. The multi-axis medical imaging apparatus of claim 76, wherein a counterbalanced assembly comprises said gantry and said scanner ring.

83. The multi-axis medical imaging apparatus of claim 76, wherein a force of 50 N or less rotates a counterbalanced assembly comprising said gantry and said scanner ring relative to said stanchion assembly; and/or wherein a force of 50 N or less translates said scanner ring relative to said gantry.

84. The multi-axis medical imaging apparatus of claim 76, wherein said stanchion assembly comprises a motor operatively engaged with said gantry.

85. The multi-axis medical imaging apparatus of claim 76, wherein said gantry comprises a motor operatively engaged with said stanchion assembly.

86. The multi-axis medical imaging apparatus of claim 76, wherein said gantry comprises a motor operatively engaged with said scanner ring.

87. The multi-axis medical imaging apparatus of claim 86, wherein said motor is coupled to a ball screw, a belt, or a chain.

88. The multi-axis medical imaging apparatus of claim 76, wherein said gantry comprises a supplemental mass component providing a counterweight for said scanner ring.

89. The multi-axis medical imaging apparatus of claim 88, wherein said multi-axis imaging apparatus comprises a motor structured to move said supplemental mass component and said scanner ring.

90. The multi-axis medical imaging apparatus of claim 76, wherein said scanner ring has an inner diameter of 20 cm or more.

91. The multi-axis medical imaging apparatus of claim 87, wherein said ball screw comprises a threaded shaft having a diameter of 15-100 mm.

92. The multi-axis medical imaging apparatus of claim 91, wherein said motor is structured to translate said scanner ring 5-100 mm per revolution of said threaded shaft.

93. The multi-axis medical imaging apparatus of claim 76, wherein said scanner ring comprises an X-ray generator and an X-ray detector.

* * * * *